(12) United States Patent
Lee et al.

(10) Patent No.: US 7,612,094 B2
(45) Date of Patent: Nov. 3, 2009

(54) TRI-SUBSTITUTED HETEROARYLS AND METHODS OF MAKING AND USING THE SAME

(75) Inventors: Wen-Cherng Lee, Lexington, MA (US); Lihong Sun, Arlington, MA (US); Feng Shan, Burlington, MA (US); Claudio Chuaqui, Somerville, MA (US); Zhongli Zheng, Lexington, MA (US); Russell C. Petter, Stow, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 563 days.

(21) Appl. No.: 10/510,459

(22) PCT Filed: Apr. 4, 2003

(86) PCT No.: PCT/US03/10440

§ 371 (c)(1),
(2), (4) Date: Aug. 25, 2005

(87) PCT Pub. No.: WO03/087304

PCT Pub. Date: Oct. 23, 2003

(65) Prior Publication Data

US 2006/0063809 A1    Mar. 23, 2006

Related U.S. Application Data

(60) Provisional application No. 60/369,793, filed on Apr. 4, 2002.

(51) Int. Cl.
*A61K 31/4545* (2006.01)
*C07D 401/14* (2006.01)

(52) U.S. Cl. .............. 514/318; 546/194; 546/119; 546/272.7; 544/284; 544/353; 514/249; 514/259; 514/303; 514/338

(58) Field of Classification Search ................ 514/318, 514/338, 303, 259, 249; 546/194, 272.7, 546/119; 544/284, 353
See application file for complete search history.

(56) References Cited

U.S. PATENT DOCUMENTS

| | | | |
|---|---|---|---|
| 3,940,486 A | 2/1976 | Fitzi |
| 4,302,464 A | 11/1981 | LaMattina et al. |
| 5,514,505 A | 5/1996 | Limburg et al. |
| 5,593,991 A | 1/1997 | Adams et al. |
| 5,593,992 A | 1/1997 | Adams et al. |
| 5,604,240 A | 2/1997 | Chambers et al. |
| 5,656,644 A | 8/1997 | Adams et al. |
| 5,658,903 A | 8/1997 | Adams et al. |
| 5,663,334 A | 9/1997 | Sheldrake et al. |
| 5,670,527 A | 9/1997 | Adams et al. |
| 5,686,455 A | 11/1997 | Adams et al. |
| 5,716,955 A | 2/1998 | Adams et al. |
| 5,717,100 A | 2/1998 | Selnick et al. |
| 5,739,143 A | 4/1998 | Adams et al. |
| 5,756,499 A | 5/1998 | Adams et al. |
| 5,792,778 A | 8/1998 | De Laszlo et al. |
| 5,811,549 A | 9/1998 | Adams et al. |
| 5,837,719 A | 11/1998 | De Laszlo et al. |
| 5,854,264 A | 12/1998 | Anthony et al. |
| 5,854,265 A | 12/1998 | Anthony et al. |
| 5,854,276 A | 12/1998 | Okudaira et al. |
| 5,859,041 A | 1/1999 | Liverton et al. |
| 5,864,036 A | 1/1999 | Adams et al. |
| 5,869,660 A | 2/1999 | Adams et al. |
| 5,872,136 A | 2/1999 | Anthony et al. |
| 5,880,140 A | 3/1999 | Anthony et al. |
| 5,883,105 A | 3/1999 | Anthony et al. |
| 5,916,891 A | 6/1999 | Adams et al. |
| 5,917,043 A | 6/1999 | Sisco et al. |
| 5,932,576 A | 8/1999 | Anantanarayan et al. |
| 5,939,439 A | 8/1999 | Anthony et al. |
| 5,939,557 A | 8/1999 | Anthony et al. |
| 5,965,583 A | 10/1999 | Beers et al. |
| 5,969,184 A | 10/1999 | Adams et al. |
| 5,977,103 A | 11/1999 | Adams et al. |
| 5,998,425 A | 12/1999 | Adams et al. |
| 6,040,320 A | 3/2000 | Beers et al. |
| 6,046,208 A | 4/2000 | Adams et al. |
| 6,051,574 A | 4/2000 | Anthony et al. |
| 6,077,853 A | 6/2000 | Graham et al. |
| 6,080,870 A | 6/2000 | Anthony et al. |

(Continued)

FOREIGN PATENT DOCUMENTS

DE        3029376        3/1982

(Continued)

OTHER PUBLICATIONS

International Search Report, Sep. 25, 2003.

(Continued)

*Primary Examiner*—Charanjit S Aulakh
(74) *Attorney, Agent, or Firm*—Honigman; Thomas A. Wootton; Jonathan P. O'Brien

(57) ABSTRACT

Compounds of formula (I) possess unexpectedly high affinity for Alk 5 and/or Alk 4, and can be useful as antagonists thereof for preventing and/or treating numerous diseases, including fibrotic disorders.

In one embodiment, the invention features a compound of the general formula (I).

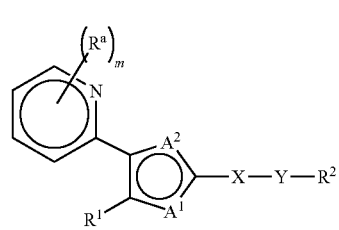

(I)

21 Claims, No Drawings

U.S. PATENT DOCUMENTS

| | | | |
|---|---|---|---|
| 6,083,949 A | 7/2000 | Liverton et al. |
| 6,087,381 A | 7/2000 | Hanson et al. |
| 6,096,739 A | 8/2000 | Feuerstein et al. |
| 6,096,748 A | 8/2000 | Gallagher et al. |
| 6,100,399 A | 8/2000 | Sisco et al. |
| 6,103,936 A | 8/2000 | Adams et al. |
| 6,136,828 A | 10/2000 | Elliott et al. |
| 6,150,557 A | 11/2000 | Adams et al. |
| 6,180,643 B1 | 1/2001 | Zablocki et al. |
| 6,214,844 B1 | 4/2001 | Adams et al. |
| 6,218,537 B1 | 4/2001 | Adams et al. |
| 6,222,036 B1 | 4/2001 | Peng et al. |
| 6,235,760 B1 | 5/2001 | Feuerstein et al. |
| 6,239,279 B1 | 5/2001 | Sisko et al. |
| 6,255,491 B1 | 7/2001 | Sisko et al. |
| 6,268,370 B1 | 7/2001 | Adams et al. |
| 6,288,089 B1 | 9/2001 | Zawada et al. |
| 6,300,347 B1 | 10/2001 | Revesz et al. |
| 6,335,336 B1 | 1/2002 | Anantanarayan et al. |
| 6,335,340 B1 | 1/2002 | Gallagher |
| 6,369,068 B1 | 4/2002 | Adams et al. |
| 6,372,741 B1 | 4/2002 | Jackson et al. |
| 6,387,898 B1 | 5/2002 | Feuerstein et al. |
| 6,399,644 B1 | 6/2002 | Wexler et al. |
| 6,410,729 B1 | 6/2002 | Spohr et al. |
| 6,420,385 B1 | 7/2002 | Spohr et al. |
| 6,423,713 B1 | 7/2002 | Anantanarayan et al. |
| 6,440,973 B1 | 8/2002 | Zablocki et al. |
| 6,465,493 B1 | 10/2002 | Burgess et al. |
| 6,503,930 B1 | 1/2003 | Hanson et al. |
| 6,511,997 B1 | 1/2003 | Minami et al. |
| 6,514,977 B1 | 2/2003 | Anantanarayan et al. |
| 6,525,059 B1 | 2/2003 | Anantanarayan et al. |
| 6,528,512 B1 | 3/2003 | Gallagher et al. |
| 6,548,503 B1 | 4/2003 | Adams et al. |
| 6,562,832 B1 | 5/2003 | Adams et al. |
| 6,579,873 B2 | 6/2003 | Anantanarayan et al. |
| 6,579,874 B2 | 6/2003 | Revesz et al. |
| 6,599,910 B1 | 7/2003 | Adams et al. |
| 6,599,926 B2 | 7/2003 | Pinto et al. |
| 6,602,877 B1 | 8/2003 | Bamborough et al. |
| 6,605,634 B2 | 8/2003 | Zablocki et al. |
| 6,610,688 B2 | 8/2003 | Liang et al. |
| 6,610,698 B2 | 8/2003 | Spohr et al. |
| 6,617,324 B1 | 9/2003 | Naraian et al. |
| 6,630,325 B1 | 10/2003 | Lindner et al. |
| 6,645,989 B2 | 11/2003 | Adams et al. |
| 6,649,604 B2 | 11/2003 | Spohr et al. |
| 6,667,325 B1 | 12/2003 | Minami et al. |
| 6,689,770 B2 | 2/2004 | Wexler et al. |
| 6,727,364 B2 | 4/2004 | Tullis et al. |
| 6,730,683 B2 | 5/2004 | Gallagher |
| 6,774,127 B2 | 8/2004 | Adams et al. |
| 6,787,555 B2 | 9/2004 | Tullis et al. |
| 6,852,740 B2 | 2/2005 | Hanson et al. |
| 6,861,417 B2 | 3/2005 | Adams et al. |
| 2002/0032183 A1 | 3/2002 | LoGrasso et al. |
| 2002/0049220 A1 | 4/2002 | Revesz et al. |
| 2002/0086869 A1 | 7/2002 | Anantanarayan et al. |
| 2002/0103202 A1 | 8/2002 | Pinto et al. |
| 2002/0123500 A1 | 9/2002 | Jackson et al. |
| 2002/0156104 A1 | 10/2002 | Adams et al. |
| 2002/0161211 A1 | 10/2002 | Lindner et al. |
| 2002/0183319 A1 | 12/2002 | Liang et al. |
| 2002/0198206 A1 | 12/2002 | Gallagher |
| 2003/0013712 A1 | 1/2003 | Tullis et al. |
| 2003/0050315 A1 | 3/2003 | Wexler et al. |
| 2003/0069243 A1 | 4/2003 | Adams et al. |
| 2003/0069425 A1 | 4/2003 | Spohr et al. |
| 2003/0073704 A1 | 4/2003 | Spohr et al. |
| 2003/0078274 A1 | 4/2003 | Lipton et al. |
| 2003/0096819 A1 | 5/2003 | Zablocki et al. |
| 2003/0100558 A1 | 5/2003 | Tullis et al. |
| 2003/0113787 A1 | 6/2003 | Bertin |
| 2003/0114452 A1 | 6/2003 | Adams et al. |
| 2003/0144529 A1 | 7/2003 | Hanson et al. |
| 2003/0149277 A1 | 8/2003 | Gaster et al. |
| 2003/0153569 A1 | 8/2003 | Adams et al. |
| 2003/0153588 A1 | 8/2003 | Steadman et al. |
| 2003/0158238 A1 | 8/2003 | Hale et al. |
| 2003/0166633 A1 | 9/2003 | Gaster et al. |
| 2003/0191116 A1 | 10/2003 | Kalindjian et al. |
| 2003/0229110 A1 | 12/2003 | Adams et al. |
| 2004/0014776 A1 | 1/2004 | Breault et al. |
| 2004/0014973 A1 | 1/2004 | Adams et al. |
| 2004/0038856 A1 | 2/2004 | Chakravarty et al. |
| 2004/0038964 A1 | 2/2004 | Dean et al. |
| 2004/0038991 A1 | 2/2004 | Bamborough et al. |
| 2004/0039198 A1 | 2/2004 | Bender et al. |
| 2004/0053924 A1 | 3/2004 | Liang et al. |
| 2004/0053942 A1 | 3/2004 | Alberti et al. |
| 2004/0053943 A1 | 3/2004 | Adams et al. |
| 2004/0063176 A1 | 4/2004 | Lindner et al. |
| 2004/0063745 A1 | 4/2004 | Gellibert |
| 2004/0063949 A1 | 4/2004 | Gellibert |
| 2004/0077687 A1 | 4/2004 | Gellibert |
| 2004/0087623 A1 | 5/2004 | Gellibert |
| 2004/0087628 A1 | 5/2004 | Minami et al. |
| 2004/0097502 A1 | 5/2004 | Gellibert |
| 2004/0106608 A1 | 6/2004 | Munchhof et al. |
| 2004/0110797 A1 | 6/2004 | Munchhof et al. |
| 2004/0147579 A1 | 7/2004 | Naraian et al. |
| 2004/0152738 A1 | 8/2004 | Gaster et al. |
| 2004/0157861 A1 | 8/2004 | Scarborough et al. |
| 2004/0176433 A1 | 9/2004 | Naraian et al. |
| 2004/0214816 A1 | 10/2004 | Beers et al. |
| 2004/0220230 A1 | 11/2004 | Gaster et al. |
| 2004/0248903 A1 | 12/2004 | Gudmundsson et al. |
| 2004/0266842 A1 | 12/2004 | Gaster et al. |

FOREIGN PATENT DOCUMENTS

| | | |
|---|---|---|
| EP | 0809499 | 12/1997 |
| GB | 2306108 | 4/1997 |
| JP | 01181187 | 7/1989 |
| JP | 02114784 | 4/1990 |
| JP | 02216969 | 8/1990 |
| JP | 08183787 | 7/1996 |
| JP | 2002-114780 | 4/2002 |
| WO | WO 9216527 | 10/1992 |
| WO | WO 9502591 | 1/1995 |
| WO | WO 9503297 | 2/1995 |
| WO | WO 9618626 | 6/1996 |
| WO | WO 9621452 | 7/1996 |
| WO | WO 9640143 | 12/1996 |
| WO | WO 9716426 | 5/1997 |
| WO | WO 9716441 | 5/1997 |
| WO | WO 9723479 | 7/1997 |
| WO | WO 9725046 | 7/1997 |
| WO | WO 9736582 | 10/1997 |
| WO | WO 9825619 | 6/1998 |
| WO | WO 9857966 | 12/1998 |
| WO | WO 9903480 | 1/1999 |
| WO | WO 9918942 | 4/1999 |
| WO | WO 9958128 | 11/1999 |
| WO | WO 9961437 | 12/1999 |
| WO | WO 0001688 | 1/2000 |
| WO | WO 0023444 | 4/2000 |
| WO | WO 0026209 | 5/2000 |
| WO | WO 0122965 | 4/2001 |
| WO | WO 0137835 | 5/2001 |
| WO | WO 0138324 | 5/2001 |
| WO | WO 0200651 | 1/2002 |
| WO | WO 02055077 | 7/2002 |

| | | |
|---|---|---|
| WO | WO 02062793 | 8/2002 |
| WO | WO 02087591 | 11/2002 |
| WO | WO 02088107 | 11/2002 |
| WO | WO 02092593 | 11/2002 |
| WO | WO 03015781 | 2/2003 |
| WO | WO 03087304 | 10/2003 |
| WO | WO 03091226 | 11/2003 |
| WO | WO 2004005282 | 1/2004 |
| WO | WO 2004013125 | 2/2004 |
| WO | WO 2004013135 | 2/2004 |
| WO | WO 2004013138 | 2/2004 |
| WO | WO 2004016606 | 2/2004 |
| WO | WO 2004026307 | 4/2004 |
| WO | WO 2004029043 | 4/2004 |
| WO | WO 2004048382 | 6/2004 |
| WO | WO 2004065392 | 8/2004 |
| WO | WO 2004111036 | 12/2004 |
| WO | WO 2004111046 | 12/2004 |

OTHER PUBLICATIONS

Supplemental European Search Report, Mar. 21, 2006.
Alexandrow, Mark G., and Moses, Harold L., "Transforming Growth Factor β and Cell Cycle Regulation," *Cancer Research*, 55: 1452-1457 (1995).
Blobe, Gerard C., et al., "Role of Transforming Growth Factor β in Human Disease," *The New England Journal of Medicine*, 342 (18): 1350-1358 (2000).
Border, Wayne A. and Noble, Nancy A., "Transforming Growth Factor β in Tissue Fibrosis," *The New England Journal of Medicine*, 331 (19): 1286-1292 (1994).
Border, Wayne A. and Ruoslahti Erkki, "Transforming Growth Factor β in Disease: The Dark Side of Tissue Repair," *J. Clin. Invest*,. 90: 1-7 (1992).
Byfield, Stacey DaCosta, et al., "SB-505124 Is a Selective Inhibitor of Transforming Growth Factor-β Type I Receptors ALK4, ALK5, and ALK7," *Molecular Pharmacology*, 65 (3): 744-752 (2003).
Cipriano, Sherry C., et al., "Follistatin Is a Modulator of Gonadal Tumor Progression and the Activin-Induced Wasting Syndrome in Inhibin-Deficient Mice," *Endocrinology*, 141 (7): 2319-2327 (2000).
Coerver, Katherine A., et al., "Activin Signaling Through Activin Receptor Type II Causes the Cachexia-Like Symptoms in Inhibin-Deficient Mice," *Molecular Endocrinology*, 10: 534-543 (1996).
Dahly, Annette J., et al., "Antihypertensive Effects of Chronic Anti-TGF-β Antibody Therapy in Dahl S Rats," *American Journal. Physiological Regul. Integr. Comp. Physiol.*, 283: R757-767 (2002).
De Bleser, Pieter J., et al., "Localization and Cellular Sources of Activins in Normal and Fibrotic Rat Liver," *Hepatology*, 26: 905-912 (1997).
De Groot, Corline J. A., et al., "Expression of Transforming Growth Factor (TGF)-β1, -β2, and β3 Isoforms and TGF-β Type I and Type II Receptors in Multiple Sclerosis Lesions and Human Adult Astrocyte Cultures," *Journal of Neuropathology and Experimental Neurology*, 58 (2): 174-187 (1999).
Freireich, Emil J., et al., "Quantitative Comparison of Toxicity of Anticancer Agents in Mouse, Rat, Hamster, Dog, Monkey, and Man," *Cancer Chemotherapy Reports*, 50 (4): 219-244 (1996).
Hojo, Minoru, et al., "Cyclosporine Induces Cancer Progression by a Cell-Autonomous Mechanism," *Nature*, 397: 530-534 (1999).
Huang, Sheng-Tung and Gordon, Dana M., "Total synthesis of endothelin-converting enzyme antagonist WS75624 B," *Tetrahedron Letters*, 39 (51): 9335-9338 (1998).
Huse, Morgan, et al., "The TGFβ Receptor Activation Process: An Inhibitor- to Substrate-Binding Switch," *Molecular Cell*, 8: 671-682 (2001).
Inoue, Satoshi, et al., "Demonstration of Activin-A in Arteriosclerotic Lesions," *Biochemical and Biophysical Research Communications*, 205 (1): 441-448 (1994).
John, Gareth R., et al., "Multiple Sclerosis: Re-expression of a Developmental Pathway that Restricts Oligodendrocyte Maturation," *Nature. Medicine*, 8 (10): 1115-1121 (2002).

Journet, Michel, et al., "An Improved and Practical Procedure for the Synthesis of Substituted Phenylacetylpyridines," *Tetrahedron Letters*, 39: 1717-1720 (1998).
Krempen, Kimberly, et al., "Far Upstream Regulatory Elements Enhance Position-Independent and Uterus-Specific Expression of the Murine α1 (O) Collagen Promoter in Transgenic Mice," *Gene Expression*, 8: 151-163 (1999).
Laping, Nicholas J., "ALK5 Inhibition in Renal Disease," *Current Opinion in Pharmacology*, 3: 204-208 (2003).
Lecount, David J. and Jarvis, John A. J., "Reaction of 5-Chloropyridin-2-yl-thioureas with Phenacyl Bromides: A New Thiazole Synthesis. X-ray Crystal Structure of 5-(5-Chloropyridin-2-yl)-2-diethylamino-4-phenylthiazole," *Journal of the Chemical Society*, 1977, 8: 282-283 (1977).
Liverton, Nigel J., et al., "Design and Synthesis of Potent, Selective, and Orally Bioavailable Tetrasubstituted Imidazole Inhibitors of p38 Mitogen Activated Protein Kinase," *Journal of Medicinal Chemistry*, 42: 2180-2190 (1999).
Logan, Ann, et al., "Inhibition of Glial Scarring in the Injured Rat Brain by a Recombinant Human Monoclonal Antibody to Transforming Growth Factor-β2," *European Journal of Neuroscience*, 11: 2367-2374 (1999).
Logan, Ann et al., "Decorin Attenuates Gliotic Scar Formation in the Rat Cerebral Hemisphere," *Experimental Neurology*, 159: 504-510 (1999).
Maehara, Yoshihiko, et al., "Role of Transforming Growth Factor-β1 in Invasion and Metastasis in Gastric Carcinoma," *Journal of Clinical Oncology*, 17 (2): 607-614 (1999).
Masliah, Eliezer, et al., "Functional Role of TGFβ in Alzheimer's Disease Microvascular Injury: Lessons from Transgenic Mice," *Neurochemistry International*, 39: 393-400 (2001).
Massagué, Joan, "TGF-β Signal Transduction," *Annual Review Biochem. Med.* 67: 773-791 (1998).
Massagué, Joan, "The Transforming Growth Factor-β Family," *Annual Review Cell. Biol.*, 6: 594-641 (1990).
Matsuse, Takeshi, et al., "Expression of Immunoreactive Activin A Protein in Remodeling Lesions Associated with Interstitial Pulmonary Fibrosis," *American Journal of Pathology*, 148 (3): 707-713 (1996).
Matsuse, Takeshi, et al., "Expression of Immunoreactive and Bioactive Activin A Protein in Adult Murine Lung After Bleomycin Treatment," *American Journal of Respiratory Cell and Molecular Biology*, 13: 17-24 (1995).
Matzuk, M. M., et al., "Development of Cancer Cachexia-Like Syndrome and Adrenal Tumors in Inhibin-Deficient Mice," *Proc. Natl. Acad. Sci. USA* 91: 8817-8821 (1994).
Munz, Barbara, et al., "Overexpression of Activin A in the Skin of Transgenic Mice Reveals New Activities of Activin in Epidermal Morphogenesis, Dermal Fibrosis and Wound Repair," *The EMBO Journal*, 18 (19): 5205-5215 (1999).
Pawlowski, John E., et al., "Stimulation of Activin A Expression in Rat Aortic Smooth Muscle Cells by Thrombin and Angiotensin II Correlates with Neointimal Formation in Vivo," *J. Clin. Invest.* 100 (3): 639-648 (1997).
Picon, Antonio, et al., "A Subset of Metastatic Human Colon Cancers Expresses Elevated Levels of Transforming Growth Factor β1," *Cancer Epidemiology Biomarkers & Prevention*,. 7: 497-504 (1998).
Revesz, Laszlo, et al., "SAR of 4-Hydroxypiperidine and Hydroxyalkyl Substituted Heterocycles as Novel p38 Map Kinase Inhibitors," *Bioorganic & Medicinal Chemistry Letters*, 10: 1261-1264 (2000).
Roberts, A. B. and Sporn M. B., "The Transforming Growth Factor-βs," *Peptide Growth Factors and Their Receptors* 95: 419-472 Berlin: Springer-Verlag (1990).

Roberts, Anita B. and Sporn Michael B., "Physiological Actions and Clinical Applications of Transforming Growth Factor-β (TGF-β)," *Growth Factors* 8: 1-9 (1993).

Rosendahl, Alexander, et al., "Activation of the TGF-β/Activin-Smad2 Pathway During Allergic Airway Inflammation," *American Journal of Respiratory Cell and Molecular Biology*, 25: 60-68 (2001).

Sugiyama, Motoya, et al., "Expression of Activin A is Increased in Cirrhotic and Fibrotic Rat Livers," *Gastroenterology*, 114: 550-558 (1998).

Xu, Shiwen, et al., "Scleroderma-Derived Human Fibroblasts Retain Abnormal Phenotypic and Functional Characteristics Following Retroviral Transduction with the SV40 tsT Antigen," *Experimental Cell Research*, 220: 407-414 (1995).

TRI-SUBSTITUTED HETEROARYLS AND METHODS OF MAKING AND USING THE SAME

This is a continuation of PCT/US03/10440, filed Apr. 4, 2003, which is a continuation-in-part of provisional application 60/369,793, filed Apr. 4, 2002. The entire disclosure of each of the aforesaid patent applications are incorporated herein by reference.

BACKGROUND OF THE INVENTION

TGFβ (Transforming Growth Factor β) is a member of a large family of dimeric polypeptide growth factors that includes, for example, activins, inhibins, bone morphogenetic proteins (BMPs), growth and differentiation factors (GDFs) and mullerian inhibiting substance (MIS). TGFβ exists in three isoforms (TGFβ1, TGFβ2, and TGFβ3) and is present in most cells, along with its receptors. Each isoform is expressed in both a tissue-specific and developmentally regulated fashion. Each TGFβ isoform is synthesized as a precursor protein that is cleaved intracellularly into a C-terminal region (latency associated peptide (LAP)) and an N-terminal region known as mature or active TGFβ. LAP is typically non-covalently associated with mature TGFβ prior to secretion from the cell. The LAP-TGFβ complex cannot bind to the TGFβ receptors and is not biologically active. TGFβ is generally released (and activated) from the complex by a variety of mechanisms including, for example, interaction with thrombospondin-1 or plasmin.

Following activation, TGFβ binds at high affinity to the type II receptor (TGFβRII), a constitutively active serine/threonine kinase. The ligand-bound type II receptor phosphorylates the TGFβ type I receptor (Alk 5) in a glycine/serine rich domain, which allows the type I receptor to recruit and phosphorylate downstream signaling molecules, Smad2 or Smad3. See, e.g., Huse, M. et al., *Mol. Cell.* 8: 671-682 (2001). Phosphorylated Smad2 or Smad3 can then complex with Smad4, and the entire hetero-Smad complex translocates to the nucleus and regulates transcription of various TGFβ-responsive genes. See, e.g., Massagué, J. *Ann. Rev. Biochem. Med.* 67: 773 (1998).

Activins are also members of the TGFβ superfamily, which are distinct from TGFβ in that they are homo- or heterodimers of activin βa or βb. Activins signal in a manner similar to TGFβ, that is, by binding to a constitutive serine-threonine receptor kinase, activin type II receptor (ActRIIB), and activating a type I serine-threonine receptor, Alk 4, to phosphorylate Smad2 or Smad3. The consequent formation of a hetero-Smad complex with Smad4 also results in the activin-induced regulation of gene transcription.

Indeed, TGFβ and related factors such as activin regulate a large array of cellular processes, e.g., cell cycle arrest in epithelial and hematopoietic cells, control of mesenchymal cell proliferation and differentiation, inflammatory cell recruitment, immunosuppression, wound healing, and extracellular matrix production. See, e.g., Massagué, J. *Ann. Rev. Cell. Biol.* 6: 594-641 (1990); Roberts, A. B. and Sporn M. B. *Peptide Growth Factors and Their Receptors*, 95: 419-472 Berlin: Springer-Verlag (1990); Roberts, A. B. and Sporn M. B. *Growth Factors* 8:1-9 (1993); and Alexandrow, M. G., Moses, H. L. *Cancer Res.* 55: 1452-1457 (1995). Hyperactivity of TGFβ signaling pathway underlies many human disorders (e.g., excess deposition of extracellular matrix, an abnormally high level of inflammatory responses, fibrotic disorders, and progressive cancers). Similarly, activin signaling and overexpression of activin is linked to pathological disorders that involve extracellular matrix accumulation and fibrosis (see, e.g., Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al, *Am. J. Pathol.* 148: 707-713 (1996); De Bleser et al., *Hepatology* 26: 905-912 (1997); Pawlowski, J. E., et al., *J. Clin. Invest.* 100: 639-648 (1997); Sugiyama, M. et al., *Gastroenterology* 114: 550-558 (1998); Munz, B. et al., *EMBO J.* 18: 5205-5215 (1999)), inflammatory responses (see, e.g., Rosendahl, A. et al., *Am. J. Repir. Cell Mol. Biol.* 25: 60-68 (2001)), cachexia or wasting (see Matzuk, M. M. et al., *Proc. Nat. Acad. Sci. USA* 91: 8817-8821 (1994); Coerver, K. A. et al, *Mol. Endocrinol.* 10: 534-543 (1996); Cipriano, S. C. et al. *Endocrinology* 141: 2319-27 (2000)), diseases of or pathological responses in the central nervous system (see Logan, A. et al. *Eur. J. Neurosci.* 11: 2367-2374 (1999); Logan, A. et al. *Exp. Neurol.* 159: 504-510 (1999); Masliah, E. et al., Neurochem. Int. 39: 393-400 (2001); De Groot, C. J. A. et al, *J. Neuropathol. Exp. Neurol.* 58: 174-187 (1999), John, G. R. et al, *Nat Med.* 8: 1115-21 (2002)) and hypertension (see Dahly, A. J. et al., *Am. J. Physiol. Regul. Integr. Comp. Physiol.* 283: R757-67 (2002)). Studies have shown that TGFβ and activin can act synergistically to induce extracellular matrix production (see, e.g., Sugiyama, M. et al., *Gastroenterology* 114: 550-558, (1998)). It is therefore desirable to develop modulators (e.g., antagonists) to members of the TGFβ family to prevent and/or treat disorders involving this signaling pathway.

SUMMARY OF THE INVENTION

The invention is based on the discovery that compounds of formula (I) are unexpectedly potent antagonists of the TGFβ family type I receptors, Alk5 and/or Alk 4. Thus, compounds of formula (I) can be employed in the prevention and/or treatment of diseases such as fibrosis (e.g., renal fibrosis, pulmonary fibrosis, and hepatic fibrosis), progressive cancers, or other diseases for which reduction of TGFβ family signaling activity is desirable.

In one aspect, the invention features a compound of formula I:

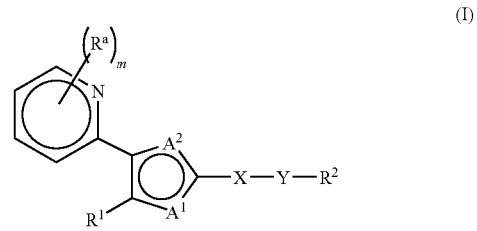

$R^1$ can be aryl, heteroaryl, aralkyl, or heteroaralkyl. Each $R^a$ can be independently alkyl, alkenyl, alkynyl, alkoxy, acyl, halo, hydroxy, amino, nitro, oxo, thioxo, cyano, guanadino, amidino, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl. X can be cycloalkyl or heterocycloalkyl. Y can be a bond, —C(O)—, —C(O)—O—, —O—C(O)—, —S(O)$_p$—, —O—, —O—S(O)$_p$—, —C(O)—N(R$^b$)—, —N(R$^b$)—C(O)—, —O—C(O)—N(R$^b$)—, —N(R$^b$)—C —(O)—O—, —O—S(O)$_p$—N(R$^b$)—, —N(R$^b$)—S(O)$_p$—O—, —N(R$^b$)—C(O)—N(R$^c$)—, —N(R$^b$)—S(O)$_p$—N(R$^c$)—, —C(O)—N(R$^b$)—S(O)$_p$—, —S(O)$_p$—N(R$^b$)—C(O)—, —C(O)—N(R$^b$)—S(O)$_p$—N(R$^c$)—, —C(O)—O—S(O)$_p$—N(R$^b$)—, —N(R$^b$)—S(O)$_p$—N(R$^c$)—C(O)—, —N(R)—S(O)$_p$—O—C(O)—, —S(O)$_p$—N(R$^b$)—, —N(R$^b$)—S(O)$_p$—, —N(R$^b$)—, —S(O)$_p$—, —O—, —S—, or —(C(R$^b$)(R$^c$))$_q$—, wherein each of R$^b$ and R$^c$ is independently hydrogen, hydroxy, alkyl, alkoxy, amino, aryl, aralkyl, heterocycloalkyl, heteroaryl, or heteroaralkyl. p can be 1 or 2, and q can be 1-4. R$^2$ can be hydrogen, alkyl, alkenyl, alkynyl, cycloalkyl, (cycloalkyl)alkyl, cycloalkenyl, (cycloalkenyl)alkyl, aryl, aralkyl, arylalkenyl, heterocycloalkyl, (heterocycloalkyl)alkyl, heterocycloalkenyl, (heterocycloalkenyl)alkyl, heteroaryl, heteroaralkyl, or (heteroaryl)alkenyl. Each of A$^1$ and A$^2$, independently, can be O, S, N, or NR$^b$; provided that at least one of A$^1$ and A$^2$ can be N. m can be 0, 1, 2, or 3, i.e., the 2-pyridyl ring can be unsubstituted or substituted with 1-3 R$^a$ groups. Note that when m≧2, two adjacent R$^a$ groups can join together to form a 4- to 8-membered optionally substituted cyclic moiety. That is, the 2-pyridyl ring can fuse with a cyclic moiety to form a moiety, e.g., 7H-[2]pyrindinyl, 6,7-dihydro-5H-[1]pyrindinyl, 5,6,7,8-tetrahydro-quinolinyl, 5,7-dihydro-furo[3,4-b]pyridinyl, or 3,4-dihydro-1H-thiopyrano[4,3-c]pyridinyl, that can be optionally substituted with one or more substituents such as alkyl (including carboxyalkyl, hydroxyalkyl, and haloalkyl such as trifluoromethyl), alkenyl, alkynyl, cycloalkyl, heterocycloalkyl, alkoxy, aryl, heteroaryl, aryloxy, heteroaryloxy, aroyl, heteroaroyl, amino, nitro, carboxy, alkoxycarbonyl, alkylcarbonyloxy, aminocarbonyl, alkylcarbonylamino, cyano, halo, hydroxy, acyl, mercapto, alkylthio, sulfoxy, sulfamoyl, oxo, or carbamoyl.

In an embodiment, X can be a 4- to 8-membered monocyclic cycloalkyl or heterocycloalkyl, or X can be a 4- to 8-membered bicyclic cycloalkyl or heterocycloalkyl. For example, X can be cyclohexyl, cyclopentyl, piperidinyl, piperazinyl, pyrrolidinyl, tetrahydrofuran, bicyclo[2.2.1]heptane, bicyclo[2.2.2]octane, bicyclo[3.2.1]octane, 2-oxa-bicyclo[2.2.2]octane, 2-aza-bicyclo[2.2.2]octane, 3-aza-bicyclo[3.2.1]octane, or 1-aza-bicyclo[2.2.2]octane.

In an embodiment, X can be piperidinyl, piperazinyl, or pyrrolidinyl; each of which can be bonded to moiety Y via its nitrogen ring atom; and Y can be a bond, —C(O)O—, —C(O)—N(R$^b$)—, —S(O)$_2$—, or —S(O)$_2$—N(R$^b$)—, wherein R$^b$ can be hydrogen or C$_{1-4}$ alkyl.

In an embodiment, X can be cyclohexyl, cyclopentyl, or bicyclo[2.2.2]octane; and Y can be —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, —N(R$^b$)—C(O)—N(R$^c$)—, —C(O)—N(R$^b$)—S(O)$_p$—N(R$^c$)—, or —C(O)—O—S(O)$_p$—N(R$^b$)—. Each of R$^b$, R$^c$, and p has been defined above.

In an embodiment, Y can be —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, —N(R$^b$)—C(O)—N(R$^c$)—, —C(O)—N(R$^b$)—S(O)$_p$—N(R$^c$)—, or —C(O)—O—S(O)$_p$—N(R$^b$)—. Each of R$^b$, R$^c$, and p has been defined above.

In an embodiment, R$^2$ can be hydrogen, C$_{1-6}$ alkyl (e.g., methyl, ethyl, n-butyl, or t-butyl), aryl (e.g., phenyl), heteroaryl (e.g., pyridyl), aryl-C$_{1-4}$ alkyl (e.g., benzyl), or heteroaryl-C$_{1-4}$ alkyl (e.g., pyridylmethyl). In an embodiment, R$^2$ can be C$_{1-4}$ alkyl, phenyl, pyridyl, imidazolyl, furanyl, thienyl, triazolyl, tetrazolyl, benzyl, phenylethyl, benzimidazolyl, benzothiazolyl, naphthylmethyl, naphthylethyl, or —C$_{1-2}$ alkyl-pyridyl (i.e., pyridyl-C$_{1-2}$ alkyl); each of the which can be independently optionally substituted with one or more substituents selected from the group consisting of fluoro, chloro, trifluoromethyl, methyl, ethyl, aminocarbonyl, alkylcarbonylamino, sulfamoyl, alkoxycarbonyl, and alkylcarbonyloxy.

In an embodiment, R$^1$ can be aryl or heteroaryl, e.g., wherein R$^1$ can be a substituted phenyl, an optionally substituted indanyl, or an optionally substituted heteroaryl selected from the group consisting of benzo[1,3]dioxolyl, benzo[b]thiophenyl, benzo-oxadiazolyl, benzothiadiazolyl, benzoimidazolyl, benzooxazolyl, benzothiazolyl, 2-oxo-benzooxazolyl, pyridyl, pyrimidinyl, 2,3-dihydro-benzo[1,4]dioxyl, 2,3-dihydro-benzofuryl, 2,3-dihydro-benzo[b]thiophenyl, 3,4-dihydro-benzo[1,4]oxazinyl, 3-oxo-benzo[1,4]oxazinyl, 1,1-dioxo-2,3-dihydro-benzo[b]thiophenyl, [1,2,4]triazolo[1,5-a]pyridyl, [1,2,4]triazolo[4,3-a]pyridyl, quinolinyl, quinoxalinyl, quinazolinyl, isoquinolinyl, and cinnolinyl.

In an embodiment, m can be 0-2.

In an embodiment, R$^a$ can be C$_{1-4}$ alkyl, C$_{1-4}$ alkoxy, C$_{1-4}$ alkylthio, halo, amino, oxo, aminocarbonyl, or alkoxycarbonyl. In one embodiment, R$^a$ can be substituted at the 6-position.

In an embodiment, A$^1$ can be N and A$^2$ can be NR$^b$, or A$^1$ can be NR$^b$ and A$^2$ can be N; wherein R$^b$ can be hydrogen or C$_{1-4}$ alkyl.

In an embodiment, m can be 0-2; R$^1$ can be aryl or heteroaryl; R$^2$ can be hydrogen, C$_{1-6}$ alkyl, aryl, heteroaryl, —C$_{1-4}$ alkyl-aryl, or —C$_{1-4}$ alkyl-heteroaryl; X can be a 4- to 8-membered monocyclic or bicyclic cycloalkyl or heterocycloalkyl (e.g., piperidinyl, piperazinyl, pyrrolidinyl, tetrahydrofuran, cyclohexyl, cyclopentyl, bicyclo[2.2.1]heptane, bicyclo[2.2.2]octane, bicyclo[3.2.1]octane, 2-oxa-bicyclo[2.2.2]octane, 2-aza-bicyclo[2.2.2]octane, 3-aza-bicyclo[3.2.1]octane, or 1-aza-bicyclo[2.2.2]octane); and Y can be —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, —N(R$^b$)—C(O)—N(R$^c$)—, —C(O)—N(R$^b$)—S(O)$_p$—N(R$^c$)—, or —C(O)—O—S(O)$_p$—N(R$^b$)—.

In an embodiment, m can be 0-2; R$^1$ can be aryl (e.g., substituted phenyl) or heteroaryl; R$^2$ can be hydrogen, C$_{1-6}$ alkyl (e.g., C$_{1-4}$ alkyl), aryl, heteroaryl, —C$_{1-4}$ alkyl-aryl (e.g., benzyl), or —C$_{1-4}$ alkyl-heteroaryl (e.g., pyridylmethyl); X can be cyclohexyl, cyclopentyl, or bicyclo[2.2.2]octane; and Y can be —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, or —N(R$^b$)—C(O)—N(R$^c$)—, —C(O)—N(R$^b$)—S(O)$_p$—N(R$^c$)—, or —C(O)—O—S(O)$_p$—N(R$^b$)—, wherein each of R$^b$ and R$^c$ can independently be hydrogen or C$_{1-4}$ alkyl; A$^1$ can be N and A$^2$ can be NH, or A$^1$ can be NH and A$^2$ can be N; m can be 1; and R$^a$ can be substituted at the 6-position. For compounds of formula (I) wherein m is 1, R$^a$ can be generally substituted at the 6-position.

In an embodiment, m can be 0-2; R$^1$ can be aryl (e.g., substituted phenyl) or heteroaryl; R$^2$ can be hydrogen, C$_{1-6}$ alkyl (e.g., C$_{1-4}$ alkyl), aryl, heteroaryl, —C$_{1-4}$ alkyl-aryl (e.g., benzyl), or —C$_{1-4}$ alkyl-heteroaryl (e.g., pyridylmethyl); —X—Y— can be

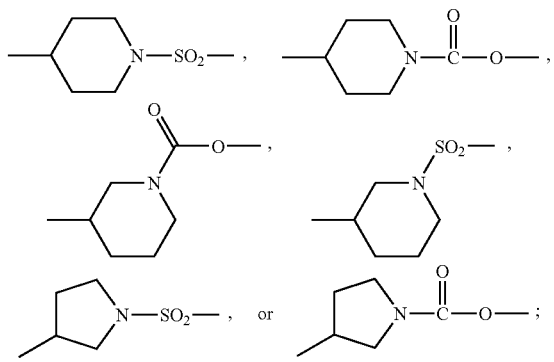

$A^1$ can be N and $A^2$ can be NH, or $A^1$ can be NH and $A^2$ can be N; m can be 1; and $R^a$ can be substituted at the 6-position.

Some examples of a compound of formula (I) are shown in Examples 5-215 below.

An N-oxide derivative or a pharmaceutically acceptable salt of each of the compounds of formula (I) is also within the scope of this invention. For example, a nitrogen ring atom of the imidazole core ring or a nitrogen-containing heterocyclyl substituent can form an oxide in the presence of a suitable oxidizing agent such as m-chloroperbenzoic acid or $H_2O_2$.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such acids include hydrochloric acid, hydrobromic acid, hydroiodic acid, sulfuric acid, methanesulfonic acid, phosphoric acid, p-bromophenyl-sulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to those skilled in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Compounds of formula (I) can also be, e.g., in a form of achiral compounds, racemic mixtures, optically active compounds, pure diastereomers, or a mixture of diastereomers.

Compounds of formula (I) exhibit surprisingly high affinity to the TGFβ family type I receptors, Alk 5 and/or Alk 4, e.g., with $IC_{50}$ and $K_i$ values of less than 10 μM under conditions as described below in Examples 215 and 217, respectively. Some compounds of formula (I) exhibit $IC_{50}$ and $K_i$ values of less than 1 μM (such as below 50 nM).

Compounds of formula (I) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

The present invention also features a pharmaceutical composition comprising a compound of formula (I) (or a combination of two or more compounds of formula (I)) and at least one pharmaceutically acceptable carrier. Also included in the present invention is a medicament composition including any of the compounds of formula (I), alone or in a combination, together with a suitable excipient.

The invention also features a method of inhibiting the TGFβ family type I receptors, Alk 5 and/or Alk 4 (e.g., with an $IC_{50}$ value of less than 10 μM; such as, less than 1 μM; and for example, less than 5 nM) in a cell, including the step of contacting the cell with an effective amount of one or more compounds of formula (I). Also within the scope of the invention is a method of inhibiting the TGFβ and/or activin signaling pathway in a cell or in a subject (e.g., a mammal such as a human), including the step of contacting the cell with or administering to the subject an effective amount of one or more of the compounds of formula (I).

Also within the scope of the present invention is a method of treating a subject or preventing a subject from suffering a condition characterized by or resulting from an elevated level of TGFβ and/or activin activity. The method includes the step of administering to the subject an effective amount of one or more of the compounds of formula (I). The conditions include, for example, an accumulation of excess extracellular matrix; a fibrotic condition (e.g., glomerulonephritis, diabetic nephropathy, hypertensive nephropathy, lupus nephropathy or nephritis, hepatitis-induced cirrhosis, biliary fibrosis, scleroderma, pulmonary fibrosis, post-infarction cardiac fibrosis, fibrosclerosis, fibrotic cancers, fibroids, fibroma, fibroadenomas, or fibrosarcomas); TGFβ-induced metastasis of tumor cells; and carcinomas (e.g, carcinomas of the lung, breast, liver, biliary tract, gastrointestinal tract, head and neck, pancreas, prostate, cervix as well as multiple myeloma, melanoma, glioma, or glioblastomas).

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as alkoxy, cycloalkyloxy, heterocycloalkyloxy, aryloxy, heteroaryloxy, aralkyloxy, heteroarylalkoxy, amino, nitro, carboxy, cyano, halo, hydroxy, sulfo, mercapto, alkylsulfanyl, alkylsulfinyl, alkylsulfonyl, aminocarbonyl, alkylcarbonylamino, cycloalkylcarbonylamino, cycloalkyl-alkylcarbonylamino, arylcarbonylamino, aralkylcarbonylamino, heterocycloalkyl-carbonylamino, heterocycloalkyl-alkylcarbonylamino, heteroaralkylcarbonylamino, heteroaralkylcarbonylamino, urea, thiourea, sulfamoyl, sulfamide, alkoxycarbonyl, or alkylcarbonyloxy.

As used herein, an "amino" group refers to $-NR^XR^Y$ wherein each of $R^X$ and $R^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl. When the term "amino" is not the terminal group (e.g., alkylcarbonylamino), it is represented by $-NR^X-$. $R^X$ has the same meaning as defined above.

As used herein, an "aryl" group refers to phenyl, naphthyl, or a benzofused group having 2 to 3 rings. For example, a benzofused group includes phenyl fused with one or two $C_{4-8}$ carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl.

As used herein, a "cycloalkyl" group refers to an aliphatic carbocyclic ring of 3-10 (e.g., 4-8) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.2.3]nonyl,. A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl,. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, a "heterocycloalkyl" group refers to a 3- to 10-membered (e.g., 4- to 8-membered) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.0$^{3,7}$] nonyl. A "heterocycloalkenyl" group, as used herein, refers to a 3- to 10-membered (e.g., 4- to 8-membered) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

A "heteroaryl" group, as used herein, refers to a monocyclic, bicyclic, or tricyclic ring structure having 5 to 15 ring atoms wherein one or more of the ring atoms is a heteroatom, e.g., N, O, or S and wherein one ore more rings of the bicyclic or tricyclic ring structure is aromatic. Some examples of heteroaryl are pyridyl, furyl, pyrrolyl, thienyl, thiazolyl, oxazolyl, imidazolyl, indolyl, tetrazolyl, benzofuryl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—$NR^xR^y$ or —$NR^x$—CO—O—$R^z$ wherein $R^x$ and $R^y$ have been defined above and $R^z$ can be alkyl, aryl, aralkyl, heterocycloalkyl, heteroaryl, or heteroaralkyl.

As used herein, a "carboxy" and a "sulfo" group refer to —COOH and —$SO_3H$, respectively.

As used herein, an "alkoxy" group refers to an alkyl-O— group where "alkyl" has been defined previously.

As used herein, a "sulfoxy" group refers to —O—SO—$R^X$ or —SO—O—$R^X$, where $R^X$ has been defined above.

As used herein, a "halogen" or "halo" group refers to fluorine, chlorine, bromine or iodine.

As used herein, a "sulfamoyl" group refers to the structure —$S(O)_2$—$NR^xR^y$ or —$NR^x$—$S(O)_2$—$R^z$ wherein $R^x$, $R^y$, and $R^z$ have been defined above.

As used herein, a "sulfamide" group refers to the structure —$NR^X$—$S(O)_2$—$NR^YR^Z$ wherein $R^X$, $R^Y$, and $R^Z$ have been defined above.

As used herein, a "urea" group refers to the structure —$NR^X$—CO—$NR^YR^Z$ and a "thiourea" group refers to the structure —$NR^X$—CS—$NR^YR^Z$. $R^X$, $R^Y$, and $R^Z$ have been defined above.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

An antagonist, as used herein, is a molecule that binds to the receptor without activating the receptor. It competes with the endogenous ligand(s) or substrate(s) for binding site(s) on the receptor and, thus inhibits the ability of the receptor to transduce an intracellular signal in response to endogenous ligand binding.

As compounds of formula (I) are antagonists of TGFβ receptor type I (Alk5) and/or activin receptor type I (Alk4), these compounds are useful in inhibiting the consequences of TGFβ and/or activin signal transduction such as the production of extracellular matrix (e.g., collagen and fibronectin), the differentiation of stromal cells to myofibroblasts, and the stimulation of and migration of inflammatory cells. Thus, compounds of formula (I) inhibit pathological inflammatory and fibrotic responses and possess the therapeutic utility of treating and/or preventing disorders or diseases for which reduction of TGFβ and/or activin activity is desirable (e.g., various types of fibrosis or progressive cancers). In addition, the compounds of formula (I) are useful for studying and researching the role of TGFβ receptor type I (Alk5) and/or activin receptor type I (Alk4), such as their role in cellular processes, for example, signal transduction, production of extracellular matrix, the differentiation of stromal cells to myofibroblasts, and the stimulation of and migration of inflammatory cells.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods, and examples are illustrative only and not intended to be limiting.

Other features and advantages of the invention will be apparent from the following detailed description, and from the claims.

DETAILED DESCRIPTION OF THE INVENTION

In general, the invention features compounds of formula (I), which exhibit surprisingly high affinitiy for the TGFβ family type I receptors, Alk 5 and/or Alk 4.

Synthesis of the Compounds of Formula (I)

Compounds of formula (I) may be prepared by a number of known methods from commercially available or known starting materials. In one method, compounds of formula (I) wherein $A^1$ is N and $A^2$ is NH, or $A^1$ is NH and $A^2$ is N are prepared according to Scheme 1a or Scheme 1b below. Specifically, in Scheme 1a, optionally substituted 2-methylpyridine (II) is deprotonated by LDA before reacting with $R^1$-substituted carboxylic acid methoxy-methyl-amide (V) to form an $R^1$-(6-methylpyridyl)-ketone (III). $R^1$ has been defined above. See Example 3B below. The methoxy-methyl-amide can be prepared by reacting a corresponding acid chloride (i.e., $R^1$—CO—Cl) with N,O-dimethylhydroxylamine hydrochloride. See Example 2 below. The $R^1$-(6-methylpyridyl)-ketone (III) can then be treated with sodium nitrite in acetic acid to afford an α-keto-oxime (IV), which can undergo further reaction with an appropriate substituted (and optionally protected) aldehyde (VI) in the presence of ammonium acetate to yield a compound of formula (I).

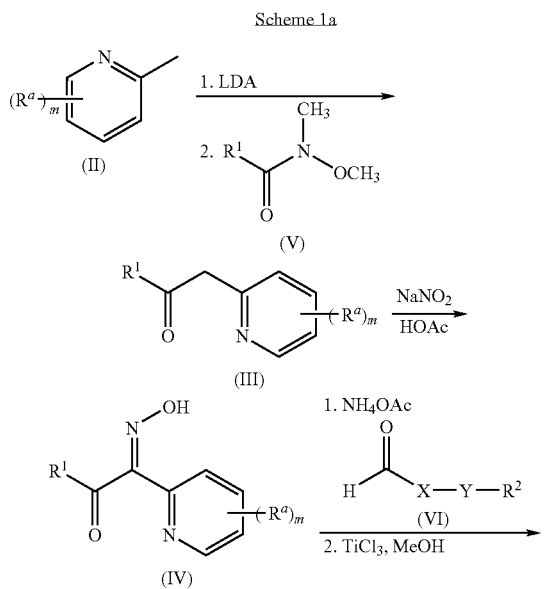

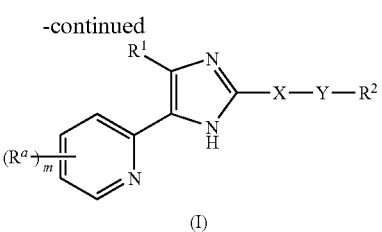

(I)

In another method, the above-described compounds of formula (I) can be prepared according to Scheme 1b below. Specifically, $R^1$-substituted pyridine-2-carbaldehyde (IIa) is first reacted with aniline and diphenyl phosphite to form a resulting N,P-acetal, which can further couple with an $R^1$-substituted aldehyde to produced an ($R^1$-methyl)-pyridyl-ketone (IIIa). See, e.g., Journet et al., *Tetrahedron Lett.* 39:1717-1720 (1998) and Example 3C below. Treatment of the ($R^1$-methyl)-pyridyl-ketone (IIIa) with sodium nitrite in acetic acid produces an α-keto-oxime (IVa), which can undergo reaction with an appropriate substituted (and optionally protected) aldehyde (VI) to yield a compound of formula (I) as described in Scheme 1a above.

If compound (VI) is in its protected form, appropriate deprotecting agents can be applied to the resulting compound after the coupling reaction of compound (IV) or (IVa) and compound (VI) to yield a compound of formula (I). See, e.g., T. W. Greene, *Protective Groups in Organic Synthesis*, John Wiley & Sons, Inc., New York (1981), for suitable protecting groups.

Alternatively, a compound of formula (I) can be prepared by reacting intermediate (IV) or (IVa) with an aldehyde (VII) to yield a further intermediate (VIII), which can then react with compound (IX) to yield a compound of formula (I). Note that moieties Y' and Y" are precursors of moiety Y. See Scheme 2 below. In addition, desired substitutions at $R^a$ can be obtained by selecting, for example, the appropriate compound (IIa) intermediate. See, e.g., Example 3A below.

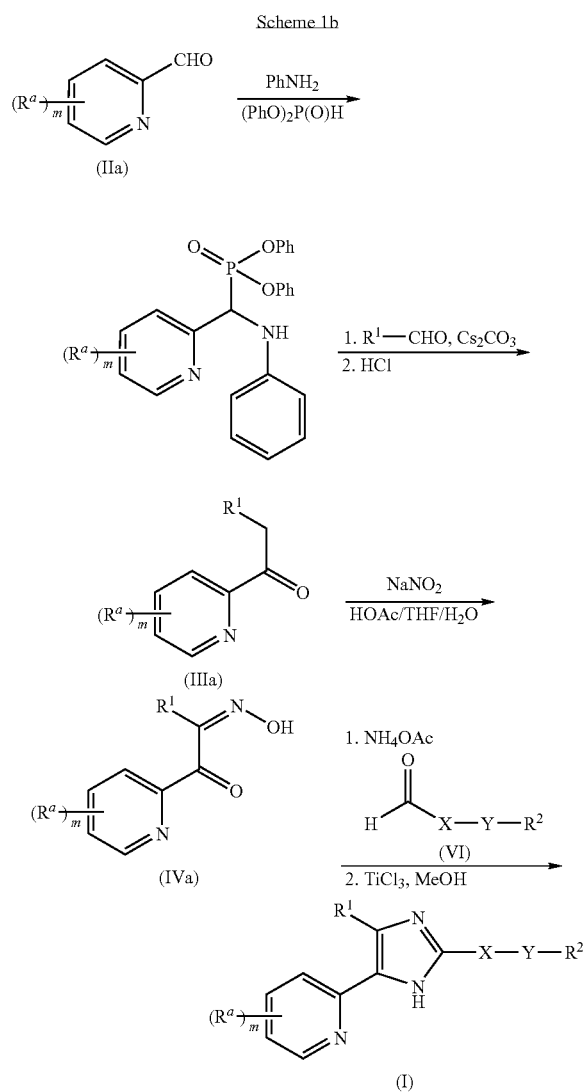

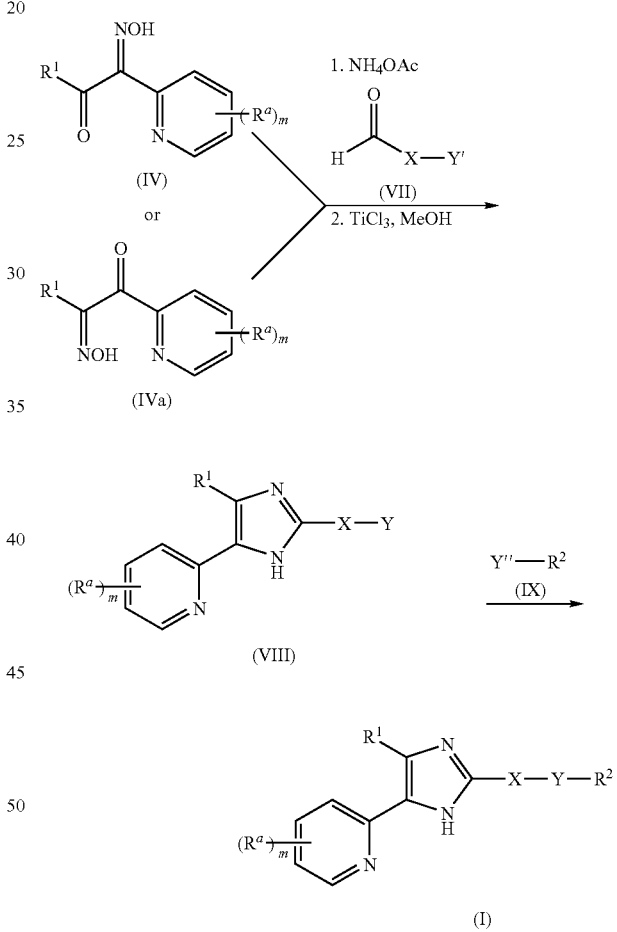

In some embodiments, moiety X in compound (VII) is a nitrogen-containing heterocycloalkyl (e.g., piperidine). The nitrogen ring atom can be protected by a nitrogen protecting group (e.g., Cbz, Boc, or FMOC) before coupling to compound (IV) or (IVa) and deprotected afterwards (see first step of Scheme 3) to yield compound (VIIIa). This compound can further react with various compounds (IX) to produce a compound of formula (I). See second steps of Scheme 3 below. It should be noted that compound (VIII) or compound (VIIIa) can be a compound of formula (I) as well.

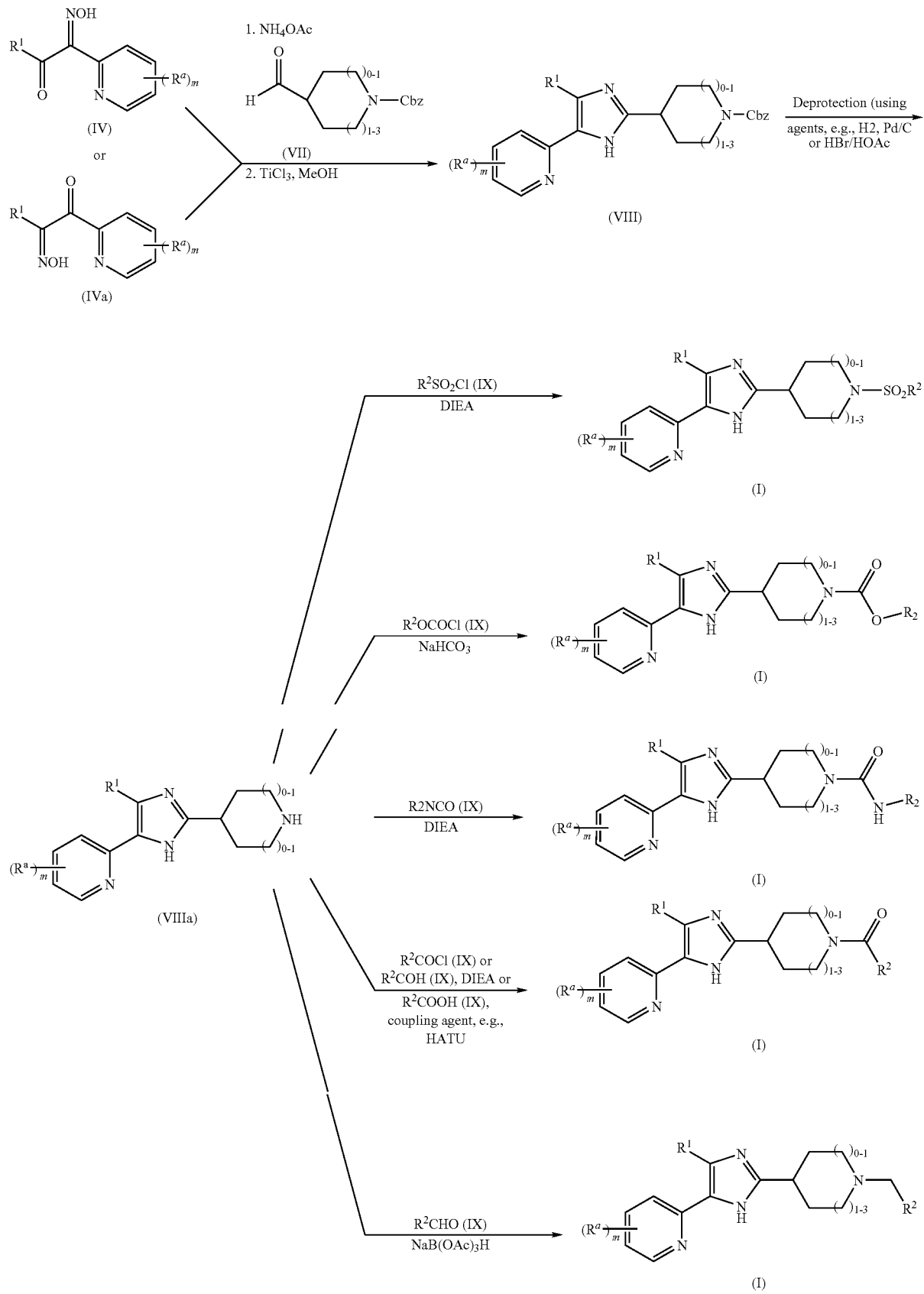
Scheme 3

Similarly, when moiety X in compound (VII) is a cycloalkyl (e.g., cyclopentyl, cyclohexyl, or bicyclo[2.2.2] octane), it can be further functionalized to form a compound of formula (I) as depicted in Schemes 4, 5a, 5b, and 5c below.
Scheme 4
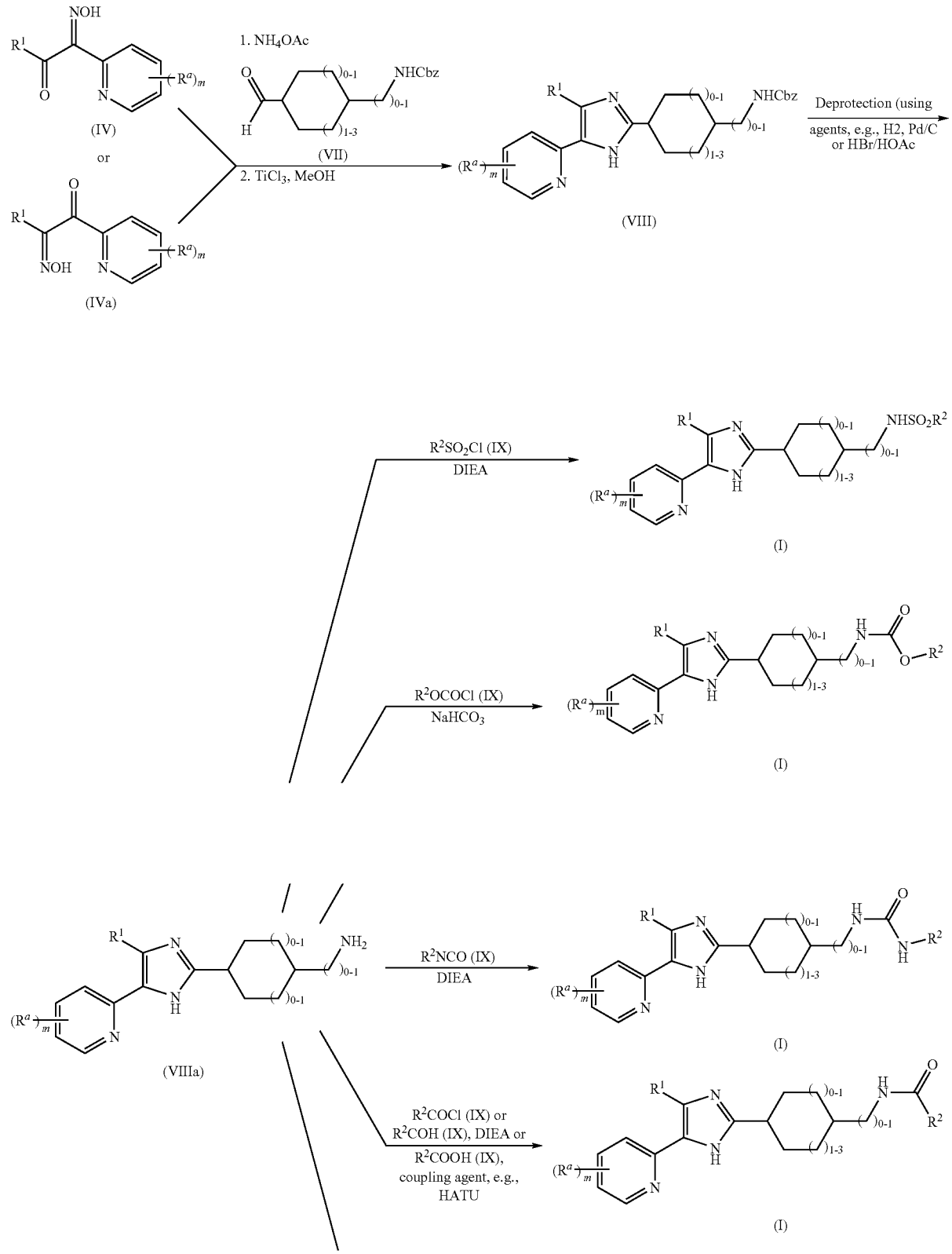

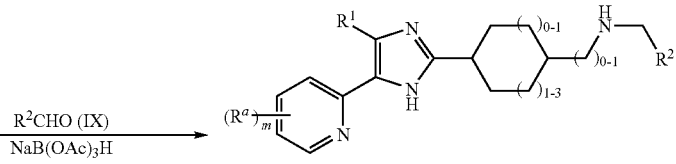
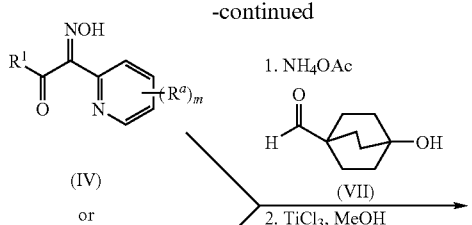
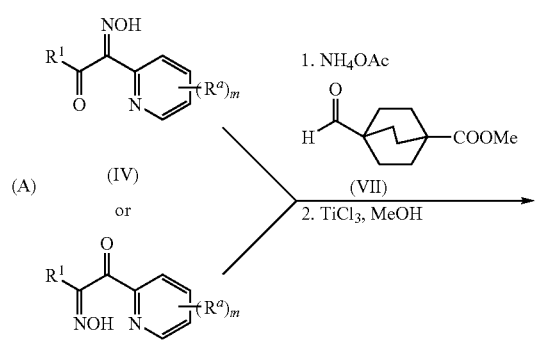
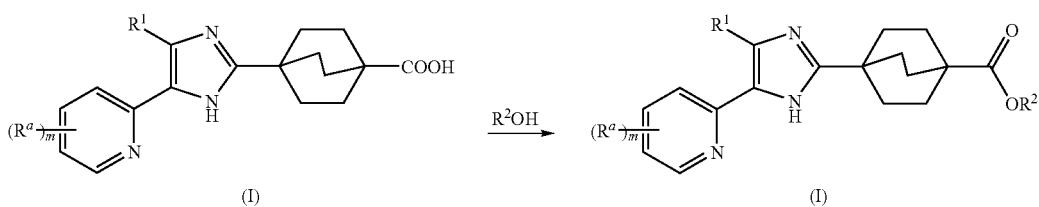

-continued
(2)
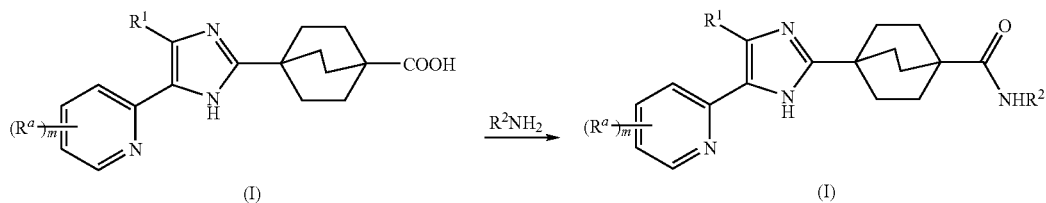
(3)
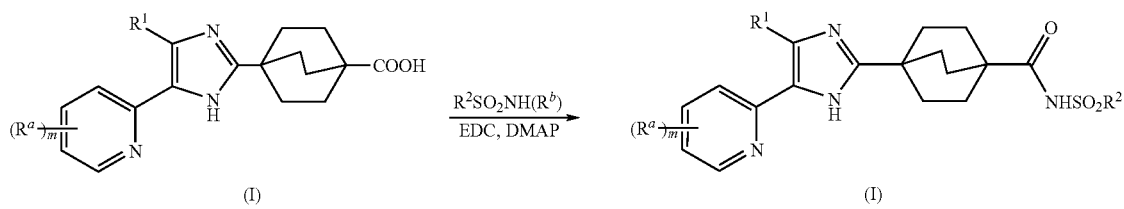
(4)
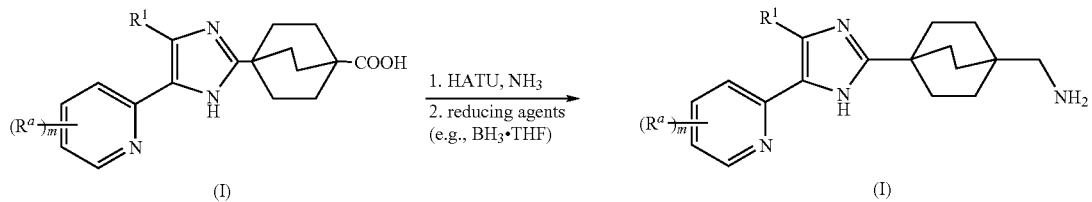
(can be further modified according to Scheme 5c below)
(5)
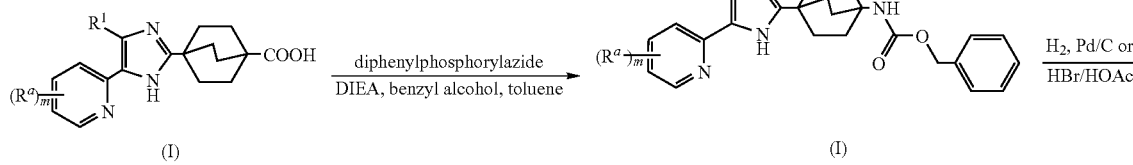
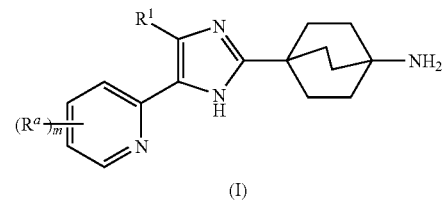
(can be further modified according to scheme 5c below)
(6)
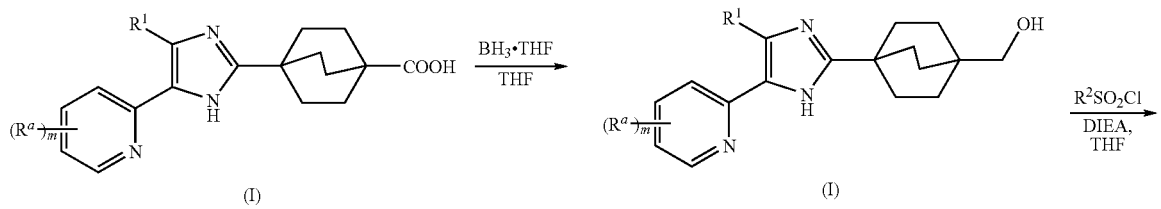

-continued
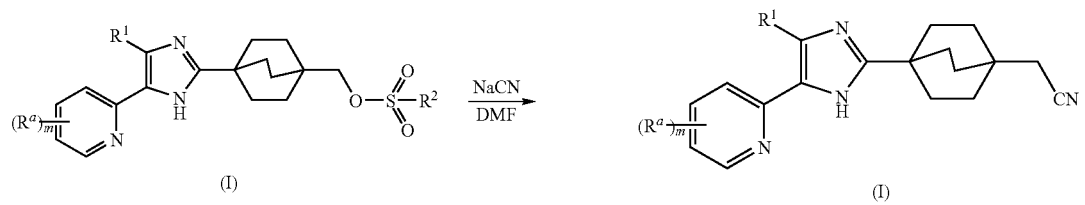
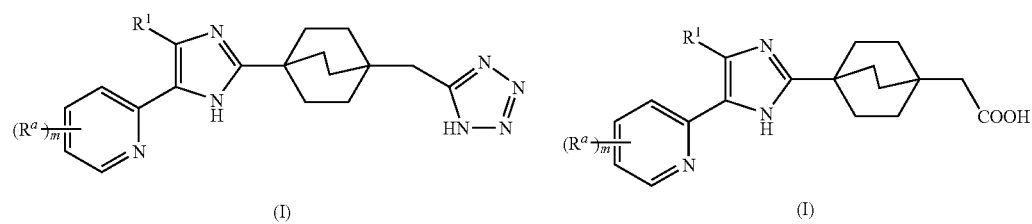
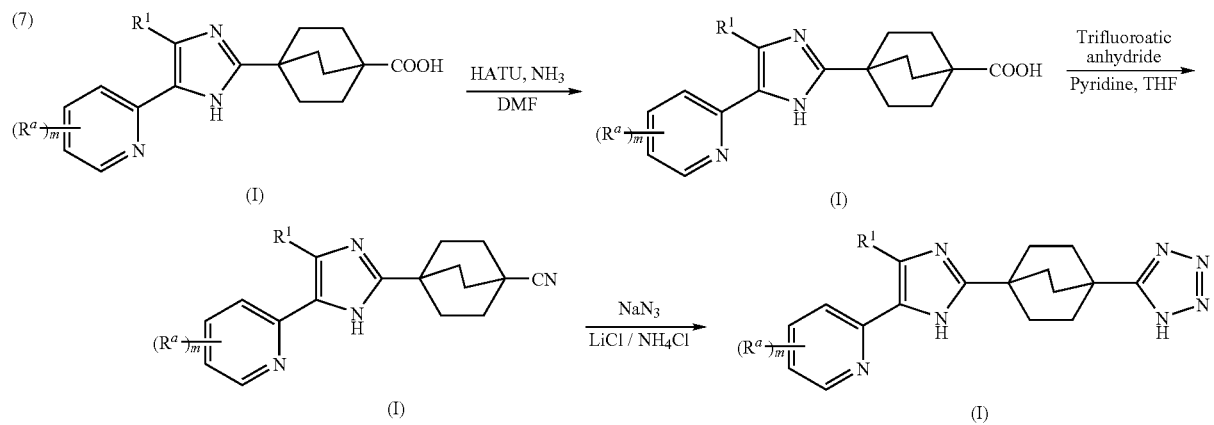
Scheme 5c
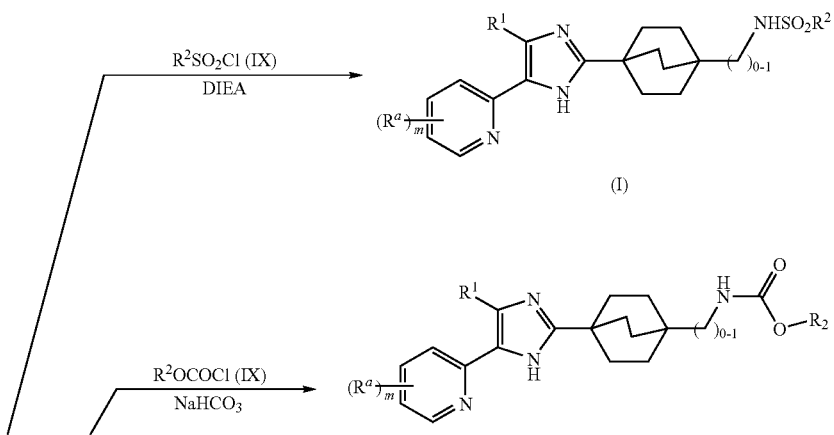

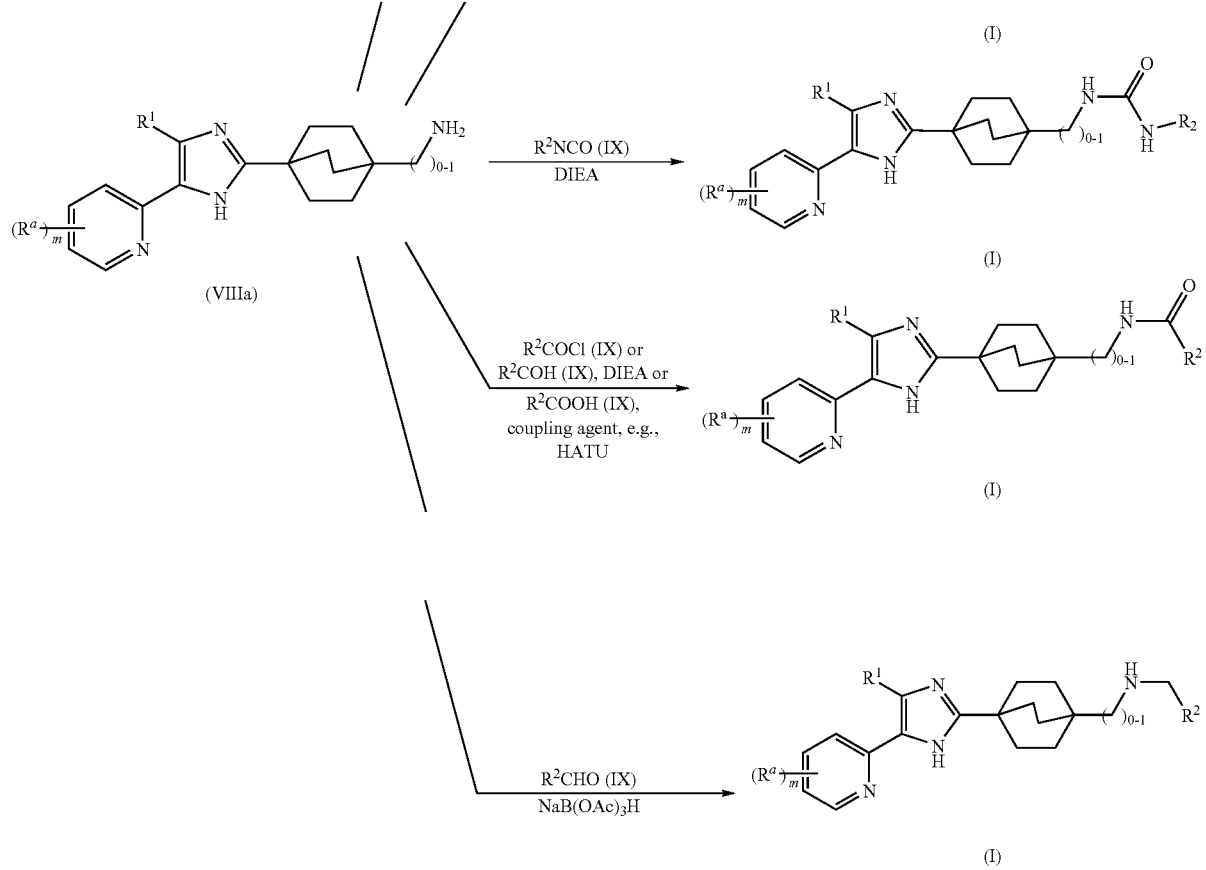

Compound of formula (I) wherein $A^1$ is N and $A^2$ is $NR^b$ (or $A^1$ is $NR^b$ and $A^2$ is N) can be prepared by known methods. For example, compounds of formula (I) with an unsubstituted imidazolyl core ring can be treated with $R^bI$ and $CsCO_3$ to produce a compound of formula (I) having a substituted imidazolyl core ring. See, e.g., Liverton, et al., *J. Med. Chem.*, 42: 2180-2190 (1999).

Compounds of formula (I) wherein $A^1$ is O and $A^2$ is NH (or $A^1$ is NH and $A^2$ is O) or wherein $A^1$ is S and $A^2$ is NH (or $A^1$ is NH and $A^2$ is S), can be prepared according to known methods. One of these methods employs the same intermediate (III) or (IIIa) as described above. See, e.g., Revesz, et al., *Bioorg. & Med. Chem. Lett.* 10: 1261-1264 (2000) and Scheme 6 below.

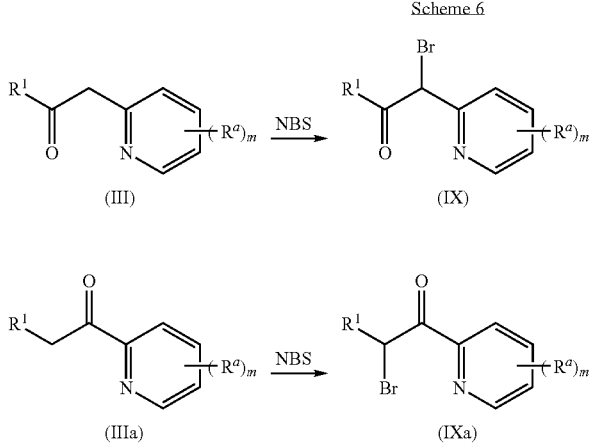

Scheme 6

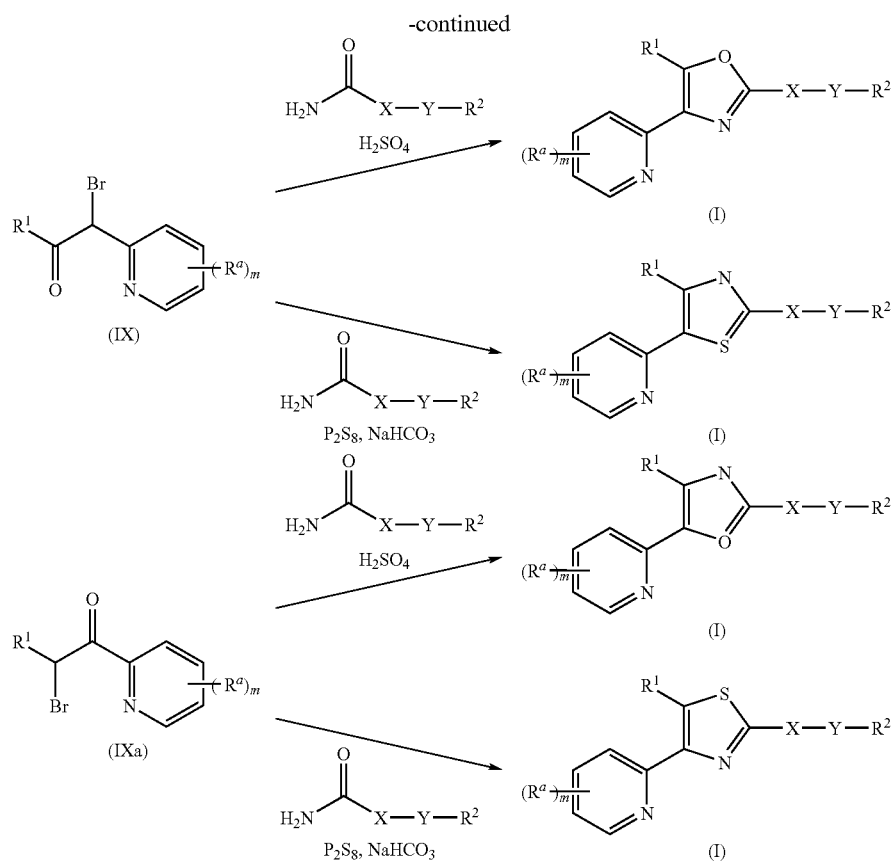

As is well known to a skilled person in chemistry, desired substitutions can be placed on the 2-pyridyl ring in the last step of the synthesis. See, e.g., Example 24 below.

Uses of Compounds of Formula (I)

As discussed above, hyperactivity of the TGFβ family signaling pathways can result in excess deposition of extracellular matrix and increased inflammatory responses, which can then lead to fibrosis in tissues and organs (e.g., lung, kidney, and liver) and ultimately result in organ failure. See, e.g., Border, W. A. and Ruoslahti E. *J. Clin. Invest.* 90: 1-7 (1992) and Border, W. A. and Noble, N. A. *N. Engl. J. Med.* 331: 1286-1292 (1994). Studies have been shown that the expression of TGFβ and/or activin mRNA and the level of TGFβ and/or activin are increased in patients suffering from various fibrotic disorders, e.g., fibrotic kidney diseases, alcohol-induced and autoimmune hepatic fibrosis, myelofibrosis, bleomycin-induced pulmonary fibrosis, and idiopathic pulmonary fibrosis.

Compounds of formula (I), which are antagonists of the TGFβ family type I receptors Alk 5 and/or Alk 4, and inhibit TGFβ and/or activin signaling pathway, are therefore useful for treating and/or preventing fibrotic disorders or diseases mediated by an increased level of TGFβ and/or activin activity. As used herein, a compound inhibits the TGFβ family signaling pathway when it binds (e.g., with an $IC_{50}$ value of less than 10 μM; such as, less than 1 μM; and for example, less than 5 nM) to a receptor of the pathway (e.g., Alk 5 and/or Alk 4), thereby competing with the endogenous ligand(s) or substrate(s) for binding site(s) on the receptor and reducing the ability of the receptor to transduce an intracellular signal in response to the endogenous ligand or substrate binding. The aforementioned disorders or diseases include any condition (a) marked by the presence of an abnormally high level of TGFβ and/or activin; and/or (b) an excess accumulation of extracellular matrix; and/or (c) an increased number and synthetic activity of myofibroblasts. These disorders or diseases include, but are not limited to, fibrotic conditions such as scleroderma, idiopathic pulmonary fibrosis, glomerulonephritis, diabetic nephropathy, lupus nephritis, hypertension-induced nephropathy, ocular or corneal scarring, hepatic or biliary fibrosis, acute lung injury, pulmonary fibrosis, post-infarction cardiac fibrosis, fibrosclerosis, fibrotic cancers, fibroids, fibroma, fibroadenomas, and fibrosarcomas. Other fibrotic conditions for which preventive treatment with compounds of formula (I) can have therapeutic utility include radiation therapy-induced fibrosis, chemotherapy-induced fibrosis, and surgically induced scarring including surgical adhesions, laminectomy, and coronary restenosis.

Increased TGFβ activity is also found to manifest in patients with progressive cancers. Studies have shown that in late stages of various cancers, both the tumor cells and the stromal cells within the tumors generally overexpress TGFβ. This leads to stimulation of angiogenesis and cell motility, suppression of the immune system, and increased interaction of tumor cells with the extracellular matrix. See, e.g., Hojo, M. et al., *Nature* 397: 530-534 (1999). As a result, the tumor cells become more invasive and metastasize to distant organs. See, e.g., Maehara, Y. et al., *J. Clin. Oncol.* 17: 607-614 (1999) and Picon, A. et al., *Cancer Epidemiol. Biomarkers Prev.* 7: 497-504 (1998). Thus, compounds of formula (I), which are antagonists of the TGFβ type I receptor and inhibit TGFβ signaling pathways, are also useful for treating and/or preventing various late stage cancers which overexpress TGFβ. Such late stage cancers include carcinomas of the lung, breast, liver, biliary tract, gastrointestinal tract, head and neck, pancreas, prostate, cervix as well as multiple myeloma, melanoma, glioma, and glioblastomas.

Importantly, it should be pointed out that because of the chronic, and in some cases localized, nature of disorders or diseases mediated by overexpression of TGFβ and/or activin (e.g., fibrosis or cancers), small molecule treatments (such as treatment disclosed in the present invention) are favored for long-term treatment.

Not only are compounds of formula (I) useful in treating disorders or diseases mediated by high levels of TGFβ and/or activin activity, these compounds can also be used to prevent the same disorders or diseases. It is known that polymorphisms leading to increased TGFβ and/or activin production have been associated with fibrosis and hypertension. Indeed, high serum TGFβ levels are correlated with the development of fibrosis in patients with breast cancer who have received radiation therapy, chronic graft-versus-host-disease, idiopathic interstitial pneumonitis, veno-occlusive disease in transplant recipients, and peritoneal fibrosis in patients undergoing continuous ambulatory peritoneal dialysis. Thus, the levels of TGFβ and/or activin in serum and of TGFβ and/or activin mRNA in tissue can be measured and used as diagnostic or prognostic markers for disorders or diseases mediated by overexpression of TGFβ and/or activin, and polymorphisms in the gene for TGFβ that determine the production of TGFβ and/or activin can also be used in predicting susceptibility to disorders or diseases. See, e.g., Blobe, G. C. et al., *N. Engl. J. Med.* 342(18): 1350-1358 (2000); Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al, *Am. J. Pathol.* 148: 707-713 (1996); De Bleser et al., *Hepatology* 26: 905-912 (1997); Pawlowski, J. E., et al., *J. Clin. Invest.* 100: 639-648 (1997); and Sugiyama, M. et al., *Gastroenterology* 114: 550-558 (1998).

Administration of Compounds of Formula (I)

As defined above, an effective amount is the amount required to confer a therapeutic effect on the treated patient. For a compound of formula (I), an effective amount can range, for example, from about 1 mg/kg to about 150 mg/kg (e.g., from about 1 mg/kg to about 100 mg/kg). Effective doses will also vary, as recognized by those skilled in the art, dependant on route of administration, excipient usage, and the possibility of co-usage with other therapeutic treatments including use of other therapeutic agents and/or radiation therapy.

Compounds of formula (I) can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The pharmaceutically acceptable compositions include aqueous solutions of the active agent, in an isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds. As to route of administration, the compositions can be administered orally, intranasally, transdermally, intradermally, vaginally, intraaurally, intraocularly, buccally, rectally, transmucosally, or via inhalation, implantation (e.g., surgically), or intravenous administration. The compositions can be administered to an animal (e.g., a mammal such as a human, non-human primate, horse, dog, cow, pig, sheep, goat, cat, mouse, rat, guinea pig, rabbit, hamster, gerbil, or ferret, or a bird, or a reptile, such as a lizard).

Optionally, compounds of formula (I) can be administered in conjunction with one or more other agents that inhibit the TGFβ signaling pathway or treat the corresponding pathological disorders (e.g., fibrosis or progressive cancers) by way of a different mechanism of action. Examples of these agents include angiotensin converting enzyme inhibitors, nonsteroid and steroid anti-inflammatory agents, as well as agents that antagonize ligand binding or activation of the TGFβ receptors, e.g., anti-TGFβ, anti-TGFβ receptor antibodies, or antagonists of the TGFβ type II receptors.

The invention will be further described in the following examples, which do not limit the scope of the invention described in the claims.

Synthesis of exemplary intermediates (IIa), (III), (IIIa), (IV), (V), and (VII) are described in Examples 1-4 below.

EXAMPLE 1

(4-Formyl-cyclohexyl)-carbamic acid benzyl ester (VII)

Synthesis of the title compound is described in parts (a)-(c) below.

(a)
4-Benzyloxycarbonylamino-cyclohexanecarboxylic acid

Benzyl chloroformate (2.2 mL, 15.4 mmol) was added to a solution of 4-amino-cyclohexanecarboxylic acid (2 g, 14.0 mmol) in a mixture of 1,4-dioxane (5 mL) and saturated sodium bicarbonate aqueous solution (5 mL). The mixture was stirred at 0° C. for 3 hours. Dioxane was removed under reduced pressure. The residue was partitioned between ethyl acetate and water. The ethyl acetate solution was washed with brine, dried over sodium sulfate, filtered, and concentrated to give 2.3 g (59%) of 4-benzyloxycarbonylamino-cyclohexanecarboxylic acid as yellow oil. MS (ESP−) m/z 276.39 (M−1). $^1$H NMR (300 MHz, CDCl$_3$) δ 7.34 (m, 5H), 5.09 (s, 2H), 2.24 (m, 1H), 2.04 (m, 2H), 1.83 (m, 2H), 1.44 (m, 3H), 0.97 (m, 2H).

(b) (4-(Methoxy-methyl-carbamoyl)-cyclohexyl)-carbamic acid benzyl ester

Oxalyl chloride (0.796 mL, 9.1 mmol) was added slowly to a solution of 4-benzyloxycarbonylamino-cyclohexanecarboxylic acid (2.3 g, 8.3 mmil) in dichloromethane (20 mL). The mixture was stirred at room temperature under nitrogen for 1 hour. Solvent was removed under reduced pressure. N,O-Dimethylhydroxylamine hydrochloride (0.971 g, 9.96 mmol) in anhydrous pyridine (10 mL) was added to the reaction residue. The mixture was stirred at room temperature for 3 hours. Solvent was removed under reduced pressure, and the residue was partitioned between ethyl acetate and water. Ethyl acetate solution was washed with brine, dried over sodium sulfate, filtered, and concentrated to give 1.0 g (38%) of (4-(methoxy-methyl-carbamoyl)-cyclohexyl)-carbamic acid benzyl ester as yellow oil. $^1$H NMR (400 MHz, CDCl$_3$)

δ 7.36 (m, 5H), 4.59 (s, 2H), 3.88 (m, 1H), 3.70 (s, 3H), 3.17 (s, 3H), 2.76 (m, 1H), 1.86 (m, 2H), 1.66 (m, 6H).

(c) (4-Formyl-cyclohexyl)-carbamic acid benzyl ester

Diisobutylaluminum hydride (1.0 M solution, 6.24 mL, 6.24 mmol) was added slowly to a solution of (4-(methoxy-methyl-carbamoyl)-cyclohexyl)-carbamic acid benzyl ester (1.0 g, 3.12 mmol) in anhydrous THF (20 mL) at −78° C. The mixture was stirred at −78° C. for 1 hour. Water (2 mL) was added at 0° C. The mixture was partitioned between ethyl acetate and water. Ethyl acetate was washed with brine, dried over sodium sulfate, filtered and concentrated to give 0.60 g (74%) of (4-formyl-cyclohexyl)-carbamic acid benzyl ester as a yellow oil. $^1$H NMR (400 MHz, CDCl$_3$) δ 9.66 (s, 1H), 7.36 (5H), 3.63 (m, 1H), 2.38 (m, 1H), 1.77 (m, 4H), 1.18 (m, 4H).

EXAMPLE 2

Benzo[1,3]dioxole-5-carboxylic acid methoxy-methyl-amide (V)

Sodium hydroxide (12.0 g, 300 mmol) in water (15 mL) was added slowly to a solution of piperonyl chloride (5.55 g, 30 mmol) and N,O-dimethylhydroxylamine hydrochloride (3.53 g, 36 mmol) in acetonitrile (200 mL). The mixture was stirred at room temperature for 0.5 h. Acetonitrile was removed under reduced pressure, and the residue was partitioned between ethyl acetate and water. The organic layer was washed with brine, dried over sodium sulfate, filtered, and concentrated. Column chromatography on silica gel eluting with ethyl acetate:hexanes (30:70) gave 5.5 g (88%) of the title compound as a yellow oil. MS (ES$^+$) m/z 210.1 (M+1). $^1$H NMR (400 MHz, CDCl$_3$) δ 7.34 (m, 1H), 7.26 (d, 1H, J=1.3 Hz), 6.86 (d, 1H, J=8.1 Hz), 6.05 (s, 2H), 3.61 (s, 3H), 3.38 (s, 3H).

EXAMPLE 3A

6-Cyclopropyl-pyridine-2-carbaldehyde (IIa)

Synthesis of the title compound is described in parts (a)-(c) below.

(a) 2-Bromo-6-[1,3]dioxolan-2-yl-pyridine

A mixture of 6-bromo-pyridine-2-carbaldehyde (2.0 g, 10.75 mmol), ethylene glycol (3 mL, 53.75 mmol), and a catalytic amount of TsOH in toluene (50 mL) was heated to reflux with a Dean-Stark trap for 1.5 hours and cooled down to room temperature and concentrated in vacuo. The residue was purified on silica gel column with 2% EtOAc in CH$_2$Cl$_2$ to yield 2-bromo-6-[1,3]dioxolan-2-yl-pyridine as a colorless liquid (1.97 g, 80%).

(b) 2-Cyclopropyl-6-[1,3]dioxolan-2-yl-pyridine

To a solution of ZnCl$_2$ in THF (0.5 M, 25 mL) was added dropwise a solution of cyclopropylmagnesium bromide (0.5 M, 25 mL) at −78° C. under nitrogen. The reaction mixture was then allowed to warm up to room temperature and stirred for an hour. The above mixture was then transferred to a sealed tube with 2-bromo-6-[1,3]dioxolan-2-yl-pyridine (1.9 g, 8.25 mmole, see subpart (a) above) and Pd(PPh$_3$)$_4$ (0.4 g, 0.35 mmole). TLC showed major formation of the product and some starting material. The mixture was then heated to 120° C. for 2 hours and cooled down to room temperature and then worked up with EtOAc and saturated ammonium chloride and dried over MgSO$_4$. The residue from concentration was purified on silica gel column with 5% EtOAc in CH$_2$Cl$_2$ to yield 2-cyclopropyl-6-[1,3]dioxolan-2-yl-pyridine as a bright yellow liquid (0.96 g, 61%).

(c) 6-Cyclopropyl-pyridine-2-carbaldehyde

A mixture of 2-cyclopropyl-6-[1,3]dioxolan-2-yl-pyridine (0.9 g, see subpart (b) above) and a catalytic amount of TsOH hydrate in a mixture of acetone (10 mL) and water (2 mL) was heated to reflux overnight until most of the starting materials were consumed according to TLC. It was then cooled down to room temperature and concentrated. The residue was dissolved in diethyl ether and washed with saturated sodium carbonate, and then water, and then dried over MgSO$_4$ and concentrated. The concentrate was purified on silica gel column with 100% CH$_2$Cl$_2$ to yield 6-cyclopropyl-pyridine-2-carbaldehyde as a bright liquid (0.65 g, 94%). $^1$H NMR (CDCl$_3$, 300 MHz), δ 9.90 (s, 1H), 7.58 (m, 2H), 7.23 (m, 1H), 2.01 (m, 1H), 1.02-0.92 (m, 4H).

The titled aldehyde was converted to the corresponding N,P-acetal for ketone preparation according to Scheme 1b above.

EXAMPLE 3B

1-Benzo[1,3]dioxol-5-yl-2-(6-methyl-pyridin-2-yl)-ethanone (III)

n-Butyllithium (2.5 M in hexanes, 13.8 mL, 34.4 mmol) was added slowly to a solution of diisopropylamine (4.53 mL, 32.3 mmol) in anhydrous THF (50 mL) at −78° C. After being stirred for 0.1 hour, the mixture was allowed to warm up to 0° C. Stirring continued for 0.5 hour. The mixture was then cooled to −78° C. and 2,6-lutidine (3.76 mL, 32.3 mmol) was added slowly. The mixture was allowed to warm up to 0° C. and stirred for 0.5 hour. The mixture was then cooled to −78° C. before the slow addition of benzo[1,3]dioxole-5-carboxylic acid methoxy-methyl-amide (4.5 g, 21.5 mmol; see Example 2 above) in anhydrous THF (10 mL). The mixture was stirred at −78° C. for 0.5 hour, at 0° C. for 0.5 hour, and at room temperature for 2 hours. The mixture was then quenched with ammonium chloride aqueous solution and extracted with ethyl acetate. The extract was washed with brine, dried over sodium sulfate, filtered, and concentrated. After purification using column chromatography on silica gel (eluent: ethyl acetate (2): hexanes (8)), 4.8 g (87%) of 1-Benzo[1,3]dioxol-5-yl-2-(6-methyl-pyridin-2-yl)-ethanone as a yellow solid was obtained. MS (ESP$^+$) m/z 256.1 (M+1). $^1$H NMR (400 MHz, Methanol-d$_4$) δ 7.56 (t, 1H, J=7.5 Hz), 7.39 (dd, 1H, J=1.8 Hz, 8.3 Hz), 7.30 (dd, 1H, J=0.5 Hz, 1.8 Hz), 6.93 (m, 1H), 6.83 (m, 2H), 5.98 (s, 2H), 4.87 (s, 2H), 2.50 (s, 3H).

EXAMPLE 3C

1-(6-Methyl-pyridin-2-yl)-2-[1,2,4]triazolo[1,5-a]pyridin-6-yl-ethanone (IIIa)

Synthesis of the title compound is described in parts (a) and (b) below.

(a) [1,2,4]Triazolo[1,5-a]pyridine-6-carbaldehyde

To a solution of 6-iodo-[1,2,4]triazolo[1,5-a]pyridine (5.0 g, 20 mmol; prepared from 2-amino-5-iodopyridine (Aldrich-Sigma, St. Louis, Mo.) according to WO 01/62756) in anhydrous THF (300 mL) at 0° C. was slowly added a solution of isopropylmagnesium bromide in THF (1 M, 31 mL, 31 mmol). The resulting milky suspension was stirred at 0° C. After an hour, DMF (6 mL, 50 mmol) was added to the suspension at 0° C. and the suspension was allowed to warm up to room temperature and stirred for 4 additional hours. 100 mL of water was then added at room temperature and stirred for 1 hour. The resulting mixture was extracted with diethylether and washed with saturated $Na_2CO_3$. The extracts were dried over $MgSO_4$ and concentrated. The residue was purified on a short silica gel cake with EtOAc to give [1,2,4]triazolo[1,5-a]pyridine-6-carbaldehyde as a light yellow solid (3 g, 100%). ESP+ m/e 148.0. $^1$H NMR (CDCl$_3$, 300 MHz), δ 10.03 (s, 1H), 9.10 (s, 1H), 8.49 (s, 1H), 8.02 (d, 1H), 7.82 (d, 1H).

(b) 1-(6-Methyl-pyridin-2-yl)-2-[1,2,4]triazolo[1,5-a]pyridin-6-yl-ethanone

To a solution of [1,2,4]triazolo[1,5-a]pyridine-6-carbaldehyde (3 g, 20 mmol; see subpart (a) above) and [(6-methyl-pyridin-2-yl)-phenylamino-methyl]-phosphonic acid diphenyl ester (8.8 g, 20 mmol; prepared from 6-methyl-pyridine-2-carboxaldehyde (Aldrich-Sigma, St. Louis, Mo.) according to *Tetrahedron Lett.* 39:1717-1720 (1998)) in a mixture of THF (40 mL) and iPrOH (10 mL) was added $Cs_2CO_3$ (8.6 g, 26 mmol) and the mixture was stirred at room temperature for overnight. A solution of 3N HCl (30 mL) was added dropwise to the above mixture and stirred for 1 hour. It was then diluted with MTBE (methyl t-butyl ether) and extracted with 1N HCl twice. The aqueous extracts were neutralized with ca. 50% KOH until pH 7-8 was reached and precipitates formed. The precipitates were collected, washed with water, and dried to yield 1-(6-methyl-pyridin-2-yl)-2-[1,2,4]triazolo[1,5-a]pyridin-6-yl-ethanone as an offwhite solid (2.9 g). The filtrates were extracted with EtOAc and dried over $MgSO_4$ and concentrated. The residue was recrystalized with iPrOH/H$_2$O to yield more desired product (0.6 g). ESP+, m/e 253. $^1$H NMR (CDCl$_3$, 300 MHz), δ 8.6 (s, 1H), 8.29 (s, 1H), 7.87 (d, 1H), 7.72 (t, 1H), 7.70 (d, 1H), 7.53 (dd, 1H), 7.36 (d, 1H), 4.61 (s, 2H), 2.66 (s, 3H).

EXAMPLE 4

1-Benzo[1,3]dioxol-5-yl-2-(6-methyl-pyridin-2-yl)-ethane-1,2-dione 2-oxime (IV)

Sodium nitrite (0.405 g, 5.88 mmol) was added to a solution of 1-benzo[1,3]dioxol-5-yl-2-(6-methyl-pyridin-2-yl)-ethanone (1.0 g, 3.92 mmol; see Example 3B above) in a mixture of HOAc/THF/H$_2$O (6:4:1, 22 mL). The mixture was stirred at 0° C. for 1 hour and then at room temperature for 1 hour. Solvent was removed under reduced pressure. Residue was dissolved in water and NaOH (3N) was added until the pH value was more than 8. The aqueous solution was then extracted with ethyl acetate. The organic layer was washed with brine, dried over sodium sulfate, filtered, and concentrated to give 0.90 g (81%) of 1-Benzo[1,3]dioxol-5-yl-2-(6-methyl-pyridin-2-yl)ethane-1,2-dione 2-oxime as a yellow foam. MS (ESP$^+$) m/z 285.1 (M+1). $^1$H NMR (300 MHz, CDCl$_3$) δ 7.49 (m, 4H), 7.09 (d, 1H, J=7.5 Hz), 6.81 (d, 1H, J=7.8 Hz), 6.04 (s, 2H), 2.43 (s, 3H).

Synthesis of exemplary compounds of formula (I) are described in Examples 5-24 below.

EXAMPLE 5

4-(4-Benzo[1,3]dioxol-5-yl-5-(6-methyl-pyridin-2-yl)-1H-imidazol-2-yl)-piperidine-1-carboxylic acid benzyl ester 4-Formyl-N-Cbz-piperidine (0.297 g, 1.2 mmol) was added to a solution of 1-benzo[1,3]dioxol-5-yl-2-(6-methyl-pyridin-2-yl)-ethane-1,2-dione 2-oxime (0.280 g, 1.0 mmol, see Example 4) and ammonium acetate (1.54 g, 20.0 mmol) in acetic acid (10 mL). The mixture was reflux for 2 hours. Solvent was removed under reduced pressure. The reaction mixture was then quenched with an ammonia/ice mixture. The aqueous solution was extracted with ethyl acetate. The extract was washed with brine, dried over sodium sulfate, filtered, and concentrated. HPLC purification eluting with acetonitrile:water gave 0.12 g (23%) of the hydroxyimidazole as a yellow solid. MS (ESP$^+$) m/z 513.2 (M+1)

The above mentioned hydroxyimidazole (0.50 g, 0.98 mmol) was added to a solution of TiCl$_3$/HCl (10%, 5 mL) and methanol (20 mL). The mixture was stirred at room temperature for 2 hours. Ammonia/ice mixture was added to quench the reaction. The aqueous solution was extracted with ethyl acetate. The ethyl acetate extract was washed with brine, dried over sodium sulfate, filtered, and concentrated. HPLC purification eluting with acetonitrile:water gave 0.16 g (33%) of the title compound as a yellow solid. MS (ESP$^+$) m/z 497.3 (M+1). $^1$H NMR (400 MHz, Methanol-d$_4$) δ 7.71 (t, 1H, J=7.8 Hz), 7.35 (m, 6H), 7.26 (d, 1H, J=7.8 Hz), 7.01 (m, 3H), 6.07 (s, 2H), 5.16 (s, 2H), 4.35 (m, 2H), 3.36 (m, 1H), 3.03 (m, 2H), 2.64 (s, 3H), 2.11 (m, 2H), 1.87 (m, 2H).

EXAMPLE 6

4-(4-Benzo[1,3]dioxol-5-yl-5-pyridin-2-yl-1H-imidazol-2-yl)-piperidine-1-carboxylic acid benzyl ester 4-(4-Benzo[1,3]dioxol-5-yl-1-hydroxy-5-pyridin-2-yl-1H-imidazol-2-yl)-piperidine-1-carboxylic acid benzyl ester (0.9 g, 1.8 mmol), which was prepared with 4-formyl-N-Cbz-piperidine and 1-benzo[1,3]dioxol-5-yl-2-(pyridin-2-yl)-ethane-1,2-dione 2-oxime in a similar manner as described in Example 5, was added to a solution of TiCl$_3$/HCl (10% 15 mL) and methanol (20 mL). The mixture was stirred at room temperature for 2 hours. Ammonia/ice mixture was added to quenched the reaction. The aqueous solution was extracted with ethyl acetate. Ethyl acetate extract was washed with brine, dried over sodium sulfate, filtered, and concentrated. Column chromatography on silica gel eluting with methanol:dichloromethane (5:95) gave 0.52 g (60%) of the title compound as a yellow foam. MS (ESP$^+$) m/z 483.02 (M+1). $^1$H NMR (400 MHz, CDCl$_3$) δ 8.50 (m, 1H), 7.50 (m, 2H), 7.34 (m, 5H), 7.09 (m, 3H), 6.85 (d, 1H, J=7.9 Hz), 6.00 (s, 2H), 5.14 (s, 2H), 4.29 (m, 2H), 3.00 (m, 3H), 2.10 (m, 2H), 1.81 (m, 2H).

EXAMPLE 7

3-[4-Benzo[1,3]dioxol-5-yl-5-(6-methyl-pyridin-2-yl)-1H-imidazol-2-yl]-piperidine-1-carboxylic acid benzyl ester 3-[4-Benzo[1,3]dioxol-5-yl-1-hydroxy-5-(6-methyl-pyridin-2-yl)-1H-imidazol-2-yl]-piperidine-1-carboxylic acid benzyl ester (0.50 g, 0.98 mmol), which was prepared with 3-formyl-N-Cbz-piperidine and 1-benzo[1,3]dioxol-5-yl-2-(6-methyl-pyridin-2-yl)-ethane-1,2-dione 2-oxime in a similar manner as described in Example 5, was added to a solution of $TiCl_3$/HCl (10% 5 mL) and methanol (20 mL). The mixture was stirred at room temperature for 2 hours. Ammonia/ice mixture was added to quench the reaction. The aqueous solution was extracted with ethyl acetate. Ethyl acetate extract was washed with brine, dried over sodium sulfate, filtered, and concentrated. HPLC purification eluting with acetonitrile:water gave 0.15 g (30%) of the title compound as a yellow solid. MS ($ESP^+$) m/z 497.2 (M+1). $^1$H NMR (400 MHz, Methanol-$d_4$) δ 7.78 (t, 1H, J=7.9 Hz), 7.34 (m, 7H), 7.01 (m, 3H), 6.08 (s, 2H), 5.16 (s, 2H), 4.41 (m, 1H), 4.15 (m, 1H), 3.22 (m, 2H), 3.10 (m, 1H), 2.66 (s, 3H), 2.26 (m, 1H), 1.92 (m, 2H), 1.64 (m, 1H).

EXAMPLE 8

3-[4-Benzo[1,3]dioxol-5-yl-5-(6-methyl-pyridin-2-yl)-1H-imidazol-2-yl]-pyrrolidine-1-carboxylic acid benzyl ester 3-[4-Benzo[1,3]dioxol-5-yl-1-hydroxy-5-(6-methyl-pyridin-2-yl)-1H-imidazol-2-yl]-pyrrolidine-1-carboxylic acid benzyl ester (0.180 g, 0.361 mmol), which was prepared with 3-formyl-N-Cbz-pyrrolidine and 1-benzo[1,3]dioxol-5-yl-2-(6-methyl-pyridin-2-yl)-ethane-1,2-dione 2-oxime in a similar manner as described in Example 5, was added to a solution of $TiCl_3$/HCl (10% 2 mL) and methanol (10 mL). The mixture was stirred at room temperature for 2 hours. Ammonia/ice mixture was added to quenched the reaction. The aqueous solution was extracted with ethyl acetate. Ethyl acetate extract was washed with brine, dried over sodium sulfate, filtered, and concentrated. HPLC purification eluting with acetonitrile:water gave 0.03 g (17%) of the title compound as a yellow solid. MS (ESP+) m/z 483.14 (M+1). $^1$H NMR (400 MHz, Methanol-$d_4$) δ 7.84 (t, 1H, J=8.0 Hz), 7.37 (m, 7 H), 7.01 (m, 3H), 6.07 (s, 2H), 5.16 (s, 2H), 4.01 (m, 1H), 3.83 (m, 1H), 3.74 (m, 1H), 3.55 (m, 1H), 2.68 (s, 3H), 2.50 (m, 1H), 2.36 (m, 1H).

EXAMPLE 9

2-(5-Benzo[1,3]dioxol-5-yl-2-piperidin-4-yl-3H-imidazol-4-yl)-6-methyl-pyridine Palladium on activated carbon (0.010 g) was added to a solution of 4-(4-benzo[1,3]dioxol-5-yl-5-(6-methyl-pyridin-2-yl)-1H-imidazol-2-yl)-piperidine-1-carboxylic acid benzyl ester (0.100 g, 0.20 mmol; see Example 5) in methanol (5 mL). The reaction mixture was stirred under hydrogen atmosphere for 4 hours. The mixture was then filtered and concentrated to give 0.070 g (97%) of the title compound as a yellow oil. MS ($ESP^+$) m/z 363.2 (M+1). $^1$H NMR (300 MHz, $CDCl_3$) δ 7.41 (t, 1H, J=7.8 Hz), 7.29 (d, 1H, J=8.1 Hz), 7.10 (m, 2H), 6.92 (d, 1H, J=7.5 Hz), 6.83 (m, 1H), 5.98 (s, 2H), 3.18 (m, 2H), 2.95 (m, 1H), 2.73 (m, 2H), 2.46 (s, 3H), 1.96 (m, 2H), 1.82 (m, 2H).

EXAMPLE 10

2-[5-Benzo[1,3]dioxol-5-yl-2-(1-phenylmethanesulfonyl-piperidin-4-yl)-3H-imidazol-4-yl]-6-methyl-pyridine α-Toluenesulfonyl chloride (0.032 g, 0.17 mmol) and diisopropylethylamine (0.036 mL, 0.21 mmol) were added to a solution of 2-(5-benzo[1,3]dioxol-5-yl-2-piperidin-4-yl-3H-imidazol-4-yl)-6-methyl-pyridine (0.050 g, 0.14 mmol; see Example 9) in anhydrous THF (3 mL). The reaction mixture was stirred at room temperature for 3 hours. Solvent was removed under reduced pressure, and the residue was dissolved in 1 mL DMSO. The DMSO solution was filtered and injected onto preparative HPLC. HPLC purification eluting with acetonitrile:water gave 0.005 g (7%) of the title compound as a yellow solid. MS ($ESP^+$) m/z 517.2 (M+1). $^1$H NMR (400 MHz, Methanol-$d_4$) δ 7.73 (t, 1H, J=7.7 Hz), 7.42 (m, 5H), 7.33 (d, 1H, J=7.3 Hz), 7.27 (d, 1H, J=7.3 Hz), 6.07 (s, 2H), 4.40 (s, 2H), 3.82 (m, 2H), 3.19 (m, 1H), 2.85 (m, 2H), 2.66 (s, 3H), 2.10 (m, 2H), 1.92 (m, 2H).

EXAMPLE 11

2-[5-Benzo[1,3]dioxol-5-yl-2-(1-phenylmethanesulfonyl-piperidin-4-yl)-3H-imidazol-4-yl]-pyridine α-Toluenesulfonyl chloride (0.023 g, 0.12 mmol) and diisopropylethylamine (0.026 mL, 0.15 mmol) were added to a solution of 2-(5-benzo[1,3]dioxol-5-yl-2-piperidin-4-yl-3H-imidazol-4-yl)-pyridine (0.035 g, 0.10 mmol, in 3 mL of anhydrous THF), which was prepared with 4-(4-benzo[1,3]dioxol-5-yl-5-pyridin-2-yl-1H-imidazol-2-yl)-piperidine-1-carboxylic acid benzyl ester in a similar manner as described in Example 9. The reaction mixture was stirred at room temperature for 3 hours. Solvent was removed under reduced pressure, and the residue was dissolved in 1 mL DMSO. The DMSO solution was filtered and injected onto preparative HPLC. HPLC purification eluting with acetonitrile:water gave 0.005 g (10%) of the title compound as a yellow solid. MS ($ESP^+$) m/z 503.1 (M+1). $^1$H NMR (400 MHz, Methanol-$d_4$) δ 8.67 (m, 1H), 7.82 (m, 1H), 7.42 (m. 7H), 7.02 (m, 3H), 6.07 (s, 2H), 4.38 (s, 2H), 3.81 (m, 2H), 3.17 (m, 1H), 2.85 (m, 1H), 2.10 (m, 2H), 1.90 (m, 2H).

EXAMPLE 12

2-[5-Benzo[1,3]dioxol-5-yl-2-(1-methanesulfonyl-piperidin-4-yl)-3H-imidazol-4-yl]-pyridine Methanesulfonyl chloride (0.009 mL, 0.12 mmol) and diisopropylethylamine (0.026 mL, 0.15 mmol) were added to a solution of 2-(5-benzo[1,3]dioxol-5-yl-2-piperidin-4-yl-3H-imidazol-4-yl)-pyridine (0.035 g, 0.10 mmol; prepared as described in Example 11) in anhydrous THF (3 mL). The reaction mixture was stirred at room temperature for 3 hours. Solvent was removed under reduced pressure, and the residue was dissolved in 1 mL DMSO. The DMSO solution was filtered and injected onto preparative HPLC. HPLC purification eluting with acetonitrile:water gave 0.012 g (28%) of the title compound as a yellow solid. MS ($ESP^+$) m/z 427.1 (M+1). $^1$H NMR (400 MHz, $CDCl_3$) δ 8.65 (m, 1H), 7.83 (m, 1H), 7.56 (m, 1H), 7.45 (m. 1H), 7.03 (dd, 1H, J=1.8 Hz, 8.1

Hz), 6.97 (d, 1H, J=1.8 Hz), 6.88 (d, 1H, d=8.1 Hz), 6.05 (s, 2H), 3.91 (m, 2H), 3.47 (m, 1H), 2.89 (m, 2H), 2.84 (s, 3H), 2.22 (m, 2H), 2.11 (m, 2H).

EXAMPLE 13

2-[5-Benzo[1,3]dioxol-5-yl-2-(1-methanesulfonyl-piperidin-4-yl)-3H-imidazol-4-yl]-6-methyl-pyridine Methanesulfonyl chloride (0.009 mL, 0.12 mmol) and diisopropylethylamine (0.026 mL, 0.15 mmol) were added to a solution of 2-(5-benzo[1,3]dioxol-5-yl-2-piperidin-4-yl-3H-imidazol-4-yl)-6-methyl-pyridine (0.036 g, 0.10 mmol; see Example 9) in anhydrous THF (3 mL). The reaction mixture was stirred at room temperature for 3 hours. Solvent was removed under reduced pressure, and the residue was dissolved in 1 mL DMSO. The DMSO solution was filtered and injected onto preparative HPLC. HPLC purification eluting with acetonitrile:water gave 0.011 g (25%) of the title compound as a yellow solid. MS (ESP$^+$) m/z 441.2 (M+1). $^1$H NMR (400 MHz, Methanol-d$_4$) δ 7.74 (t, 1H, J=7.9 Hz), 7.34 (m, 1H), 7.28 (m, 1H), 7.03 (m, 3H), 6.08 (s, 2H), 3.92 (m, 2H), 3.25 (m, 1H), 2.94 (m, 2H), 2.90 (s, 3H), 2.66 (s, 3H), 2.23 (m, 2H), 2.03 (m, 2H).

EXAMPLE 14

4-(4-Benzo[1,3]dioxol-5-yl-5-pyridin-2-yl-1H-imidazol-2-yl)-piperidine-1-carboxylic acid 2-chloro-benzyl ester 2-Chlorobenzyl chloroformate (0.011 mL, 0.070 mmol) was added to a solution of 2-(5-benzo[1,3]dioxol-5-yl-2-piperidin-4-yl-3H-imidazol-4-yl)-pyridine (0.021 g, 0.059 mmol; prepared as described in Example 11) in a mixture of THF (3 mL) and 2 M sodium bicarbonate aqueous solution (0.3 mL). The mixture was stirred at room temperature for 2 hours. Mixture was partitioned between ethyl acetate and water. The organic solution was washed with brine, dried over sodium sulfate, filtered, and concentrated. HPLC purification eluting with acetonitrile:water gave 0.026 g (70%) of the title compound as a yellow solid. MS (ESP$^+$) m/z 517.03 (M+1). $^1$H NMR (400 MHz, CDCl$_3$) δ 8.60 (m, 1H), 7.81 (m, 1H), 7.60 (d, 1H, J=8.2 Hz), 7.39 (m, 3H), 7.27 (m, 2H), 7.07 (dd, 1H, J=8.1, 1.8 Hz), 6.99 (d, 1H, J=1.8 Hz), 6.90 (d, 1H, J=8.1 Hz), 6.05 (s, 2H), 5.24 (s, 2H), 4.36 (m, 2H), 3.48 (m, 1H), 2.98 (m, 2H), 2.17 (m, 2H), 1.86 (m, 2H).

EXAMPLE 15

4-(4-Benzo[1,3]dioxol-5-yl-5-pyridin-2-yl-1H-imidazol-2-yl)-piperidine-1-carboxylic acid 2,4-dichloro-benzylamide 2,3-Dichlorobenzylisocyanate (0.009 mL, 0.07 mmol) was added to a solution of 2-(5-benzo[1,3]dioxol-5-yl-2-piperidin-4-yl-3H-imidazol-4-yl)-pyridine (0.021 g, 0.059 mmol; prepared as described in Example 11) and diisopropylethylamine (0.031 mL, 0.177 mmol) in anhydrous THF (5 mL). The mixture was stirred at room temperature for 2 hours and was partitioned between ethyl acetate and water. The organic solution was washed with brine, dried over sodium sulfate, filtered, and concentrated. HPLC purification eluting with acetonitrile:water gave 0.016 g (41%) of the title compound as a yellow solid. MS (ESP$^+$) m/z 550.2 (M+1). $^1$H NMR (400 MHz, CDCl$_3$) δ 8.58 (m, 1H), 7.80 (m, 1H), 7.56 (d, 1H, J=8.2 Hz), 7.39 (m, 1H), 7.32 (d, 1H, J=2.1 Hz), 7.25 (d, 1H, J=8.2 Hz), 7.14 (dd, 1H, J=8.2, 2.0 Hz), 7.03 (dd, 1H, J=8.1, 1.8 Hz), 6.95 (d, 1H, J=1.6 Hz), 6.87 (d, 1H, J=8.0 Hz), 6.04 (s, 2H), 4.38 (s, 2H), 4.11 (m, 2H), 3.48 (m, 1H), 2.99 (m, 2H), 2.14 (m, 2H), 1.92 (m, 2H).

EXAMPLE 16

1-[4-(4-Benzo[1,3]dioxol-5-yl-5-pyridin-2-yl-1H-imidazol-2-yl)-piperidin-1-yl]-ethanone Acetic anhydride (0.011 mL, 0.12 mmol) was added to a solution of 2-(5-benzo[1,3]dioxol-5-yl-2-piperidin-4-yl-3H-imidazol-4-yl)-pyridine (0.035 g, 0.10 mmol; prepared as described in Example 11) and diisopropylethylamine (0.021 mL, 0.12 mmol) in anhydrous THF (3 mL). The mixture was stirred at room temperature for 18 hours and was partitioned between ethyl acetate and water. The organic solution was washed with brine, dried over sodium sulfate, filtered, and concentrated. HPLC purification eluting with acetonitrile:water gave 0.010 g (26%) of the title compound as a yellow solid. MS (ESP$^+$) m/z 391.2 (M+1). $^1$H NMR (400 MHz, Methanol-d$_4$) δ 8.59 (m, 1H), 7.73 (m, 1H), 7.34 (m, 2H), 6.94 (m, 3H), 5.98 (s, 2H), 4.83 (s, 3H), 4.60 (m, 2H), 4.01 (m, 2H), 3.28 (m, 3H), 2.69 (m, 2H).

EXAMPLE 17

2-[5-Benzo[1,3]dioxol-5-yl-2-(1-furan-2-yl-methyl-piperidin-4-yl)-3H-imidazol-4-yl]-pyridine Sodium triacetoxyborohydride (0.030 g, 0.14 mmol) was added to a solution of 2-(5-benzo[1,3]dioxol-5-yl-2-piperidin-4-yl-3H-imidazol-4-yl)-pyridine (0.035 g, 0.10 mmol; prepared as described in Example 11) and furan-2-carbaldehyde (0.0083 mL, 0.10 mmol) in dichloromethane (5 mL). The mixture was stirred at room temperature for 18 hours and was filtered and concentrated. HPLC purification eluting with acetonitrile:water gave 0.010 g (23%) of the title compound as a yellow solid. MS (ESP$^+$) m/z 429.1. $^1$H NMR (400 MHz, DMSO-d$_6$) δ 8.67 (m, 1H), 7.87 (m, 2H), 7.44 (m, 2H), 7.09 (m, 3H), 6.73 (d, 1H, J=3.2 Hz), 6.60 (m, 1H), 6.12 (s, 2H), 4.45 (s, 2H), 3.54 (m, 2H), 3.26 (m, 1H), 3.11 (m, 2H), 2.33 (m, 2H), 2.06 (m, 2H).

EXAMPLE 18

{4-[4-Benzo[1,3]dioxol-5-yl-5-(6-methyl-pyridin-2-yl)-1H-imidazol-2-yl]-cyclohexyl}-carbamic acid benzyl ester (4-Formyl-cyclohexyl)-carbamic acid benzyl ester (0.133 g, 0.507 mmol; see Example 1 above) was added to a solution of 1-benzo[1,3]dioxol-5-yl-2-(6-methyl-pyridin-2-yl)-ethane-1,2-dione 2-oxime (0.120 g, 0.422 mmol; see Example 4) and ammonium acetate (0.651 g, 8.44 mmol) in acetic acid (5 mL). The mixture was refluxed for 2 hours and solvent was removed under reduced pressure. The reaction mixture was then quenched with an ammonia/ice mixture. The aqueous solution was extracted with ethyl acetate. Ethyl acetate extract was washed with brine, dried over sodium sulfate, filtered, and concentrated. HPLC purification eluting with acetonitrile:water gave 0.035 g (16%) of the hydroxy-imidazole as a yellow solid. MS (ESP$^+$) m/z 527.2 (M+1).

The above mentioned hydroxyimidazole (0.100 g, 0.190 mmol) was added to a solution of TiCl$_3$/HCl (10% 2 mL) and methanol (10 mL). The mixture was stirred at room temperature for 2 hours. Ammonia/ice mixture was added to quench the reaction. The aqueous solution was extracted with ethyl acetate. The ethyl acetate extract was washed with brine, dried over sodium sulfate, filtered, and concentrated. HPLC purification eluting with acetonitrile:water gave 0.015 g (15%) of the title compound as a yellow solid. MS (ESP$^+$) m/z 511.2 (M+1). $^1$H NMR (400 MHz, Methanol-$_4$) δ 7.68 (m, 1H), 7.33 (m, 6H), 7.22 (m, 1H), 7.01 (m, 3H), 6.07 (s, 2H), 5.08 (s, 2H), 3.52 (m, 1H), 3.09 (m, 1H), 2.66 (s, 3H), 2.16 (m, 3H), 1.98 (m, 1H), 1.83 (m, 2H), 1.44 (m, 2H).

EXAMPLE 19

4-[4-Benzo[1,3]dioxol-5-yl-5-(6-methyl-pyridin-2-yl)-1H-imidazol-2-yl]cyclohexylamine Palladium on activated carbon (0.017 g) was added to a solution of {4-[4-Benzo[1,3]dioxol-5-yl-5-(6-methyl-pyridin-2-yl)-1H-imidazol-2-yl]-cyclohexyl}-carbamic acid benzyl ester (see Example 18; 0.370 g, 0.725 mmol) in methanol (5 mL). The reaction mixture was stirred under hydrogen atmosphere for 4 hours. The mixture was then filtered and concentrated to give 0.250 g (92%) of the title compound as a yellow oil. MS (ESP$^+$) m/z 377.2 (M+1). $^1$H NMR (300 MHz, Methanol-d$_4$) δ 7.80 (t, 1H, J=7.8 Hz), 7.36 (m, 2H), 7.01 (m, 3H), 6.07 (s, 2H), 3.47 (m, 1H), 3.32 (m, 1H), 2.29 (m, 2H), 2.03 (m, 4H), 1.90 (m, 2H).

EXAMPLE 20

N-{4-[4-Benzo[1,3]dioxol-5-yl-5-(6-methyl-pyridin-2-yl)-1H-imidazol-2-yl]-cyclohexyl}-C-phenyl-methanesulfonamide α-Toluenesulfonyl chloride (0.023 g, 0.12 mmol) and diisopropylethylamine (0.026 mL, 0.15 mmol) were added to a solution of 4-[4-benzo[1,3]dioxol-5-yl-5-(6-methyl-pyridin-2-yl)-1H-imidazol-2-yl] cyclohexylamine (see Example 19; 0.038 g, 0.10 mmol) in anhydrous THF (3 mL). The reaction mixture was stirred at room temperature for 3 hours. Solvent was removed under reduced pressure, and the residue was dissolved in 1 mL DMSO. The DMSO solution was filtered and injected onto preparative HPLC. HPLC purification eluting with acetonitrile:water gave 0.005 g (9%) of the title compound as a yellow solid. MS (ESP$^+$) m/z 531.1 (M+1). $^1$H NMR (400 MHz, Methanol-d$_4$) δ 7.67 (m, 1H), 7.41 (m, 6H), 7.30 (m, 1H), 7.22 (m, 1H), 7.01 (m, 2H), 6.07 (s, 2H), 4.34 (s, 2H), 3.05 (m, 2H), 2.63 (s, 3H), 2.13 (m, 2H), 1.95 (m, 2H), 1.72 (m, 2H), 1.43 (m, 2H).

EXAMPLE 21

4-[4-Benzo[1,3]dioxol-5-yl-5-(6-methyl-pyridin-2-yl)-1H-imidazol-2-yl]-bicyclo[2.2.2]octane-1-carboxylic acid methyl ester 4-Formyl-bicyclo[2.2.2]octane-1-carboxylic acid methyl ester (0.284 g, 1.0 mmol) was added to a solution of 1-benzo[1,3]dioxol-5-yl-2-(6-methyl-pyridin-2-yl)-ethane-1,2-dione 2-oxime (see Example 4; 0.215 g, 1.1 mmol) and ammonium acetate (1.54 g, 20 mmol) in acetic acid (5 mL). The mixture was refluxed for 2 hours. Solvent was removed under reduced pressure. The reaction mixture was then quenched with ammonia/ice mixture. The aqueous solution was extracted with ethyl acetate. Ethyl acetate extract was washed with brine, dried over sodium sulfate, filtered, and concentrated to give 0.300 g (65%) of the hydroxyimidazole as a yellow solid. MS (ESP$^+$) m/z 462.3 (M+1).

The above mentioned hydroxyimidazole (0.250 g, 0.54 mmol) was added to a solution of TiCl$_3$/HCl (10% 3 mL) and methanol (10 mL). The mixture was stirred at room temperature for 2 hours. Ammonia/ice mixture was added to quench the reaction. The aqueous solution was extracted with ethyl acetate. Ethyl acetate extract was washed with brine, dried over sodium sulfate, filtered, and concentrated. HPLC purification eluting with acetonitrile:water gave 0.100 g (42%) of the title compound as a yellow solid. MS (ESP$^+$) m/z 446.2 (M+1). $^1$H NMR (400 MHz, Methanol-d$_4$) δ 7.72 (t, 1H, J=7.8 Hz), 7.34 (d, 1H, J=7.7 Hz), 7.22 (d, 1H, J=7.9 Hz), 6.97 (m, 3H), 6.05 (s, 2H), 3.67 (s, 3H), 2.64 (s, 3H), 2.10 (m, 6H), 1.99 (m, 6H).

EXAMPLE 22

4-[4-Benzo[1,3]dioxol-5-yl-5-(6-methyl-pyridin-2-yl)-1H-imidazol-2-yl]-bicyclo[2.2.2]octane-1-carboxylic acid Lithium hydroxide monohydrate (0.020 g, 0.487 mmol) was added to a solution of 4-[4-benzo[1,3]dioxol-5-yl-5-(6-methyl-pyridin-2-yl)-1H-imidazol-2-yl]-bicyclo[2.2.2]octane-1-carboxylic acid methyl ester (see Example 21; 0.150 g, 0.325 mmol) in a mixture of THF/MeOH/H$_2$O (2/1/1, 4 mL). The mixture was stirred for 3 hours. Solvent was removed. Residue was diluted with water (30 mL). Citric acid was added to the solution to make the pH lower than 7. The aqueous solution was extracted with ethyl acetate. Ethyl acetate extract was washed with brine, dried over sodium sulfate, filtered and concentrated to give 0.140 g (99%) of the title compound as a yellow solid. MS (ESP$^+$) m/z 432.2 (M+1). $^1$H NMR (400 MHz, Methanol-d$_4$) δ 7.72 (m, 1H), 7.33 (d, 1H, J=7.7 Hz), 7.22 (d, 1H, J=7.7 Hz), 6.98 (m, 3H), 6.05 (s, 2H), 2.64 (s, 3H), 2.11 (m, 6H), 1.99 (m, 6H).

EXAMPLE 23

{4-[4-Benzo[1,3]dioxol-5-yl-5-(6-methyl-pyridin-2-yl)-1H-imidazol-2-yl]-bicyclo[2.2.2]oct-1-yl}-carbamic acid benzyl ester Diphenylphosphoryl azide (0.070 mL, 0.324 mmol) was added to a solution of 4-[4-benzo[1,3]dioxol-5-yl-5-(6-methyl-pyridin-2-yl)-1H-imidazol-2-yl]-bicyclo[2.2.2]octane-1-carboxylic acid (see Example 22; 0.140 g, 0.324 mmol) and diisopropylethylamine (0.068 mL, 0.39 mmol) in toluene (5 mL). The mixture was stirred for 2 hours. Benzyl alcohol (0.067 mL, 0.648 mmol) was added to the mixture. The mixture was stirred at room temperature for 18 hours. Solvent was removed. The mixture was partitioned between ethyl acetate and water. The organic solution was washed with brine, dried over sodium sulfate, filtered, and concentrated. HPLC purification eluting with acetonitrile:water gave 0.002 g (1%) of the title compound as a yellow solid. MS (ESP$^+$) m/z 537.4 (M+1). $^1$H NMR (400 MHz, Methanol-d$_4$) δ 7.71 (m, 1H), 7.33 (m, 5H), 7.22 (m, 2H), 6.97 (m, 3H), 6.05 (s, 2H), 5.02 (s, 2H), 2.63 (s, 3H), 2.17 (m, 6H), 2.06 (m, 6H).

EXAMPLE 24

4-[4-Benzo[1,3]dioxol-5-yl-5-(6-ethyl-pyridin-2-yl)-1H-imidazol-2-yl]-piperidine-1-carboxylic acid benzyl ester To a solution of 4-[4-benzo[1,3]dioxol-5-yl-5-(6-bromo-pyridin-2-yl)-1H-imidazol-2-yl]-piperidine-1-carboxylic acid benzyl ester (prepared in accordance with Scheme 1b with 6-bromo-piperidine-2-carbaldehyde as the starting material; 100 mg, 0.18 mmol) in DMF (1 mL) and triethylamine (2 mL) under nitrogen, was added $PdCl_2(PPh_3)_2$ (2 mg, 0.005 mmol) and CuI (2 mg, 0.01 mmol), then followed with trimethylsilylacetylene (30 uL, 0.20 mmol). The mixture was stirred at room temperature for 4 hours until LC-MS showed complete coupling. Diethyl ether (30 mL) was added and the precipitate was filtered off. The clear solution was washed with saturated aqueous $NH_4Cl$, then 0.5M EDTA solution, and water, and then dried ($MgSO_4$). Concentration gave a yellow syrup that was dissolved in THF (20 mL). The solution was cooled to 0° C. and tetrabutylammonium fluoride (2 mL, 1 M in THF) was added. The mixture was stirred at room temperature for 30 minutes until LC-MS indicated complete removal of the silyl group. The reaction mixture was then concentrated in vacuum and passed through a short silica gel column with ethyl acetate/dichloromethane (1:1). The purified material was dissolved in ethanol (20 mL) and $PtO_2$ (50 mg) was added. The mixture was stirred under hydrogen (1 atm) at room temperature for 3 days until LC-MS showed major conversion of the alkyne to the correponding alkane. The solids were filtered off and the filtrates were concentrated and purified on preparative HPLC to give the title compound (3 mg, 3%) as a TFA salt. MS ($EPS^+$: 511.3 ($MH^+$)). $^1H$ NMR (400 MHz, MeOH-$d_4$) δ 7.60 (t, 1H), 7.39-7.29 (m, 5H), 7.23 (d, 1H), 7.13 (d, 1H), 6.93 (dd, 1H), 6.91 (dd, 1H), 6.81 (d, 1H), 5.95 (s, 2H), 5.14 (s, 2H), 4.28 (d(br), 2H), 3.04 (m, 1H), 3.02 (br, 2H), 2.79 (q, 2H), 2.00 (d(br), 2H), 1.85 (ddd, 2H), 1.28 (t, 3H)

The compounds listed in the following Table were prepared in an analogous manner to those described in the methods and examples above. The mass spectroscopy data of these compounds are included in the Table.

| Example | Chemical Name | $^1$H-NMR | MS (ES+) m/z (M + 1) |
|---|---|---|---|
| Example 25 | 2-(5-Benzo[1,3]dioxol-5-yl-2-piperidin-4-yl-3H-imidazol-4-yl)-pyridine | (400MHz, DMSO-d6), δ 8.67(d, 1H), 7.90(t, 1H), 7.47(d, 1H), 7.44(d, 1H), 7.14(s, 1H), 7.07(s, 2H), 6.12(s, 2H), 3.43(d, 2H), 3.31(t, 1H), 3.07(q, 2H), 2.23(d, 2H), 2.01(q, 2H) | 349.4 |
| Example 26 | 4-(4-Benzo[1,3]dioxol-5-yl-5-pyridin-2-yl-1H-imidazol-2-yl)-piperidine-1-carboxylic acid 4-nitro-benzyl ester | $^1$H NMR(400MHz, CDCl$_3$): δ 8.64(d, 1H), 8.22(d, 2H), 7.96(m, 1H), 7.65(d, 1H), 7.54(3H), 6.95(m, 5H), 6.05(s, 2H), 5.24(s, 2H), 4.35(m, 2H), 3.45(m, 1H), 2.97(m, 2H), 2.16(m, 2H), 1.92(m, 2H). | 528.09 |
| Example 27 | 4-(4-Benzo[1,3]dioxol-5-yl-5-pyridin-2-yl-1H-imidazol-2-yl)-piperidine-1-carboxylic acid 4,5-dimethoxy-2-nitro-benzyl ester | $^1$H NMR(400MHz, CDCl$_3$): δ 8.64(d, 1H), 7.93(t, 1H), 7.68(s, 1H), 7.64(d, 1H), 7.53(m, 1H), 7.04(dd, 1H), 6.98(s, H), 6.96(d, 1H), 6.90(d, 1H), 6.06(s, 2H), 5.51(s, 2H), 4.34(m, 2H), 3.97(s, 3H), 3.95(s, 3H), 3.50(m, 1H), 3.00(m, 2H), 2.16(m, 2H), 1.92(m, 2H). | 588.13 |
| Example 28 | 4-(4-Benzo[1,3]dioxol-5-yl-5-pyridin-2-yl-1H-imidazol-2-yl)-piperidine-1-carboxylic acid 3-fluoro-benzylamide | $^1$H NMR(400MHz, CDCl$_3$): δ 8.59(d, 1H), 7.74(m, 1H), 7.5(m, 1H), 7.36(m, 1H), 7.20(m, 1H), 6.94(m, 6H), 6.02(s, 2H), 4.29(s, 2H), 4.13(m, 2H), 3.44(m, 1H), 2.95(m, 2H), 2.08(m, 2H), 1.89(m, 2H). | 500.05 |
| Example 29 | 4-(4-Benzo[1,3]dioxol-5-yl-5-pyridin-2-yl-1H-imidazol-2-yl)-piperidine-1-carboxylic acid 4-fluoro-benzylamide | $^1$H NMR(400MHz, CDCl$_3$): δ 8.57(d, 1H), 7.76(m, 1H), 7.53(d, 1H), 7.35(m, 1H), 7.17(m, 1H), 6.95(m, 6H), 6.02(s, 2H), 4.27(s, 2H), 4.13(m, 2H), 3.44(m, 1H), 2.95(m, 2H), 2.08(m, 2H), 1.89(m, 2H). | 500.2 |
| Example 30 | 4-(4-Benzo[1,3]dioxol-5-yl-5-pyridin-2-yl-1H-imidazol-2-yl)-piperidine-1-carboxylic acid benzylamide | $^1$H NMR(400MHz, CDCl$_3$): δ 8.57(d, 1H), 7.70(m, 1H), 7.50(d, 1H), 7.23(m, 6H), 7.03(d, 1H), 6.96(d, 1H), 6.84(d, 1H), 6.00(s, 2H), 4.27(s, 2H), 4.09(m, 2H), 3.45(m, 1H), 2.93(m, 2H), 2.05(m, 2H), 1.87(m, 2H). | 482.07 |
| Example 31 | 2-{5-Benzo[1,3]dioxol-5-yl-2-[1-(toluene-4-sulfonyl)-piperidin-4-yl]-3H-imidazol-4-yl}-pyridine | $^1$H NMR(400MHz, CDCl$_3$): δ 8.53(d, 1H), 7.80(m, 1H), 7.65(d, 2H), 7.57(d, 1H), 7.41(m, 1H), 7.37(d, 2H), 7.04(m, 1H), 6.96(m, 1H), 6.87(d, 1H). 6.04(s, 2H), 3.95(m, 2H), 3.28(m, 1H), 2.46(s, 3H), 2.41(m, 2H), 2.24(m, 2H), 2.10(m, 2H). | 503.2 |
| Example 32 | 4-(4-Benzo[1,3]dioxol-5-yl-5-pyridin-2-yl-1H-imidazol-2-yl)-piperidine-1-carboxylic acid 4-methyl-benzylamide | $^1$H NMR(400MHz, CDCl$_3$): δ 8.59(d, 1H), 7.77(t, 1H), 7.52(d, 1H), 7.37(t, 1H), 7.10(m, 4H), 7.01(dd, 1H), 6.93(d, 1H), 6.85(d, 1H), 6.02(s, 2H), 4.24(s, 2H), 4.09(m, 2H), 3.45(m, 1H), 2.94(m, 2H), 2.29(s, 3H), 2.08(m, 2H), 1.91(m, 2H). | 496.3 |

-continued

| Example | Chemical Name | ¹H-NMR | MS (ES+) m/z (M + 1) |
|---|---|---|---|
| Example 33 | 4-(4-Benzo[1,3]dioxol-5-yl-5-pyridin-2-yl-1H-imidazol-2-yl)-piperidine-1-carboxylic acid 4-methoxy-benzylamide | ¹H NMR(400MHz, CDCl₃): δ 8.60(d, 1H), 7.77(m, 1H), 7.55(d, 1H), 7.37(m, 2H), 7.12(d, 1H), 7.04(m, 1H), 6.96(m, 1H), 6.83(m, 3H), 6.03(s, 2H), 4.25(s, 2H), 4.08(m, 2H), 3.77(s, 3H), 3.48(m, 1H), 2.96(m, 2H), 2.11(m, 2H), 1.91(m, 2H). | 512.3 |
| Example 34 | 4-(4-Benzo[1,3]dioxol-5-yl-5-pyridin-2-yl-1H-imidazol-2-yl)-piperidine-1-carboxylic acid 2-chloro-benzylamide | ¹H NMR(400MHz, CDCl₃): δ 8.56(d, 1H), 7.72(m, 1H), 7.51(d, 1H), 7.28(m, 3H), 7.14(m, 2H), 7.02(dd, 1H), 6.95(m, 1H), 6.84(d, 1H), 6.01(s, 2H), 4.37(s, 2H), 4.10(m, 2H), 3.47(m, 1H), 2.95(m, 2H), 2.08(m, 2H), 1.91(m, 2H). | 516.2 |
| Example 35 | 4-[4-(4-Benzo[1,3]dioxol-5-yl-5-pyridin-2-yl-1H-imidazol-2-yl)-piperidine-1-sulfonyl]-benzoic acid | | 533.1 |
| Example 36 | 4-(4-Benzo[1,3]dioxol-5-yl-5-pyridin-2-yl-1H-imidazol-2-yl)-piperidine-1-carboxylic acid amide | | 392.1 |
| Example 37 | 4-[4-(4-Benzo[1,3]dioxol-5-yl-5-pyridin-2-yl-1H-imidazol-2-yl)-piperidine-1-sulfonyl]-benzonitrile | ¹H NMR(400MHz, CDCl₃): δ 8.60(d, 1H), 7.87(m, 5H), 7.62(d, 1H), 7.49(m, 1H), 7.02(dd, 1H), 6.94(d, 1H), 6.89(d, 1H), 6.05(s, 2H), 3.97(m, 2H), 3.30(m, 1H), 2.56(m, 2H), 2.25(m, 2H), 2.05(m, 2H). | 514.1 |
| Example 38 | 2-{5-Benzo[1,3]dioxol-5-yl-2-[1-(4-chloro-benzenesulfonyl)-piperidin-4-yl]-3H-imidazol-4-yl}-pyridine | ¹H NMR(400MHz, CDCl₃): δ 8.56(d, 1H), 7.81(m, 1H), 7.70(d, 2H), 7.59(d, 1H), 7.55(d, 2H), 7.41(m, 1H), 7.04(dd, 1H), 6.96(d, 1H), 6.88(d, 1H), 6.04(s, 2H), 3.94(m, 2H), 3.30(m, 1H), 2.49(m, 2H), 2.25(m, 2H), 2.05(m, 2H). | 523.1 |
| Example 39 | 2-{5-Benzo[1,3]dioxol-5-yl-2-[1-(3,4-dichloro-benzenesulfonyl)-piperidin-4-yl]-3H-imidazol-4-yl}-pyridine | ¹H NMR(400MHz, CDCl₃): δ 8.57(d, 1H), 7.84(d, 1H), 7.81(d, 1H), 7.65(d, 1H), 7.58(m, 2H) 7.42(m, 1H), 7.03(dd, 1H), 6.96(d, 1H), 6.88(d, 1H), 6.04(s, 2H), 3.95(m, 2H), 3.31(m, 1H), 2.53(m, 2H), 2.27(m, 2H), 2.07(m, 2H). | 557.1 |
| Example 40 | {5-[4-(4-Benzo[1,3]dioxol-5-yl-5-pyridin-2-yl-1H-imidazol-2-yl)-piperidine-1-sulfonyl]-naphthalen-1-yl}-dimethyl-amine | ¹H NMR(400MHz, CDCl₃): δ 8.61(m, 2H), 8.56(m, 1H), 8.26(d, 1H), 7.80(m, 1H), 7.66(m, 2H), 7.52(m, 2H), 7.39(m, 1H), 6.95(dd, 1H), 6.88(d, 1H), 6.82(d, 1H), 6.01(s, 2H), 3.98(m, 2H), 3.27(m, 1H), 2.75(m, 2H), 2.09(m, 2H), 1.92(m, 2H). | 582.1 |
| Example 41 | 2-{5-Benzo[1,3]dioxol-5-yl-2-[1-(pyridin-4-yl-methyl)-piperidin-4-yl)]-3H-imidazol-4-yl}-pyridine | ¹H NMR(400MHz, CDCl₃): δ 8.82(d, 2H), 8.66(m, 1H), 7.88(d, 2H), 7.78(t, 1H), 7.58(d, 1H), 7.37(m, 1H), 7.06(dd, 1H), 6.98(d, 1H), 6.91(d, 1H), 6.06(s, 2H), 4.43(s, 2H), 4.02(m, 1H), 358(m, 2H), 3.38(m, 2H), 2.30(m, 2H), 1.25(m, 1H), 0.84(m, 1H). | 440.1 |
| Example 42 | 2-{5-Benzo[1,3]dioxol-5-yl-2-[1-(propane-2-sulfonyl)-piperidin-4-yl]-3H-imidazol-4-yl}-pyridine | ¹H NMR(400MHz, MDSO-d₆): δ 8.70(d, 1H), 7.88(t, 1H), 7.46(m, 2H), 7.13(m, 3H), 6.14(s, 2H), 3.80(m, 2H), 3.36(m, 1H), 3.24(m, 1H), 3.05(m, 2H), 2.06(m, 2H), 1.95(m, 2H), 1.24(d, 6H). | 455.0 |
| Example 43 | 2-{5-Benzo[1,3]dioxol-5-yl-2-[1-(4-methoxy-benzenesulfonyl)-piperidin-4-yl]-3H-imidazol-4-yl}-pyridine | ¹H NMR(400MHz, Methanol-d₄): δ 8.67(d, 1H), 7.83(m, 1H), 7.75(d, 2H), 7.45(m, 2H), 7.15(d, 2H), 7.02(m, 3H), 6.08(s, 2H), 3.91(m, 2H), 3.90(s, 3H), 3.04(m, 1H), 2.41(m, 2H), 2.17(m, 2H), 2.04(m, 2H). | 519.1 |
| Example 44 | 1-{4-[4-(4-Benzo[1,3]dioxol-5-yl-5-pyridin-2-yl-1H-imidazol-2-yl)-piperidine-1-sulfonyl]-phenyl}-ethanone | ¹H NMR(400MHz, MDSO-d₆): δ 8.70(d, 1H), 8.21(d, 2H), 7.94(d, 2H), 7.88(t, 1H), 7.44(m, 2H), 7.08(m, 3H), 6.13(s, 2H), 3.85(m, 2H), 3.07(m, 1H), 2.67(s, 3H), 2.44(m, 2H), 2.12(m, 2H), 1.99(m, 2H). | 531.0 |

-continued

| Example | Chemical Name | ¹H-NMR | MS (ES+) m/z (M + 1) |
|---|---|---|---|
| Example 45 | 2-{5-Benzo[1,3]dioxol-5-yl-2-[1-(4-methyl-benzyl)-piperidin-4-yl]-3H-imidazol-4-yl}-pyridine | ¹H NMR(400MHz, MDSO-d₆): δ 8.67(d, 1H), 7.88(t, 1H), 7.43(m, 4H), 7.29(d, 2H), 7.08(m, 3H), 6.11(s, 2H), 4.31(s, 2H), 3.49(m, 2H), 3.26(m, 1H), 3.10(m, 2H), 2.35(s, 3H), 2.29(m, 2H), 2.06(m, 2H). | 453.2 |
| Example 46 | 2-{5-Benzo[1,3]dioxol-5-yl-2-[1-(3-fluoro-5-trifluoromethyl-benzyl)-piperidin-4-yl]-3H-imidazol-4-yl}-pyridine | ¹H NMR(400MHz, MDSO-d₆): δ 8.66(d, 1H), 7.85(m, 3H), 7.75(d, 1H), 7.44(m, 1H), 7.10(m, 3H), 6.11(s, 2H), 4.45(s, 2H), 3.55(m, 2H), 3.27(m, 1H), 3.12(m, 2H), 2.31(m, 2H), 2.08(m, 2H). | 525.1 |
| Example 47 | 2-[5-Benzo[1,3]dioxol-5-yl-2-(1-cyclohexylmethyl-piperidin-4-yl)-3H-imidazol-4-yl]-pyridine | | 445.3 |
| Example 48 | 2-[4-(4-Benzo[1,3]dioxol-5-yl-5-pyridin-2-yl-1H-imidazol-2-yl)-piperidin-1-ylmethyl]-cyclopropanecarboxylic acid ethyl ester | ¹H NMR(400MHz, MDSO-d₆): δ 8.69(d, 1H), 7.90(t, 1H), 7.47(m, 2H), 7.11(m, 3H), 6.12(s, 2H), 4.10(m, 2H), 3.68(m, 2H), 3.20(m, 5H), 2.35(m, 2H), 2.11(m, 2H), 1.81(m, 1H), 1.66(m, 1H), 1.20(m, 4H), 1.06(m, 1H). | 475.2 |
| Example 49 | 2-[4-(4-Benzo[1,3]dioxol-5-yl-5-pyridin-2-yl-1H-imidazol-2-yl)-piperidin-1-ylmethyl]-pyrrolidine-1-carboxylic acid tert-butyl ester | ¹H NMR(400MHz, MDSO-d₆): δ 8.69(d, 1H), 7.91(t, 1H), 7.47(m, 2H), 7.10(m, 3H), 6.12(s, 2H), 4.24(m, 2H), 3.29(m, 8H), 2.33(m, 2H), 1.97(m, 6H), 1.43(s, 9H). | 532.3 |
| Example 50 | 2-{5-Benzo[1,3]dioxol-5-yl-2-[1-(2,2-dimethyl-[1,3]dioxolan-4-ylmethyl)-piperidin-4-yl]-3H-imidazol-4-yl}-pyridine | ¹H NMR(400MHz, MDSO-d₆): δ 8.66(d, 1H), 8.00(m, 1H), 7.57(m, 2H), 7.02(m, 3H), 6.08(s, 2H), 4.59(m, 1H), 4.23(m, 1H), 3.94(m, 1H), 3.80(m, 1H), 3.70(m, 2H), 3.41(m, 2H), 3.27(m, 2H), 2.42(m, 2H), 2.28(m, 2H), 1.47(s, 3H), 2.25(m, 3H). | 463.11 |
| Example 51 | 2-[5-Benzo[1,3]dioxol-5-yl-2-(1-ethanesulfonyl-piperidin-4-yl)-3H-imidazol-4-yl]-pyridine | ¹H NMR(400MHz, CDCl₃): δ 8.63(d, 1H), 7.84(t, 1H), 7.61(d, 1H), 7.44(m, 1H), 7.07(dd, 1H), 6.99(d, 1H), 6.91(d, 1H), 6.06(s, 2H), 3.97(m, 2H), 3.52(m, 1H), 3.02(m, 4H), 2.23(m, 2H), 2.03(m, 2H), 1.37(t, 3H). | 441.1 |
| Example 52 | 2-{5-Benzo[1,3]dioxol-5-yl-2-[1-(butane-1-sulfonyl)-piperidin-4-yl]-3H-imidazol-4-yl}-pyridine | ¹H NMR(400MHz, CDCl₃): δ 8.63(d, 1H), 7.83(t, 1H), 7.59(d, 1H), 7.44(m, 1H), 7.06(dd, 1H), 6.98(d, 1H), 6.90(d, 1H), 6.05(s, 2H), 3.96(m, 2H), 3.53(m, 1H), 2.94(m, 4H), 2.22(m, 2H), 2.02(m, 2H), 1.77(m, 2H), 1.45(m, 2H), 0.95(t, 3H). | 469.2 |
| Example 53 | 2-{5-Benzo[1,3]dioxol-5-yl-2-[1-(2-nitro-phenylmethanesulfonyl)-piperidin-4-yl]-3H-imidazol-4-yl}-pyridine | ¹H NMR(400MHz, CDCl₃): δ 8.62(d, 1H), 8.04(d, 1H), 7.81(m, 1H), 7.67(t, 1H), 7.58(m, 3H), 7.41(m, 1H), 7.06(dd, 1H), 6.99(d, 1H), 6.91(d, 1H), 6.05(s, 2H), 4.79(s, 2H), 3.77(m, 2H), 3.47(m, 1H), 2.90(m, 2H), 2.16(m, 2H), 1.92(m, 2H). | 548.1 |
| Example 54 | 2-{5-Benzo[1,3]dioxol-5-yl-2-[1-(2-phenyl-ethenesulfonyl)-piperidin-4-yl]-3H-imidazol-4-yl}-pyridine | ¹H NMR(400MHz, CDCl₃): δ 8.62(d, 1H), 7.82(t, 1H), 7.60(d, 1H), 7.50(m, 3H), 7.44(m, 4H), 7.05(m, 1H), 6.98(m, 1H), 6.88(d, 1H), 6.70(d, 1H), 6.01(s, 2H), 3.94(m, 2H), 3.45(m, 1H), 2.85(m, 2H), 2.27(m, 2H), 2.10(m, 2H). | 515.2 |
| Example 55 | 2-{5-Benzo[1,3]dioxol-5-yl-2-[1-(propane-1-sulfonyl)-piperidin-4-yl]-3H-imidazol-4-yl}-pyridine | | 455.21 |
| Example 56 | 1-[4-(4-Benzo[1,3]dioxol-5-yl-5-pyridin-2-yl-1H-imidazol-2-yl)-piperidine-1-sulfonylmethyl]-7,7-dimethyl-bicyclo[2.2.1]heptan-2-one | | 563.17 |

-continued

| Example | Chemical Name | ¹H-NMR | MS (ES+) m/z (M + 1) |
|---|---|---|---|
| Example 57 | 2-{5-Benzo[1,3]dioxol-5-yl-2-[1-(4-chloro-phenylmethanesulfonyl)-piperidin-4-yl]-3H-imidazol-4-yl}-pyridine | ¹H NMR(400MHz, Methanol-$d_4$): δ 8.68(m, 1H), 7.83(m, 1H), 7.44(m, 6H), 7.04(m, 3H), 6.08(s, 2H), 4.39(s, 2H), 3.84(m, 2H), 3.21(m, 1H), 2.89(m, 2H), 2.13(m, 2H), 1.93(m, 2H). | 537.11 |
| Example 58 | 2-{5-Benzo[1,3]dioxol-5-yl-2-[1-(3,5-dichloro-phenylmethanesulfonyl)-piperidin-4-yl]-3H-imidazol-4-yl}-pyridine | ¹H NMR(400MHz, Methanol-$d_4$): δ 8.68(m, 1H), 7.84(m, 1H), 7.46(m, 5H), 7.04(m, 3H), 6.08(s, 2H), 4.41(s, 2H), 3.89(m, 2H), 3.26(m, 1H), 2.95(m, 2H), 2.17(m, 2H), 1.96(m, 2H). | 571.04 |
| Example 59 | 2-{5-Benzo[1,3]dioxol-5-yl-2-[1-(4-fluoro-phenylmethanesulfonyl)-piperidin-4-yl]-3H-imidazol-4-yl}-pyridine | ¹H NMR(400MHz, Methanol-$d_4$): δ 8.68(m, 1H), 7.83(t, 1H), 7.47(m, 4H), 7.14(m, 2H), 7.03(m, 3H), 6.08(s, 2H), 4.38(s, 2H), 3.85(m, 2H), 3.21(m, 1H), 2.89(m, 2H), 2.14(m, 2H), 1.92(m, 2H). | 521.10 |
| Example 60 | 2-{5-Benzo[1,3]dioxol-5-yl-2-[1-(3,4-dichloro-phenylmethanesulfonyl)-piperidin-4-yl]-3H-imidazol-4-yl}-pyridine | ¹H NMR(400MHz, Methanol-$d_4$): δ 8.68(m, 1H), 7.84(m, 1H), 7.65(d, 1H), 7.57(d, 1H), 7.44(m, 3H), 7.03(m, 3H), 6.08(s, 2H), 4.40(s, 2H), 3.87(m, 2H), 3.22(m, 1H), 2.93(m, 2H), 2.15(m, 2H), 1.95(m, 2H). | 570.99 |
| Example 61 | 2-{5-Benzo[1,3]dioxol-5-yl-2-[1-(2-phenyl-ethanesulfonyl)-piperidin-4-yl]-3H-imidazol-4-yl}-pyridine | ¹H NMR(400MHz, MDSO-$d_6$): δ 8.70(m, 1H), 7.88(m, 1H), 7.40(m, 6H), 7.13(m, 4H), 6.13(s, 2H), 3.78(m, 2H), 3.39(m, 2H), 3.19(m, 1H), 3.00(m, 4H), 2.09(m, 2H), 1.94(m, 2H). | 517.17 |
| Example 62 | 2-[5-Benzo[1,3]dioxol-5-yl-2-(1-p-tolylmethanesulfonyl-piperidin-4-yl)-3H-imidazol-4-yl]-pyridine | ¹H NMR(400MHz, Methanol-$d_4$): δ 8.57(m, 1H), 7.84(m, 1H), 7.55(m, 1H), 7.44(m, 1H), 7.23(d, 2H), 7.16(d, 2H), 7.01(dd, 1H), 6.95(d, 1H), 6.88(d, 1H), 6.02(s, 2H), 3.74(m, 2H), 3.30(m, 1H), 2.73(m, 2H), 2.08(m, 2H), 1.85(m, 2H). | 517.16 |
| Example 63 | 3-(4-Benzo[1,3]dioxol-5-yl 1-hydroxy-5-pyridin-2-yl-1H-imidazol-2-yl)-piperidine-1-carboxylic acid benzyl ester | ¹H NMR(400MHz, Methanol-$d_4$): δ 8.72(m, 1H), 8.01(m, 1H), 7.59(m, 2H), 7.36(m, 5H), 6.99(m, 3H), 6.06(s, 2H), 5.16(s, 2H), 4.52(m, 1H), 4.23(m, 1H), 3.44(m, 1H), 3.24(m, 1H), 2.99(m, 1H), 2.26(m, 1H), 2.03(m, 1H), 1.90(m, 1H), 1.67(m, 1H). | 499.3 |
| Example 64 | 3-(4-Benzo[1,3]dioxol-5-yl-5-pyridin-2-yl-1H-imidazol-2-yl)-piperidine-1-carboxylic acid benzyl ester | ¹H NMR(400MHz, Methanol-$d_4$): δ 8.67(m, 1H), 7.87(m, 1H), 7.48(m, 2H), 7.34(m, 5H), 7.03(m, 3H), 6.08(s, 2H), 5.16(s, 2H), 4.44(m, 1H), 4.17(m, 1H), 3.22(m, 2H), 3.06(m, 1H), 2.26(m, 1H), 1.95(m, 2H), 1.66(m, 1H). | 483.4 |
| Example 65 | 4-[4-Benzo[1,3]dioxol-5-yl-1-hydroxy-5-(6-methyl-pyridin-2-yl)-1H-imidazol-2-yl]-piperidine-1-carboxylic acid benzyl ester | ¹H NMR(400MHz, Methanol-$d_4$): δ 7.93(t, 1H), 7.50(d, 1H), 7.36(m, 6H), 7.03(m, 2H), 6.98(d, 1H), 6.07(s, 2H), 5.16(s, 2H), 4.36(m, 2H), 3.55(m, 1H), 3.04(m, 2H), 2.66(s, 3H), 2.12(m, 2H), 1.89(m, 2H). | 513.2 |
| Example 66 | 2-{5-Benzo[1,3]dioxol-5-yl-2-[1-(pyridin-2-yl-methanesulfonyl)-piperidin-4-yl]-3H-imidazol-4-yl}-pyridine | ¹H NMR(400MHz, Methanol-$d_4$): δ 8.70(m, 1H), 8.62(m, 1H), 7.98(m, 1H), 7.84(m, 1H), 7.69(d, 1H), 7.51(m, 1H), 7.46(m, 2H), 7.04(m, 3H), 6.08(s, 2H), 4.60(s, 2H), 3.84(m, 2H), 3.22(m, 1H), 2.96(m, 2H), 2.15(m, 2H), 1.96(m, 2H). | 504.11 |
| Example 67 | 2-{5-Benzo[1,3]dioxol-5-yl-2-[1-(2-naphthalen-1-yl-ethanesulfonyl)-piperidin-4-yl]-3H-imidazol-4-yl}-pyridine | ¹H NMR(400MHz, CDCl$_3$): δ 8.62(m, 1H), 8.00(d, 1H), 7.90(d, 1H), 7.79(m, 2H), 7.56(m, 3H), 7.40(m, 3H), 7.06(d, 1H), 7.00(m, 1H), 6.90(d, 1H), 6.02(s, 2H), 3.99(m, 2H), 3.57(m, 2H), 3.50(m, 1H), 3.32(m, 2H), 2.97(m, 2H), 2.23(m, 2H), 1.96(m, 2H). | 567.17 |

-continued

| Example | Chemical Name | ¹H-NMR | MS (ES+) m/z (M + 1) |
|---|---|---|---|
| Example 68 | 2-[5-Benzo[1,3]dioxol-5-yl-2-(1-phenylmethanesulfonyl-piperidin-3-yl)-3H-imidazol-4-yl]-pyridine | ¹H NMR(400MHz, Methanol-$d_4$): δ 8.68(m, 1H), 7.90(m, 1H), 7.44(m, 7H), 7.04(m, 3H), 6.08(s, 2H), 4.40(s, 2H), 3.98(m, 1H), 3.62(m, 1H), 3.26(m, 1H), 3.16(m, 1H), 2.82(m, 1H), 2.21(m, 1H), 1.87(m, 2H), 1.65(m, 1H). | 503.15 |
| Example 69 | 3-[4-Benzo[1,3]dioxol-5-yl-1-hydroxy-5-(6-methyl-pyridin-2-yl)-1H-imidazol-2-yl]-piperidine-1-carboxylic acid benzyl ester | ¹H NMR(400MHz, Methanol-$d_4$): δ 7.59(t, 1H), 7.52(d, 1H), 7.37(m, 6H), 7.01(m, 3H), 6.07(s, 2H), 5.16(s, 2H), 4.50(m, 1H), 4.21(m, 1H), 3.41(m, 1H), 3.27(m, 1H), 3.00(m, 1H), 2.68(s, 3H), 2.25(m, 1H), 2.01(m, 1H), 1.90(m, 1H), 1.67(m, 1H). | 513.2 |
| Example 70 | 2-{5-Benzo[1,3]dioxol-5-yl-2-[1-(pyridin-4-yl-methanesulfonyl)-piperidin-4-yl]-3H-imidazol-4-yl}-pyridine | ¹H NMR(400MHz, Methanol-$d_4$): δ 8.77(d, 2H), 8.69(m, 1H), 7.90(m, 2H), 7.86(m, 1H), 7.46(m, 2H), 7.06(m, 2H), 7.01(d, 1H), 6.09(s, 2H), 4.64(s, 2H), 3.96(m, 2H), 3.27(m, 1H), 3.05(m, 2H), 2.19(m, 2H), 2.00(m, 2H). | 504.11 |
| Example 71 | 2-{5-Benzo[1,3]dioxol-5-yl-2-[1-(pyridin-3-yl-methanesulfonyl)-piperidin-4-yl]-3H-imidazol-4-yl}-pyridine | ¹H NMR(400MHz, Methanol-$d_4$): δ 8.79(d, 1H), 8.73(dd, 1H), 8.68(m, 1H), 8.31(m, 1H), 7.85(m, 1H), 7.79(dd, 1H), 7.46(m, 2H), 7.04(m, 3H), 6.09(s, 2H), 4.58(s, 2H), 3.93(m, 2H), 3.27(m, 1H), 3.03(m, 2H), 2.19(m, 2H), 1.99(m, 2H). | 504.12 |
| Example 72 | 2-{5-Benzo[1,3]dioxol-5-yl-2-[1-(3-trifluoromethyl-phenylmethanesulfonyl)-piperidin-4-yl]-3H-imidazol-4-yl}-pyridine | ¹H NMR(400MHz, Methanol-$d_4$): δ 8.68(m, 1H), 7.70(m, 4H), 7.62(t, 1H), 7.45(m, 2H), 7.03(m, 3H), 6.08(s, 2H), 4.50(s, 2H), 3.89(m, 2H), 3.22(m, 1H), 2.92(m, 2H), 2.14(m, 2H), 1.95(m, 2H). | 571.07 |
| Example 73 | 3-[4-Benzo[1,3]dioxol-5-yl-1-hydroxy-5-(6-methyl-pyridin-2-yl)-1H-imidazol-2-yl]-pyrrolidine-1-carboxylic acid benzyl ester | ¹H NMR(400MHz, Methanol-$d_4$): δ 7.97(t, 1H), 7.52(d, 1H), 7.37(m, 6H), 7.03(m, 2H), 6.98(t, 1H), 6.06(s, 2H), 5.16(s, 2H), 4.03(m, 2H), 3.74(m, 2H), 3.58(m, 1H), 2.66(s, 3H), 2.45(m, 2H). | 499.14 |
| Example 74 | 2-{5-Benzo[1,3]dioxol-5-yl-2-[1-(4-trifluoromethyl-phenylmethanesulfonyl)-piperidin-4-yl]-3H-imidazol-4-yl}-pyridine | | 571.13 |
| Example 75 | 2-{5-Benzo[1,3]dioxol-5-yl-2-[1-(3,5-bis-trifluoromethyl-phenylmethanesulfonyl)-piperidin-4-yl]-3H-imidazol-4-yl}-pyridine | | 639.01 |
| Example 76 | 2-{5-Benzo[1,3]dioxol-5-yl-2-[1-(biphenyl-4-sulfonyl)-piperidin-4-yl]-3H-imidazol-4-yl}-pyridine | ¹H NMR(400MHz, Methanol-$d_4$): δ 8.67(d, 1H), 7.86(m, 5H), 7.68(m, 2H), 7.46(m, 5H), 7.03(m, 3H), 6.08(s, 2H), 3.98(m, 2H), 3.06(m, 1H), 2.50(m, 2H), 2.21(m, 2H), 2.06(m, 2H). | 565.13 |
| Example 77 | 2-{5-Benzo[1,3]dioxol-5-yl-2-[1-(3,5-difluoro-phenylmethanesulfonyl)-piperidin-4-yl]-3H-imidazol-4-yl}-pyridine | ¹H NMR(400MHz, Methanol-$d_4$): δ 8.68(m, 1H), 7.84(m, 1H), 7.46(m, 1H), 7.29(m, 1H), 7.06(m, 6H), 6.08(s, 2H), 4.43(s, 2H), 3.89(m, 2H), 3.24(m, 1H), 2.95(m, 2H), 2.16(m, 2H), 1.96(m, 2H). | 539.10 |
| Example 78 | 2-{5-Benzo[1,3]dioxol-5-yl-2-[1-(pyridin-2-yl-methanesulfonyl)-piperidin-4-yl]-3H-imidazol-4-yl}-6-methyl-pyridine | ¹H NMR(400MHz, Methanol-$d_4$): δ 8.64(d, 1H), 8.00(m, 1H), 7.72(m, 2H), 7.54(m, 1H), 7.33(d, 1H), 7.27(d, 1H), 7.02(m, 3H), 6.07(s, 2H), 4.60(s, 2H), 3.84(m, 2H), 3.23(m, 1H), 2.96(m, 2H), 2.65(s, 3H), 2.15(m, 2H), 1.96(m, 2H). | 518.16 |
| Example 79 | 2-{5-Benzo[1,3]dioxol-5-yl-2-[1-(4-phenoxy-benzenesulfonyl)-piperidin-4-yl]-3H-imidazol-4-yl}-pyridine | ¹H NMR(400MHz, Methanol-$d_4$): δ 8.67(m, 1H), 7.81(m, 3H), 7.46(m, 4H), 7.27(t, 1H), 7.13(m, 4H), 7.03(m, 3H), 6.07(s, 2H), 4.60(s, 2H), 3.84(m, 2H), 3.23(m, 1H), 2.96(m, 2H), 2.15(m, 2H), 1.96(m, 2H). | 581.13 |

-continued

| Example | Chemical Name | ¹H-NMR | MS (ES+) m/z (M + 1) |
|---|---|---|---|
| Example 80 | 2-{5-Benzo[1,3]dioxol-5-yl-2-[1-(biphenyl-4-ylmethanesulfonyl)-piperidin-4-yl]-3H-imidazol-4-yl}-pyridine | ¹H NMR(400MHz, Methanol-d₄): δ 8.67(m, 1H), 7.82(m, 1H), 7.66(m, 4H), 7.56(d, 2H), 7.44(m, 4H), 7.35(t, 1H), 7.02(m, 3H), 6.08(s, 2H), 4.44(s, 2H), 3.87(m, 2H), 3.21(m, 1H), 2.91(m, 2H), 2.11(m, 2H), 1.92(m, 2H). | 579.12 |
| Example 81 | 4-[5-Benzo[1,3]dioxol-5-yl-1-methyl-4-(6-methyl-pyridin-2-yl)-1H-imidazol-2-yl]-piperidine-1-carboxylic acid benzyl ester | ¹H NMR(400MHz, Methanol-d₄): δ 7.77(t, 1H), 7.37(m, 7H), 7.22(d, 1H), 6.83(m, 2H), 6.00(s, 2H), 5.16(s, 2H), 4.37(m, 2H), 3.84(s, 3H), 3.56(m, 1H), 3.09(m, 2H), 2.66(s, 3H), 2.10(m, 2H), 1.88(m, 2H). | 511.4 |
| Example 82 | 4-[4-Benzo[1,3]dioxol-5-yl-1-methyl-5-(6-methyl-pyridin-2-yl)-1H-imidazol-2-yl]-piperidine-1-carboxylic acid benzyl ester | ¹H NMR(400MHz, Methanol-d₄): δ 7.79(t, 1H), 7.36(m, 6H), 7.07(m, 2H), 6.95(m, 2H), 6.11(s, 2H), 5.17(s, 2H), 4.37(m, 2H), 3.60(s, 3H), 3.40(m, 1H), 3.07(m, 2H), 2.69(s, 3H), 2.00(m, 4H). | 511.4 |
| Example 83 | {4-[4-Benzo[1,3]dioxol-5-yl-1-hydroxy-5-(6-methyl-pyridin-2-yl)-1H-imidazol-2-yl]-cyclohexyl}-carbamic acid benzyl ester | ¹H NMR(400MHz, Methanol-d₄): δ 7.90(t, 1H), 7.48(d, 1H), 7.35(m, 6H), 7.01(m, 3H), 6.07(s, 2H), 5.09(s, 2H), 3.52(m, 1H), 2.66(s, 3H), 2.16(m, 3H), 1.99(m, 2H), 1.82(m, 2H), 1.46(m, 2H). | 527.2 |
| Example 84 | 2-{5-Benzo[1,3]dioxol-5-yl-2-[1-(3-phenoxy-phenylmethanesulfonyl)-piperidin-4-yl]-3H-imidazol-4-yl}-6-methyl-pyridine | (400MHz, Methanol-d₄) δ 7.74(t, 1H, J=7.8Hz), 7.20(m, 14H), 6.07(s, 2H), 4.38(s, 2H), 3.85(m, 2H), 3.22(m, 1H), 2.87(m, 2H), 2.66(s, 3H), 2.12(m, 2H), 1.94(m, 2H). | 609.3 |
| Example 85 | 2-[5-Benzo[1,3]dioxol-5-yl-2-(1-ethanesulfonyl-piperidin-4-yl)-3H-imidazol-4-yl]-6-methyl-pyridine | (400MHz, Methanol-d₄) δ 7.74(t, 1H, J=7.9Hz), 7.34(m, 1H), 7.28(m, 1H), 7.03(m, 3H), 6.08(s, 2H), 3.92(m, 2H), 3.25(m, 1H), 2.94(m, 4H), 2.66(s, 3H), 2.23(m, 2H), 2.03(m, 2H), 1.35(t, 3H, J=7.3Hz). | 455.2 |
| Example 86 | 2-{5-Benzo[1,3]dioxol-5-yl-2[1-(propane-1-sulfonyl)-piperidin-4-yl]-3H-imidazol-4-yl}-6-methyl-pyridine | (400MHz, Methanol-d₄) δ 7.74(t, 1H, J=7.9Hz), 7.34(m, 1H), 7.28(m, 1H), 7.03(m, 3H), 6.08(s, 2H), 3.92(m, 2H), 3.25(m, 1H), 2.94(m, 4H), 2.66(s, 3H), 2.23(m, 2H), 2.03(m, 2H), 1.84(m, 2H), 1.09(t, 3H, J=7.3Hz). | 469.2 |
| Example 87 | 2-{5-Benzo[1,3]dioxol-5-yl-2-[1-(butane-1-sulfonyl)-piperidin-4-yl]-3H-imidazol-4-yl}-6-methyl-pyridine | (400MHz, Methanol-d₄) δ 7.74(t, 1H, J=7.9Hz), 7.34(m, 1H), 7.28(m, 1H), 7.03(m, 3H), 6.08(s, 2H), 3.92(m, 2H), 3.25(m, 1H), 2.94(m, 4H), 2.66(s, 3H), 2.23(m, 2H), 2.03(m, 2H), 1.78(m, 2H), 1.50(m, 2H), 0.99(t, 3H, J=7.3Hz). | 483.2 |
| Example 88 | 2-{5-Benzo[1,3]dioxol-5-yl-2-[1-(pyridin-3-ylmethanesulfonyl)-piperidin-4-yl]-3H-imidazol-4-yl}-6-methyl-pyridine | (400MHz, Methanol-d₄) δ 8.75(m, 2H), 8.28(m, 1H), 7.75(m, 2H), 7.32(m, 2H), 7.02(m, 3H), 6.07(s, 2H), 4.54(s, 2H), 3.91(m, 2H), 3.26(m, 1H), 3.03(m, 2H), 2.66(s, 3H), 2.18(m, 2H), 1.99(m, 2H). | 518.1 |
| Example 89 | 2-{5-Benzo[1,3]dioxol-5-yl-2-[1-(pyridin-4-ylmethanesulfonyl)-piperidin-4-yl]-3H-imidazol-4-yl}-6-methyl-pyridine | (400MHz, Methanol-d₄) δ 8.78(m, 2H), 7.94(m, 2H), 7.75(t, 1H, J=7.8Hz), 7.32(m, 2H), 7.02(m, 3H), 6.07(s, 2H), 4.54(s, 2H), 3.91(m, 2H), 3.26(m, 1H), 3.03(m, 2H), 2.66(s, 3H), 2.18(m, 2H), 1.99(m, 2H). | 518.1 |
| Example 90 | 2-{5-Benzo[1,3]dioxol-5-yl-2-[1-(3,5-difluoro-phenylmethanesulfonyl)-piperidin-4-yl]-3H-imidazol-4-yl}-6-methyl-pyridine | (400MHz, Methanol-d₄) δ 7.75(m, 3H), 7.62(t, 1H, J=7.8Hz), 7.34(d, 1H, J=7.8Hz), 7.28(d, 1H, J=7.8Hz), 7.02(m, 3H), 6.07(s, 2H), 4.50(s, 2H), 3.91(m, 2H), 3.26(m, 1H), 3.03(m, 2H), 2.66(s, 3H), 2.18(m, 2H), 1.99(m, 2H). | 553.1 |
| Example 91 | 2-{5-Benzo[1,3]dioxol-5-yl-2-[1-(3-trifluoromethyl-phenylmethanesulfonyl)-piperidin-4-yl]-3H-imidazol-4-yl}-6-methyl-pyridine | (400MHz, Methanol-d₄) δ 7.74(t, 1H, J=7.8Hz), 7.34(d, 1H, J=7.8Hz), 7.28(d, 1H, J=7.8Hz), 7.12(m, 2H), 7.02(m, 4H), 6.07(s, 2H), 4.43(s, 2H), 3.91(m, 2H), 3.26(m, 1H), 3.03(m, 2H), 2.66(s, 3H), 2.18(m, 2H), 1.99(m, 2H). | 585.2 |

-continued

| Example | Chemical Name | ¹H-NMR | MS (ES+) m/z (M + 1) |
|---|---|---|---|
| Example 92 | 2-{5-Benzo[1,3]dioxol-5-yl-2-[1-(thiophene-2-sulfonyl)-piperidin-4-yl]-3H-imidazol-4-yl}-6-methyl-pyridine | (400MHz, Methanol-d$_4$) δ 7.90(m, 1H), 7.74(t, 1H, J=7.8Hz), 7.65(m, 1H), 7.34(m, 1H), 7.27(m, 2H), 7.02(m, 3H), 6.07(s, 2H), 3.91(m, 2H), 3.26(m, 1H), 3.03(m, 2H), 2.66(s, 3H), 2.18(m, 2H), 1.99(m, 2H). | 509.2 |
| Example 93 | 2-{5-Benzo[1,3]dioxol-5-yl-2-[1-(butane-1-sulfonyl)-piperidin-3-yl]-3H-imidazol-4-yl}-6-methyl-pyridine | (400MHz, Methanol-d$_4$) δ7.80(t, 1H, J=7.8Hz), 7.36(m, 2H), 7.03(m, 3H), 6.07(s, 2H), 3.95(m, 1H), 3.60(m, 1H), 3.26(m, 1H), 3.17(m, 1H), 3.08(m, 2H), 2.84(m, 1H), 2.66(s, 3H), 2.20(m, 1H), 1.86(m, 2H), 1.76(m, 2H), 1.64(m, 1H), 1.48(m, 2H), 0.97(t, 3H, J=7.3Hz). | 483.3 |
| Example 94 | 2-[5-Benzo[1,3]dioxol-5-yl-2-(1-phenylmethanesulfonyl-piperidin-3-yl)-3H-imidazol-4-yl]-6-methyl-pyridine | (400MHz, Methanol-d$_4$) δ 7.82(t, 1H, J=7.8Hz), 7.39(m, 7H), 7.02(m, 3H), 6.07(s, 2H), 4.40(s, 2H), 3.95(m, 1H), 3.60(m, 1H), 3.26(m, 1H), 3.17(m, 1H), 2.84(m, 1H), 2.66(s, 3H), 2.20(m, 1H), 1.86(m, 2H), 1.64(m, 1H). | 517.30 |
| Example 95 | 2-{5-Benzo[1,3]dioxol-5-yl-2-[1-(1-methyl-1H-imidazole-4-sulfonyl)-piperidin-4-yl]-3H-imidazol-4-yl}-6-methyl-pyridine | (400MHz, Methanol-d$_4$) δ 7.82(m, 1H), 7.77(m, 1H), 7.73(t, 1H, J=7.8Hz), 7.33(d, 1H, J=7.8Hz), 7.26(d, 1H, J=7.8Hz), 7.02(m, 3H), 6.07(s, 2H), 3.91(m, 2H), 3.82(s, 3H), 3.26(m, 1H), 3.03(m, 2H), 2.66(s, 3H), 2.18(m, 2H), 1.99(m, 2H). | 507.09 |
| Example 96 | 2-{5-Benzo[1,3]dioxol-5-yl-2-[1-(5-methyl-isoxazole-4-sulfonyl)-piperidin-4-yl]-3H-imidazol-4-yl}-6-methyl-pyridine | (400MHz, Methanol-d$_4$) δ 8.67(s, 1H), 7.73(t, 1H, J=7.8Hz), 7.33(d, 1H, J=7.8Hz), 7.26(d, 1H, J=7.8Hz), 7.02(m, 3H), 6.07(s, 2H), 3.91(m, 2H), 3.82(s, 3H), 3.26(m, 1H), 3.03(m, 2H), 2.71(s, 3H), 2.66(s, 3H), 2.18(m, 2H), 1.99(m, 2H). | 508.05 |
| Example 97 | 4-[5-Benzo[1,3]dioxol-5-yl-1-hydroxy-4-(6-methyl-pyridin-2-yl)-1H-imidazol-2-yl]-piperidine-1-carboxylic acid benzyl ester | ¹H NMR(400MHz, Methanol-d$_4$): δ 8.00(t, 1H), 7.48(d, 1H), 7.36(m, 7H), 7.00(m, 2H), 6.07(s, 2H), 5.16(s, 2H), 4.31(m, 2H), 3.35(m, 1H), 3.07(m, 2H), 2.76(s, 3H), 2.05(m, 2H), 1.94(m, 2H). | 513.3 |
| Example 98 | Butane-1-sulfonic acid {4-[4-benzo[1,3]dioxol-5-yl-5-(6-methyl-pyridin-2-yl)-1H-imidazol-2-yl]-cyclohexyl}-amide | (400MHz, Methanol-d$_4$) δ 7.70(m, 1H), 7.28(m, 2H), 7.03(m, 3H), 6.07(s, 2H), 3.08(m, 2H), 3.05(m, 2H), 2.63(s, 3H), 2.13(m, 2H), 1.95(m, 2H), 1.76(m, 2H), 1.72(m, 2H), 1.48(m, 2H), 1.43(m, 2H), 0.98(m, 3H). | 497.2 |
| Example 99 | N-{4-[4-Benzo[1,3]dioxol-5-yl-5-(6-methyl-pyridin-2-yl)-1H-imidazol-2-yl]-cyclohexyl}-C-pyridin-2-yl-methanesulfonamide | (400MHz, Methanol-d$_4$) δ 8.64(m, 1H), 8.03(t, 1H, J=7.8Hz), 7.71(m, 2H), 7.56(m, 1H), 7.31(d, 1H, J=7.8Hz), 7.24(d, 1H, J=7.8Hz),3 7.0(m, 3H), 6.07(s, 2H), 4.60(s, 2H), 3.05(m, 2H), 2.63(s, 3H), 2.13(m, 2H), 1.95(m, 2H), 1.72(m, 2H), 1.43(m, 2H). | 531.9 |
| Example 100 | Thiophene-2-sulfonic acid {4-[4-benzo[1,3]dioxol-5-yl-5-(6-methyl-pyridin-2-yl)-1H-imidazol-2-yl]-cyclohexyl}-amide | (400MHz, CD$_2$Cl$_2$) δ 7.95(t, 1H, J=8.1Hz), 7.62(m, 2H), 7.47(m, 2H), 7.10(m, 1H), 7.02(m, 1H), 6.95(m, 1H), 6.89(m, 1H), 6.07(s, 2H), 3.05(m, 2H), 2.63(s, 3H), 2.13(m, 2H), 1.95(m, 2H), 1.72(m, 2H), 1.43(m, 2H). | 523.2 |
| Example 101 | 1-Methyl-1H-imidazole-4-sulfonic acid {4-[4-benzo[1,3]dioxol-5-yl-5-(6-methyl-pyridin-2-yl)-1H-imidazol-2-yl]-cyclohexyl}-amide | (400MHz, Methanol-d$_4$) δ 7.80(m, 1H), 7.68(m, 2H), 7.29(m, 1H), 7.22(m, 1H), 7.02(m, 3H), 6.07(s, 2H), 3.80(s, 3H), 3.05(m, 2H), 2.63(s, 3H), 2.13(m, 2H), 1.95(m, 2H), 1.72(m, 2H), 1.43(m, 2H). | 521.1 |
| Example 102 | 4-[4-Benzo[1,3]dioxol-5-yl-1-hydroxy-5-(6-methyl-pyridin-2-yl)-1H-imidazol-2-yl]-bicyclo[2.2.2]octane-1-carboxylic acid amide | ¹H NMR(400MHz, Methanol-d$_4$): δ 7.88(t, 1H), 7.48(d, 1H), 7.29(d, 1H), 7.02(m, 3H), 6.08(s, 2H), 2.66(s, 3H), 2.27(m, 6H), 1.97(m, 6H). | 447.14 |

-continued

| Example | Chemical Name | ¹H-NMR | MS (ES+) m/z (M + 1) |
|---|---|---|---|
| Example 103 | 4-[4-Benzo[1,3]dioxol-5-yl-1-hydroxy-5-(6-methyl-pyridin-2-yl)-1H-imidazol-2-yl]-bicyclo[2.2.2]octane-1-carboxylic acid methyl ester | ¹H NMR(400MHz, Methanol-$d_4$): δ 7.87(t, 1H), 7.46(d, 1H), 7.30(d, 1H), 7.04(m, 3H), 3.68(s, 3H), 6.08(s, 2H), 2.66(s, 3H), 2.24(m, 6H), 1.99(m, 6H). | 462.3 |
| Example 104 | 4-[4-Benzo[1,3]dioxol-5-yl-5-(6-bromo-pyridin-2-yl)-1H-imidazol-2-yl]-piperidine-1-carboxylic acid benzyl ester | (400MHz, CDCl$_3$) δ 7.43(d, 1H), 7.37–7.28(m, 6H), 7.26–7.23(m, 1H), 7.05(dd, 1H), 7.04(s, 1H), 6.83(dd, 1H), 5.98(s, 2H), 5.12(s, 2H), 3.07(br, 1H), 2.93(br, 2H), 2.08(d(br), 2H), 1.83(q(br), 2H) | 591.0/593.0 |
| Example 105 | 2-{5-Benzo[1,3]dioxol-5-yl-2-[1-(thiophene-3-sulfonyl)-piperidin-4-yl]-3H-imidazol-4-yl}-6-methyl-pyridine | (400MHz, Methanol-$d_4$) δ 8.15(m, 1H), 7.72(m, 2H), 7.38(d, 1H, J=5.1Hz), 7.33(d, 1H, J=7.8Hz), 7.28(d, 1H, J=7.8Hz), 7.01(m, 3H), 6.07(s, 2H), 3.91(m, 2H), 3.26(m, 1H), 3.03(m, 2H), 2.66(s, 3H), 2.18(m, 2H), 1.99(m, 2H) | 509.0 |
| Example 106 | 2-{5-Benzo[1,3]dioxol-5-yl-2-[1-(5-methyl-2-trifluoromethyl-furan-3-sulfonyl)-piperidin-4-yl]-3H-imidazol-4-yl}-6-methyl-pyridine | (400MHz, Methanol-$d_4$) δ 7.76(m, 1H), 7.30(m, 3H), 7.01(m, 3H), 6.07(s, 2H), 3.91(m, 2H), 3.26(m, 1H), 3.03(m, 2H), 2.66(s, 3H), 2.64(s, 3H), 2.18(m, 2H), 1.99(m, 2H) | 575.2 |
| Example 107 | 4-[2-(1-phenylmethanesulfonyl-piperidin-4-yl)-5-(6-methyl-pyridin-2-yl)-1H-imidazol-4-yl]-pyridin-2-yl-fluoride | (400MHz, CDCl$_3$), d8.29(dd, 1H), 7.96–7.89(m, 1H), 7.50(t, 1H), 7.40–7.37(m, 6H), 7.09(d, 1H), 7.02(d, 1H), 4.23(s, 2H), 3.99(s, 1H), 3.74(d, 2H), 2.86(d, 2H), 2.77(t, 2H), 2.07(m, 2H), 1.94(m, 2H) | 492.4 |
| Example 108 | 4-[4-Benzo[1,3]dioxol-5-yl-5-(6-trifluoromethyl-pyridin-2-yl)-1H-imidazol-2-yl]-piperidine-1-carboxylic acid benzyl ester | (400MHz, CDCl$_3$) δ 7.79(t, 1H), 7.67(d, 1H), 7.58(d, 1H), 7.31–7.21(m, 5H), 7.05(d, 1H), 7.00(s, 1H), 6.83(d, 1H), 5.98(s, 2H), 5.04(d(br), 2H), 4.29(br, 2H), 3.58(br, 1H), 2.92(br, 2H), 2.10–1.80(br, 4H) | 551.2 |
| Example 109 | 4-[5-Benzo[1,3]dioxol-5-yl-4-(6-bromo-pyridin-2-yl)-1-hydroxy-1H-imidazol-2-yl]-piperidine-1-carboxylic acid benzyl ester | (400MHz, MeOH-$d_4$) δ 7.63–7.56(m, 2H), 7.39–7.32(m, 5H), 7.26(d, 1H), 7.02(br, 3H), 6.09(s, 2H), 5.17(s, 2H), 4.36(d(br), 2H), 3.56(br, 1H), 3.06(br, 2H), 2.07–1.99(br, 4H) | 577.0/579.0 |
| Example 110 | 2-5-Benzo[1,3]dioxol-5-yl-2-(1-phenylmethanesulfonyl-piperidin-4-yl)-3H-imidazol-4-yl]-6-bromo-pyridine | (400MHz, CDCl$_3$) δ 7.46–7.35(m, 6H), 7.25(d, 1H), 7.07(d, 1H), 7.05(dd, 1H), 6.84(d, 1H), 5.99(s, 2H), 4.23(s, 2H), 3.71(d(br), 2H), 2.85(br, 1H), 2.72(t(br), 2H), 1.96(d(br), 2H), 1.72(m, 2H) | 580.8/582.8 |
| Example 111 | {4-[4-Benzo[1,3]dioxol-5-yl-5-(6-methyl-pyridin-2-yl)-1H-imidazol-2-yl]-bicyclo[2.2.2]oct-1-yl}-methanol | (300MHz, Methanol-$d_4$) δ 7.71(t, 1H, J=7.8Hz), 7.33(d, 1H, J=7.8Hz), 7.21(d, 1H, J=7.8Hz), 6.97(m, 3H), 6.07(s, 2H), 3.28(s, 2H), 2.64(s, 3H), 2.11(m, 6H), 1.66(m, 6H). | 418.4 |
| Example 112 | 4-[4-Benzo[1,3]dioxol-5-yl-5-(6-methyl-pyridin-2-yl)-1H-imidazol-2-yl]-bicyclo[2.2.2]octane-1-carboxylic acid amide | (300MHz, Methanol-$d_4$) δ 7.70(t, 1H, J=7.8Hz), 7.31(d, 1H, J=7.8Hz), 7.20(d, 1H, J=7.8Hz), 6.97(m, 3H), 6.06(s, 2H), 2.64(s, 3H), 2.11(m, 6H), 1.66(m, 6H). | 431.4 |
| Example 113 | 4-[4-Benzo[1,3]dioxol-5-yl-5-(6-methyl-pyridin-2-yl)-2H-imidazol-2-yl]-piperidine-1-sulfonic acid dimethylamide | (300MHz, Methanol-$d_4$) δ 7.74(t, 1H, J=7.9Hz), 7.34(d, 1H), 7.28(m, 1H), 7.03(m, 3H), 6.07(s, 2H), 3.92(m, 2H), 3.25(m, 1H), 2.94(m, 2H), 2.85(s, 6H), 2.66(s, 3H), 2.23(m, 2H), 2.03(m, 2H). | 470.2 |
| Example 114 | 1-{4-[4-Benzo[1,3]dioxol-5-yl-5-(6-methyl-pyridin-2-yl)-1H-imidazol-2-yl]-piperidin-1-yl}-3-phenyl-propan-1-one | (300MHz, Methanol-$d_4$) δ 7.74(t, 1H, J=7.8Hz), 7.27(m, 7H), 7.03(m, 3H), 6.08(s, 2H), 4.10(m, 2H), 3.89(m, 2H), 3.42(m, 1H), 3.11(m, 2H), 2.92(m, 2H), 2.66(s, 3H), 1.94(m, 4H). | 495.3 |

| Example | Chemical Name | $^1$H-NMR | MS (ES+) m/z (M + 1) |
|---|---|---|---|
| Example 115 | 2-{5-Benzo[1,3]dioxol-5-yl-2-[1-(propane-2-sulfonyl)-piperidin-4-yl]-3H-imidazol-4-yl}-6-methyl-pyridine | (300MHz, Methanol-d$_4$) δ 7.74(t, 1H, J=7.9Hz), 7.34(m, 1H), 7.28(m, 1H), 7.03(m, 3H), 6.07(s, 2H), 3.92(m, 2H), 3.25(m, 2H), 2.94(m, 2H), 2.66(s, 3H), 2.23(m, 2H), 2.03(m, 2H), 1.25(d, 6H, J=9.0Hz). | 470.2 |
| Example 116 | 4-[4-Benzo[1,3]dioxol-5-yl-5-(6-methyl-pyridin-2-yl)-1H-imidazol-2-yl]-bicyclo[2.2.2]octane-1-carbonitrile | (300MHz, Methanol-d$_4$) δ 7.80(t, 1H, J=7.8Hz), 7.38(d, 1H, J=7.8Hz), 7.28(d, 1H, J=7.8Hz), 6.97(m, 3H), 6.06(s, 2H), 2.64(s, 3H), 2.14(m, 12H). | 413.3 |
| Example 117 | 4-[4-Benzo[1,3]dioxol-5-yl-5-(6-methyl-pyridin-2-yl)-1H-imidazol-2-yl]-bicyclo[2.2.2]oct-1-ylamine | (300MHz, Methanol-d$_4$) δ 7.07(m, 6H), 6.05(s, 2H), 2.66(s, 3H), 2.24(m, 6H), 1.98(m, 6H). | 403.4 |
| Example 118 | N-{4-[4-Benzo[1,3]dioxol-5-yl-5-(6-methyl-pyridin-2-yl)-1H-imidazol-2-yl]-bicyclo[2.2.2]oct-1-yl}-C-phenyl-methanesulfonamide | (300MHz, Methanol-d$_4$) δ 7.74(t, 1H, J=7.8Hz), 7.38(m, 6H), 7.23(d, 1H, J=7.8Hz), 6.98(m, 3H), 6.06(s, 2H), 2.65(s, 3H), 2.18(m, 6H), 2.03(m, 6H). | 557.4 |
| Example 119 | N-{4-[4-Benzo[1,3]dioxol-5-yl-5-(6-methyl-pyridin-2-yl)-1H-imidazol-2-yl]-bicyclo[2.2.2]oct-1-yl}-methanesulfonamide | (300MHz, Methanol-d$_4$) δ 7.74(t, 1H, J=7.8Hz), 7.35(d, 1H, J=7.8Hz), 7.23(d, 1H, J=7.8Hz), 6.98(m, 3H), 6.06(s, 2H), 3.01(m, 3H), 2.65(s, 3H), 2.19(m, 6H), 2.10(m, 6H). | 481.6 |
| Example 120 | N-{4-[4-Benzo[1,3]dioxol-5-yl-5-(6-methyl-pyridin-2-yl)-1H-imidazol-2-yl]-bicyclo[2.2.2]oct-1-yl}-C-pyridin-2-yl-methanesulfonamide | (300MHz, Methanol-d$_4$) δ 8.66(d, 1H, J=4.2Hz), 8.09(t, 1H, J=7.8Hz), 7.76(m, 2H), 7.61(m, 1H), 7.36(d, J=7.8Hz), 7.24(d, 1H, J=8.1Hz), 6.98(m, 3H), 6.06(s, 2H), 5.49(s, 1H), 4.60(s, 2H), 2.66(s, 3H), 2.19(m, 6H), 2.12(m, 6H). | 558.4 |
| Example 121 | 2-{5-Benzo[1,3]dioxol-5-yl-2-[4-(1H-tetrazol-5-yl)-bicyclo[2.2.2]oct-1-yl]-3H-imidazol-4-yl}-6-methyl-pyridine | (300MHz, Methanol-d$_4$) δ 7.77(t, 1H, J=7.8Hz), 7.37(d, 1H, J=7.8Hz), 7.27(d, 1H, J=7.8Hz), 7.00(m, 3H), 6.06(s, 2H), 2.66(s, 3H), 2.26(m, 6H), 2.19(m, 6H). | 456.4 |
| Example 122 | N-{4-[4-Benzo[1,3]dioxol-5-yl-5-(6-methyl-pyridin-2-yl)-1H-imidazol-2-yl]-bicyclo[2.2.2]oct-1-yl}-acetamide | (300MHz, CD$_2$Cl$_2$) δ 7.87(t, 1H, J=8.1Hz), 7.38(m, 2H), 6.93(m, 3H), 6.05(s, 2H), 2.74(s, 3H), 2.69(s, 3H), 2.21(m, 6H), 2.08(m, 6H). | 445.6 |
| Example 123 | Thiophene-2-sulfonic acid {4-[4-benzo[1,3]dioxol-5-yl-5-(6-methyl-pyridin-2-yl)-1H-imidazol-2-yl]-bicyclo[2.2.2]oct-1-yl}-amide | (300MHz, Methanol-d$_4$) δ 7.75(m, 2H), 7.61(m, 1H), 7.33(m, 1H), 7.20(m, 1H), 7.11(m, 1H), 6.95(m, 3H), 6.05(s, 2H), 2.64(s, 3H), 2.12(m, 6H), 1.98(m, 6H). | 549.5 |
| Example 124 | 1-Methyl-1H-imidazole-4-sulfonic acid {4-[4-benzo[1,3]dioxol-5-yl-5-(6-methyl-pyridin-2-yl)-1H-imidazol-2-yl]-bicyclo[2.2.2]oct-1-yl}-amide | (300MHz, Methanol-d$_4$) δ 7.74(m, 3H), 7.34(d, 1H, J=7.8Hz), 7.21(d, 1H, J=8.4Hz), 6.05(s, 2H), 3.79(s, 3H), 2.66(s, 3H), 2.56(m, 6H), 1.98(m, 6H). | 547.5 |
| Example 125 | Thiophene-3-sulfonic acid {4-[4-benzo[1,3]dioxol-5-yl-5-(6-methyl-pyridin-2-yl)-1H-imidazol-2-yl]-bicyclo[2.2.2]oct-1-yl}-amide | (300MHz, Methanol-d$_4$) δ 8.05(m, 1H), 7.72(m, 1H), 7.60(m, 1H), 7.37(m, 2H), 7.21(m, 1H), 6.96(m, 3H), 6.05(s, 2H), 2.64(s, 3H), 2.12(m, 6H), 1.94(m, 6H). | 549.5 |
| Example 126 | 2-{5-Benzo[1,3]dioxol-5-yl-2-[1-(2-phenyl-ethenesulfonyl)-piperidin-4-yl]-3H-imidazol-4-yl}-6-methyl-pyridine | (300MHz, Methanol-d$_4$) δ 7.70(m, 3H), 7.46(m, 5H), 7.26(m, 2H), 7.02(m, 4H), 6.07(s, 2H), 3.93(m, 2H), 3.19(m, 1H), 2.87(m, 2H), 2.64(s, 3H), 2.22(m, 2H), 2.04(m, 3H). | 529.8 |
| Example 127 | 2-{5-Benzo[1,3]dioxol-5-yl-2-[1-(2-phenyl-ethanesulfonyl)-piperidin-4-yl]-3H-imidazol-4-yl}-6-methyl-pyridine | (300MHz, Methanol-d$_4$) δ 7.74(m, 1H), 7.31(m, 7H), 7.02(m, 3H), 6.07(s, 2H), 3.95(m, 2H), 3.30(m, 3H), 3.10(m, 2H), 2.99(m, 2H), 2.65(s, 3H), 2.16(m, 2H), 1.98(m, 2H). | 531.8 |
| Example 128 | Methanesulfonic acid 4-[4-benzo[1,3]dioxol-5-yl-5-(6-methyl-pyridin-2-yl)-1H- | (300MHz, Methanol-d$_4$) δ 7.73(t, 1H, J=7.8Hz), 7.34(d, 1H, J=7.8Hz), 7.22(d, 1H, J=7.8Hz), 6.98(m, | 496.5 |

-continued

| Example | Chemical Name | ¹H-NMR | MS (ES+) m/z (M + 1) |
|---|---|---|---|
| | imidazol-2-yl]-bicyclo[2.2.2]oct-1-ylmethyl ester | 3H), 6.06(s, 2H), 3.98(s, 2H), 3.08(s, 3H), 2.65(s, 3H), 2.12(m, 6H), 1.73(m, 6H). | |
| Example 129 | {4-[4-Benzo[1,3]dioxol-5-yl-5-(6-methyl-pyridin-2-yl)-1H-imidazol-2-yl]-bicyclo[2.2.2]oct-1-yl}-acetonitrile | (300MHz, Methanol-d₄) δ 7.73(t, 1H, J=7.8Hz), 7.34(d, 1H, J=7.8Hz), 7.23(d, 1H, J=7.8Hz), 6.98(m, 3H), 6.06(s, 2H), 2.65(s, 3H), 2.40(s, 2H), 2.14(m, 6H), 1.77(m, 6H). | 427.4 |
| Example 130 | {4-[4-Benzo[1,3]dioxol-5-yl-5-(6-methyl-pyridin-2-yl)-1H-imidazol-2-yl]-bicyclo[2.2.2]oct-1-yl}-acetic acid | (300MHz, Methanol-d₄) δ 7.71(t, 1H, J=7.5Hz), 7.33(d, 1H, J=7.8Hz), 7.20(d, 1H, J=8.1Hz), 6.97(m, 3H), 6.06(s, 2H), 2.65(s, 3H), 2.18(s, 2H), 2.09(m, 6H), 1.77(m, 6H). | 446.3 |
| Example 131 | N-{4-[4-Benzo[1,3]dioxol-5-yl-5-(6-methyl-pyridin-2-yl)-1H-imidazol-2-yl]-bicyclo[2.2.2]oct-1-ylmethyl}-methanesulfonamide | (300MHz, Methanol-d₄) δ 8.09(m, 1H), 7.71(m, 1H), 7.34(m, 1H), 7.22(m, 1H), 6.98(m, 2H), 6.85(d, 1H, J=7.5Hz), 6.06(s, 2H), 3.18(s, 3H), 2.92(s, 2H), 2.65(s, 3H), 2.11(m, 6H), 1.67(m, 6H). | 495.5 |
| Example 132 | 2-{5-Benzo[1,3]dioxol-5-yl-2-[1-(biphenyl-4-sulfonyl)-piperidin-4-yl]-3H-imidazol-4-yl}-6-methyl-pyridine | (300MHz, Methanol-d₄) δ 7.90(m, 4H), 7.72(m, 3H), 7.49(m, 3H), 7.32(d, 1H, J=7.8Hz), 7.26(d, 1H, J=8.1Hz), 7.01(m, 3H), 6.07(s, 2H), 4.00(m, 2H), 3.06(m, 1H), 2.63(s, 3H), 2.50(m, 2H), 2.18(m, 2H), 2.06(m, 2H). | 579.7 |
| Example 133 | 2-{5-Benzo[1,3]dioxol-5-yl-2-[1-(4-phenoxy-benzenesulfonyl)-piperidin-4-yl]-3H-imidazol-4-yl}-6-methyl-pyridine | (300MHz, Methanol-d₄) δ 7.77(m, 3H), 7.45(m, 2H), 7.27(m, 1H), 7.12(m, 4H), 7.10(m, 3H), 6.07(s, 2H), 3.95(m, 2H), 3.07(m, 1H), 2.64(s, 3H), 2.46(m, 2H), 2.19(m, 2H), 2.04(m, 2H). | 595.8 |
| Example 134 | 2-{5-Benzo[1,3]dioxol-5-yl-2-[1-(3,4-dichloro-benzenesulfonyl)-piperidin-4-yl]-3H-imidazol-4-yl}-6-methyl-pyridine | (300MHz, Methanol-d₄) δ 7.79(m, 4H), 7.31(m, 2H), 7.01(m, 3H), 6.07(s, 2H), 3.98(m, 2H), 3.09(m, 1H), 2.65(s, 3H), 2.53(m, 3H), 2.53(m, 2H), 2.21(m, 2H), 2.05(m, 2H). | 571.2 |
| Example 135 | N-{4-[4-Benzo[1,3]dioxol-5-yl-5-(6-methyl-pyridin-2-yl)-1H-imidazol-2-yl]-bicyclo[2.2.2]oct-1-ylmethyl}-C-phenyl-methanesulfonamide | (300MHz, Methanol-d₄) δ 7.72(m, 1H), 7.40(m, 6H), 7.22(m, 1H), 6.98(m, 3H), 6.06(s, 2H), 4.54(d, 2H, J=3.3Hz), 4.21(m, 1H), 3.87(s, 2H), 2.64(s, 3H), 2.06(m, 6H), 1.64(m, 6H). | 572.4 |
| Example 136 | N-{4-[4-Benzo[1,3]dioxol-5-yl-5-(6-methyl-pyridin-2-yl)-1H-imidazol-2-yl]-bicyclo[2.2.2]oct-1-ylmethyl}-C-pyridin-2-yl-methanesulfonamide | (300MHz, Methanol-d₄) δ 8.60(m, 1H), 7.92(m, 1H), 7.70(m, 1H), 7.49(m, 1H), 7.34(m, 1H), 7.23(m, 1H), 6.98(m, 3H), 6.06(s, 2H), 4.72(s, 2H), 3.68(s, 2H), 2.65(s, 3H), 2.08(m, 6H), 1.67(m, 6H). | 573.4 |
| Example 137 | 4-[4-Benzo[1,3]dioxol-5-yl-5-(6-methyl-pyridin-2-yl)-1H-imidazol-2-yl]-bicyclo[2.2.2]octane-1-carboxylic acid benzylamide | (300MHz, Methanol-d₄) δ 7.73(m, 1H), 7.29(m, 7H), 6.98(m, 3H), 6.06(s, 2H), 4.39(s, 2H), 2.65(s, 3H), 2.12(m, 6H), 1.99(m, 6H). | 521.6 |
| Example 138 | 4-[4-Benzo[1,3]dioxol-5-yl-5-(6-methyl-pyridin-2-yl)-1H-imidazol-2-yl]-bicyclo[2.2.2]octane-1-carboxylic acid(pyridin-2-ylmethyl)-amide | (300MHz, Methanol-d₄) δ 8.70(m, 1H), 8.37(t, 1H, J=7.8Hz), 7.76(m, 3H), 7.35(d, 1H, J=7.8Hz), 7.24(d, 1H, J=7.8Hz), 6.99(m, 3H), 6.06(s, 2H), 4.64(s, 2H), 2.66(s, 3H), 2.15(m, 1H), 2.03(m, 6H). | 522.7 |
| Example 139 | 4-[4-Benzo[1,3]dioxol-5-yl-5-(6-methyl-pyridin-2-yl)-1H-imidazol-2-yl]-bicyclo[2.2.2]octane-1-carboxylic acid 3-chloro-4-fluoro-benzylamide | (300MHz, Methanol-d₄) δ 7.34(t, 1H, J=7.8Hz), 7.36(m, 2H), 7.19(m, 3H), 6.99(m, 3H), 6.06(s, 2H), 4.33(s, 2H), 2.65(s, 3H), 2.14(m, 6H), 1.98(m, 6H). | 573.3 |
| Example 140 | 4-[4-Benzo[1,3]dioxol-5-yl-5-(6-methyl-pyridin-2-yl)-1H-imidazol-2-yl]-bicyclo[2.2.2]octane-1-carboxylic acid(furan-2-ylmethyl)-amide | (300MHz, Methanol-d₄) δ 7.73(t, 1H, J=7.8Hz), 7.40(d, 1H, J=1.8Hz), 7.34(d, 1H, J=7.8Hz), 7.23(d, 1H, J=7.8Hz), 6.99(m, 3H), 6.33(m, 1H), 6.20(d, 1H, J=3.0Hz), 6.06(s, 2H), 4.36(s, 2H), 2.65(s, 3H), 2.13(m, 6H), 1.97(m, 6H). | 511.7 |

-continued

| Example | Chemical Name | ¹H-NMR | MS (ES+) m/z (M + 1) |
|---|---|---|---|
| Example 141 | 2-[5-Benzo[1,3]dioxol-5-yl-2-(1-methanesulfonyl-pyrrolidin-3-yl)-3H-imidazol-4-yl]-6-methyl-pyridine | (300MHz, Methanol-$d_4$) δ 7.90(t, 1H, J=8.1Hz), 7.42(m, 2H), 7.03(m, 3H), 6.06(s, 2H), 3.86(m, 2H), 3.66(m, 2H), 3.52(m, 1H), 2.97(s, 3H), 2.66(s, 3H), 2.44(m, 2H). | 427.4 |
| Example 142 | 2-{5-Benzo[1,3]dioxol-5-yl-2-[1-(butane-1-sulfonyl)-pyrrolidin-3-yl]-3H-imidazol-4-yl}-6-methyl-pyridine | (300MHz, Methanol-$d_4$) δ 7.89(t, 1H, J=8.1Hz), 7.42(m, 2H), 7.03(m, 3H), 6.06(s, 2H), 3.91(m, 2H), 3.71(m, 2H), 3.55(m, 1H), 3.13(m, 2H), 2.72(s, 3H), 2.49(m, 2H), 1.78(m, 2H), 1.49(m, 2H), 0.97(t, 3H, J=7.5Hz). | 469.5 |
| Example 143 | 2-{5-Benzo[1,3]dioxol-5-yl-2-[1-(1-methyl-1H-imidazole-4-sulfonyl)-pyrrolidin-3-yl]-3H-imidazol-4-yl}-6-methyl-pyridine | (300MHz, Methanol-$d_4$) δ 7.87(t, 1H, J=8.1Hz), 7.78(s, 1H), 7.77(s, 1H), 7.40(m, 2H), 7.02(m, 3H), 6.07(s, 2H), 3.96(m, 1H), 3.77(s, 3H), 3.67(m, 3H), 3.48(m, 1H), 2.66(s, 3H), 2.30(m, 2H). | 493.5 |
| Example 144 | 2-[5-Benzo[1,3]dioxol-5-yl-2-(1-phenylmethanesulfonyl-pyrrolidin-3-yl)-3H-imidazol-4-yl]-6-methyl-pyridine | (300MHz, Methanol-$d_4$) δ 7.90(t, 1H, J=7.8Hz), 7.41(m, 8H), 7.02(m, 3H), 6.07(s, 2H), 4.46(s, 2H), 3.62(m, 5H), 2.71(s, 3H), 3.45(m, 2H). | 503.5 |
| Example 145 | 2-{5-Benzo[1,3]dioxol-5-yl-2-[1-(4-chloro-benzenesulfonyl)-pyrrolidin-3-yl]-3H-imidazol-4-yl}-6-methyl-pyridine | (300MHz, Methanol-$d_4$) δ 7.87(m, 3H), 7.59(m, 2H), 7.41(m, 2H), 6.99(m, 3H), 6.07(s, 2H), 3.82(m, 1H), 3.60(m, 3H), 3.44(m, 1H), 2.72(s, 3H), 2.36(m, 2H). | 523.02 |
| Example 146 | 2-{5-Benzo[1,3]dioxol-5-yl-2-[1-(2-nitro-phenylmethanesulfonyl)-piperidin-4-yl]-3H-imidazol-4-yl}-6-methyl-pyridine | (300MHz, Methanol-$d_4$) δ 8.07(d, 1H, J=8.1Hz), 7.71(m, 4H), 7.34(d, 1H, J=7.8Hz), 7.28(d, 1H, J=8.1Hz), 7.02(m, 3H), 6.07(s, 2H), 4.92(s, 2H), 3.81(m, 2H), 2.65(m, 1H), 2.97(m, 2H), 2.65(s, 3H), 2.15(m, 2H), 1.98(m, 2H). | 562.5 |
| Example 147 | 2-{5-Benzo[1,3]dioxol-5-yl-2-[1-(2-naphthalen-2-yl-ethanesulfonyl)-piperidin-4-yl]-3H-imidazol-4-yl}-6-methyl-pyridine | (300MHz, Methanol-$d_4$) δ 8.07(d, 1H, J=7.8Hz), 7.90(d, 1H, J=8.1Hz), 7.75(m, 2H), 7.48(m, 4H), 7.33(d, 1H, J=7.8Hz), 7.27(d, 1H, J=7.8Hz), 7.02(m, 3H), 6.07(s, 2H), 3.99(m, 2H), 3.58(m, 2H), 3.43(m, 2H), 3.30(m, 1H), 3.01(m, 2H), 2.64(s, 3H), 2.18(m, 2H), 1.97(m, 2H). | 581.6 |
| Example 148 | 1-{4-[4-Benzo[1,3]dioxol-5-yl-5-(6-methyl-pyridin-2-yl)-1H-imidazol-2-yl]-piperidine-1-sulfonylmethyl}-7,7-dimethyl-bicyclo[2.2.1]heptan-2-one | (300MHz, Methanol-$d_4$) δ 7.34(t, 1H, J=7.8Hz), 7.31(m, 2H), 7.03(m, 3H), 6.08(s, 2H), 3.96(m, 2H), 3.38(m, 2H), 2.97(m, 3H), 2.66(s, 3H), 2.44(m, 2H), 2.08(m, 7H), 1.65(m, 1H), 1.47(m, 1H), 1.14(s, 3H), 0.92(s, 3H). | 577.5 |
| Example 149 | 2-{5-Benzo[1,3]dioxol-5-yl-2-[1-(4-chloro-benzenesulfonyl)-piperidin-4-yl]-3H-imidazol-4-yl}-6-methyl-pyridine | (300MHz, Methanol-$d_4$) δ 7.77(m, 5H), 7.30(m, 2H), 7.01(m, 3H), 6.07(s, 2H), 3.97(m, 2H), 3.04(m, 1H), 2.64(s, 3H), 2.47(m, 2H), 2.19(m, 2H), 2.04(m, 2H). | 537.3 |
| Example 150 | 4-[4-Benzo[1,3]dioxol-5-yl-5-(6-methyl-pyridin-2-yl)-1H-imidazol-2-yl]-bicyclo[2.2.2]octane-1-carboxylic acid methylamide | (300MHz, Methanol-$d_4$) δ 7.73(t, 1H, J=7.8Hz), 5.34(d, 1H, J=7.8Hz), 7.23(d, 1H, J=7.8Hz), 6.98(m, 3H), 6.06(s, 2H), 2.73(s, 3H), 2.65(s, 3H), 2.12(m, 6H), 1.94(m, 6H). | 445.5 |
| Example 151 | 4-[4-Benzo[1,3]dioxol-5-yl-5-(6-methyl-pyridin-2-yl)-1H-imidazol-2-yl]-bicyclo[2.2.2]octane-1-carboxylic acid ethylamide | (300MHz, Methanol-$d_4$) δ 7.73(t, 1H, J=7.8Hz), 7.34(d, 1H, J=7.8Hz), 7.23(d, 1H, J=7.8Hz), 6.99(m, 3H), 6.06(s, 2H), 3.21(q, 2H, J=7.2Hz), 2.65(s, 3H), 2.13(m, 6H), 1.95(m, 6H), 1.11(t, 3H, J=7.2Hz). | 459.6 |
| Example 152 | 4-[4-Benzo[1,3]dioxol-5-yl-5-(6-methyl-pyridin-2-yl)-1H-imidazol-2-yl]- | (300MHz, Methanol-$d_4$) δ 7.73(t, 1H, J=7.8Hz), 7.34(d, 1H, J=7.8Hz), 7.23(d, 1H, J=7.8Hz), 6.99(m, | 487.6 |

-continued

| Example | Chemical Name | ¹H-NMR | MS (ES+) m/z (M + 1) |
|---|---|---|---|
| | bicyclo[2.2.2]octane-1-carboxylic acid butylamide | 3H), 6.06(s, 2H), 3.19(t, 2H, J=6.9Hz), 2.65(s, 3H), 2.13(m, 6H), 1.96(m, 6H), 1.48(m, 2H), 1.35(m, 2H), 0.94(t, 1H, J=7.2Hz). | |
| Example 153 | 4-[4-Benzo[1,3]dioxol-5-yl-5-(6-methyl-pyridin-2-yl)-1H-imidazol-2-yl]-bicyclo[2.2.2]octane-1-carboxylic acid isopropylamide | (300MHz, Methanol-d₄) δ 7.73(t, 1H, J=7.8Hz), 7.34(d, 1H, J=7.5Hz), 7.23(d, 1H, J=7.8Hz), 6.06(s, 2H), 4.02(m, 1H), 2.65(m, 1H), 2.12(m, 6H), 1.95(m, 6H), 1.13(d, 6H, J=5.4Hz). | 473.6 |
| Example 154 | 4-[4-Benzo[1,3]dioxol-5-yl-5-(6-methyl-pyridin-2-yl)-1H-imidazol-2-yl]-bicyclo[2.2.2]octane-1-carboxylic acid(3-imidazol-1-yl-propyl)-amide | (300MHz, Methanol-d₄) δ 8.98(s, 1H), 7.71(m, 2H), 7.60(m, 1H), 7.35(d, 1H, J=6.0Hz), 7.24(d, 1H, J=6.0Hz), 6.99(m, 3H), 6.06(s, 2H), 4.26(t, 2H, J=6.0Hz), 4.24(d, 1H, J=6.0Hz), 2.65(s, 3H), 2.13(m, 8H), 1.97(m, 2H). | 539.6 |
| Example 155 | 2-{4-[4-Benzo[1,3]dioxol-5-yl-5-(6-methyl-pyridin-2-yl)-1H-imidazol-2-yl]-piperidine-1-sulfonylmethyl}-phenylamine | (300MHz, Methanol-d₄) δ 7.74(t, 1H, J=7.8Hz),, 7.29(m, 4H), 6.99(m, 5H), 6.06(s, 2H), 4.44(s, 2H), 3.89(m, 2H), 3.22(m, 1H), 2.97(m, 2H), 2.66(s, 3H), 2.13(m, 2H), 1.94(m, 2H). | 532.3 |
| Example 156 | 4-[4-Benzo[1,3]dioxol-5-yl-5-(6-methyl-pyridin-2-yl)-1H-imidazol-2-yl]-bicyclo[2.2.2]octane-1-carboxylic acid(1-methyl-5-methylsulfanyl-1H-[1,2,4]triazol-3-yl)-amide | (300MHz, Methanol-d₄) δ 7.73(t, 1H, J=7.8Hz), 7.35(d, 1H, J=7.8Hz), 7.23(d, 1H, J=7.8Hz), 6.99(d, 3H, J=7.8Hz), 3.70(s, 3H), 2.65(s, 3H), 2.07(m, 12H). | 558.6 |
| Example 157 | 4-[4-Benzo[1,3]dioxol-5-yl-5-(6-methyl-pyridin-2-yl)-1H-imidazol-2-yl]-bicyclo[2.2.2]octane-1-carboxylic acid cyclohexylamide | (300MHz, Methanol-d₄) δ 7.73(t, 1H, J=7.8Hz), 7.34(d, 1H, J=7.8Hz), 7.23(d, 1H, J=7.8Hz), 6.98(m, 3H), 6.06(s, 2H), 3.66(m, 1H), 2.65(s, 3H), 2.12(m, 6H), 1.95(m, 6H), 1.77(m, 5H), 1.29(m, 5H). | 513.9 |
| Example 158 | {4-[4-Benzo[1,3]dioxol-5-yl-5-(6-methyl-pyridin-2-yl)-1H-imidazol-2-yl]-bicyclo[2.2.2]oct-1-yl}-pyrrolidin-1-yl-methanone | (300MHz, Methanol-d₄) δ 7.73(t, 1H, J=7.8Hz), 7.34(d, 1H, J=7.8Hz), 7.23(d, 1H, J=7.8Hz), 6.99(m, 3H), 6.06(s, 2H), 3.47(m, 4H), 2.65(s, 3H), 2.11(m, 12H), 1.87(m, 4H). | 485.8 |
| Example 159 | 4-[4-Benzo[1,3]dioxol-5-yl-5-(6-methyl-pyridin-2-yl)-1H-imidazol-2-yl]-bicyclo[2.2.2]octane-1-carboxylic acid dimethylamide | (300MHz, Methanol-d₄) δ 7.74(t, 1H, J=7.8Hz), 7.35(d, 1H, J=7.8Hz), 7.24(d, 1H, J=7.8Hz), 6.97(m, 3H), 6.06(s, 2H), 3.09(s, 6H), 2.65(s, 3H), 2.13(m, 12H). | 459.5 |
| Example 160 | 4-[4-Benzo[1,3]dioxol-5-yl-5-(6-methyl-pyridin-2-yl)-1H-imidazol-2-yl]-bicyclo[2.2.2]octane-1-carboxylic acid diethylamide | (300MHz, Methanol-d₄) δ 7.73(m 1H), 7.35(d, 1H, J=7.8Hz), 7.23(d, 1H, J=7.8Hz), 6.99(m, 3H), 6.06(s, 2H), 3.47(m, 4H), 2.65(s, 3H), 2.10(m, 12H), 1.17(m, 6H). | 487.4 |
| Example 161 | 4-[4-Benzo[1,3]dioxol-5-yl-5-(6-methyl-pyridin-2-yl)-1H-imidazol-2-yl]-bicyclo[2.2.2]octane-1-carboxylic acid dipropylamide | (300MHz, Methanol-d₄) δ 7.73(t, 1H, J=8.1Hz), 7.34(d, 1H, J=7.5Hz), 7.23(d, 1H, J=8.1Hz__, 6.98(m, 3H), 6.06(s, 2H), 3.36(m, 4H), 2.65(s, 3H), 2.12(m, 12H), 1.61(m, 4H), 0.93(t, 6H, J=7.2Hz). | 515.5 |
| Example 162 | 4-[4-Benzo[1,3]dioxol-5-yl-5-(6-methyl-pyridin-2-yl)-1H-imidazol-2-yl]-bicyclo[2.2.2]octane-1-carboxylic acid(5,7-difluoro-benzothiazol-2-yl)-amide | (300MHz, Methanol-d₄) δ 7.77(t, 1H, J=7.8Hz), 7.50(m, 1H), 7.37(d, 1H, J=7.8Hz), 7.26(d, 1H, J=7.8Hz), 7.03(m, 3H), 6.06(s, 2H), 2.66(s, 3H), 2.17(m, 12H). | 600.5 |
| Example 163 | 4-[4-Benzo[1,3]dioxol-5-yl-5-(6-methyl-pyridin-2-yl)-1H-imidazol-2-yl]-bicyclo[2.2.2]octane-1-carboxylic acid benzothiazol-2-ylamide | (300MHz, Methanol-d₄) δ 7.86(d, 1H, J=8.1Hz), 7.75(m, 2H), 7.34(m, 4H), 6.99(m, 3H), 6.07(s, 2H), 2.66(s, 3H), 2.18(m, 12H). | 564.5 |
| Example 164 | 4-[4-Benzo[1,3]dioxol-5-yl-5-(6-methyl-pyridin-2-yl)-1H-imidazol-2-yl]- | (300MHz, Methanol-d₄) δ 7.78(t, 1H, J=7.8Hz), 7.68(m, 2H), 7.47(m, 2H), 7.37(d, 1H, J=7.8Hz), | 547.5 |

-continued

| Example | Chemical Name | ¹H-NMR | MS (ES+) m/z (M + 1) |
|---|---|---|---|
| | bicyclo[2.2.2]octane-1-carboxylic acid(1H-benzoimidazol-2-yl)-amide | 7.27(d, 1H, J=7.8Hz), 6.99(m, 3H), 6.07(s, 2H), 2.67(s, 3H), 2.21(m, 12H). | |
| Example 165 | 4-[4-Benzo[1,3]dioxol-5-yl-5-(6-methyl-pyridin-2-yl)-1H-imidazol-2-yl]-bicyclo[2.2.2]octane-1-carboxylic acid(2-hydroxy-1-methyl-2-phenyl-ethyl)-amide | (300MHz, Methanol-d₄) δ 7.73(t, 1H, J=7.8Hz), 7.32(m, 7H), 6.98(m, 3H), 6.06(s, 2H), 4.63(d, 1H, J=6.0Hz), 4.19(m, 1H), 2.65(s, 3H), 2.06(m, 6H), 1.80(m, 6H), 1.15(d, 3H, J=6.6Hz). | 565.5 |
| Example 166 | 4-[4-Benzo[1,3]dioxol-5-yl-5-(6-methyl-pyridin-2-yl)-1H-imidazol-2-yl]-bicyclo[2.2.2]octane-1-carboxylic acid(pyridin-4-ylmethyl)-amide | (300MHz, Methanol-d₄) δ 8.79(d, 2H, J=6.6Hz), 7.93(d, 2H, J=6.6Hz), 7.76(t, 1H, J=8.1Hz), 7.36(d, 1H, J=7.8Hz), 7.26(d, 1H, J=7.8Hz), 7.00(m, 3H), 6.06(s, 2H), 4.65(s, 2H), 2.66(s. 3H), 2.18(m, 6H), 2.06(m, 6H). | 565.5 |
| Example 167 | {4-[4-Benzo[1,3]dioxol-5-yl-5-(6-methyl-pyridin-2-yl)-1H-imidazol-2-yl]-piperidin-1-yl}-(3-chloro-phenyl)-methanone | (300MHz, Methanol-d₄) δ 7.64(m, 1H), 7.30(m, 6H), 6.92(m, 3H), 5.98 1.86(m, 4H). 3.21(m, 5H), 2.56(s, 3H), 1.86(m, 4H). | 501.1 |
| Example 168 | {4-[4-Benzo[1,3]dioxol-5-yl-5-(6-methyl-pyridin-2-yl)-1H-imidazol-2-yl]-piperidin-1-yl}-(4-fluoro-phenyl)-methanone | (300MHz, Methanol-d₄) δ 7.74(t, 1H, J=7.8Hz), 7.51(m, 2H), 7.27(m, 4H), 7.03(m, 3H), 6.08(s, 2H), 3.89(m, 2H), 3.42(m, 1H), 3.11(m, 2H), 2.66(s, 3H), 1.94(m, 4H). | 485.5 |
| Example 169 | {4-[4-Benzo[1,3]dioxol-5-yl-5-(6-methyl-pyridin-2-yl)-1H-imidazol-2-yl]-piperidin-1-yl}-(4-methoxy-phenyl)-methanone | (300MHz, Methanol-d₄) δ 7.71(t, 1H, J=7.8Hz), 7.43(m, 2H), 7.31(m, 2H), 7.03(m, 5H), 6.08(s, 2H), 3.85(s, 3H), 3.30(m, 5H), 1.96(m, 4H). | 497.6 |
| Example 170 | 4-[5-Benzo[1,3]dioxol-5-yl-4-(6-cyclopropyl-pyridin-2-yl)-1H-imidazol-2-yl]-bicyclo[2.2.2]octane-1-carboxylic acid | (300MHz, Methanol-d₄) δ 7.68(t, 1H), 7.28(d, 1H), 7.23(d, 1H), 7.04–6.95(m, 3H), 6.07(s, 2H), 2.20–1.97(m, 13H), 1.08–0.99(m, 4H) | 458.1 |
| Example 171 | 4-[5-Benzo[1,3]dioxol-5-yl-4-(6-methyl-pyridin-2-yl)-1H-imidazol-2-yl]-bicyclo[2.2.2]octane-1-carboxylic acid methoxy-amide | (300MHz, Methanol-d₄) δ 7.73(t, 1H, J=8.1Hz), 7.34(d, 1H, J=7.8Hz), 7.23(d, 1H, J=7.8Hz), 6.98(m, 3H), 6.05(s, 2H), 3.67(s, 3H), 2.64(s, 3H), 2.11(m, 6H), 1.94(m, 6H). | 461.3 |
| Example 172 | 4-[5-Benzo[1,3]dioxol-5-yl-4-(6-methyl-pyridin-2-yl)-1H-imidazol-2-yl]-bicyclo[2.2.2]octane-1-carboxylic acid hydroxyamide | (300MHz, Methanol-d₄) δ 7.74(m, 1H), 7.34(m, 1H), 7.23(m, 1H), 6.98(m, 3H), 6.06(m, 2H), 2.65(m, 3H), 2.11(m, 6H), 1.96(m, 6H). | 477.3 |
| Example 173 | {4-[4-Benzo[1,3]dioxol-5-yl-5-(6-methyl-pyridin-2-yl)-1H-imidazol-2-yl]-cyclohexylmethyl}-carbamic acid benzyl ester | (300MHz, Methanol-d₄) δ 7.66(t, 1H, J=7.8Hz), 7.32(m, 7H), 7.02(m, 3H), 6.07(s, 2H), 5.09(s, 2H), 3.12(m, 1H), 3.05(d, 2H, J=6.6Hz), 2.62(s, 3H), 2.17(m, 2H), 1.98(m, 2H), 1.74(m, 2H), 1.62(m, 1H), 1.18(m, 2H). | 525.3 |
| Example 174 | 4-[4-Benzo[1,3]dioxol-5-yl-5-(6-methyl-pyridin-2-yl)-1H-imidazol-2-yl]-bicyclo[2.2.2]octane-1-carboxylic acid hydrazide | (300MHz, Methanol-d₄) δ 7.77(t, 1H, J=8.1Hz), 7.36(d, 1H, J=7.5Hz), 7.26(d, 1H, J=7.8Hz), 7.00(m, 3H), 6.06(s, 2H), 2.66(s, 3H), 2.15(m, 6H), 2.01(m, 6H). | 446.5 |
| Example 175 | N-{4-[4-Benzo[1,3]dioxol-5-yl-5-(6-methyl-pyridin-2-yl)-1H-imidazol-2-yl]-cyclohexylmethyl}-acetamide | (300MHz, Methanol-d₄) δ 7.67(t, 1H, J=7.8Hz), 7.29(d, 1H, J=7.8Hz), 7.22(d, 1H, J=7.8Hz), 7.02(m, 3H), 6.08(s, 2H), 3.09(m, 3H), 2.66(m, 1H), 2.63(s, 3H), 2.18(m, 2H), 2.01(m, 1H), 1.96(s, 3H), 1.75(m, 2H), 1.64(m, 1H), 1.19(m, 2H). | 433.5 |
| Example 176 | N-{4-[4-Benzo[1,3]dioxol-5-yl-5-(6-methyl-pyridin-2-yl)-1H-imidazol-2-yl]-cyclohexylmethyl}-methanesulfonamide | (300MHz, Methanol-d₄) δ 7.66(t, 1H, J=7.8Hz), 7.29(d, 1H, J=7.8Hz), 7.22(d, 1H, J=7.8Hz), 7.02(m, 3H), 6.07(s, 2H), 2.89(s, 3H), 2.62(s, 3H), 2.20 m, 2H), 2.06(m, 2H), 1.73(m, 4H), 1.21(m, 2H). | 469.4 |

-continued

| Example | Chemical Name | ¹H-NMR | MS (ES+) m/z (M + 1) |
|---|---|---|---|
| Example 177 | N-{4-[4-Benzo[1,3]dioxol-5-yl-5-(6-methyl-pyridin-2-yl)-1H-imidazol-2-yl]-cyclohexylmethyl}-C-phenyl-methanesulfonamide | (300MHz, Methanol-$d_4$) δ 7.66(t, 1H, J=7.8Hz), 7.35(m, 8H), 7.02(m, 2H), 6.07(s, 2H), 4.33(s, 2H), 2.83(d, 1H, J=6.3Hz), 2.62(s, 3H), 2.16(m, 2H), 1.98(m, 2H), 1.74(m, 3H), 1.53(m, 1H), 1.15(m, 2H). | 545.5 |
| Example 178 | Butane-1-sulfonic acid {4-[4-benzo[1,3]dioxol-5-yl-5-6-methyl-pyridin-2-yl)-1H-imidazol-2-yl]-cyclohexylmethyl}-amide | (300MHz, Methanol-$d_4$) δ 7.67(m, 1H), 7.29(d, 1H, J=7.8Hz), 7.22(d, 1H, J=7.8Hz), 7.02(m, 1H), 6.07(s, 2H), 3.05(m, 3H), 2.96(d, 1H, J=6.3Hz), 2.63(s, 3H), 2.20(m, 2H), 2.06(m, 2H), 1.75(m, 4H), 1.63(m, 1H), 1.49(m, 2H), 1.20(m, 2H), 0.98(t, 3H, J=6.3Hz). | 511.3 |
| Example 179 | Propane-2-sulfonic acid {4-[4-benzo[1,3]dioxol-5-yl-5-(6-methyl-pyridin-2-yl)-1H-imidazol-2-yl]-cyclohexylmethyl}-amide | (300MHz, Methanol-$d_4$) δ 7.68(m, 1H), 7.29(d, 1H, J=8.1Hz), 7.22(d, 1H, J=7.8Hz), 7.03(m, 3H), 6.07(s, 2H), 3.22(m, 1H), 3.09(m, 1H), 2.99(d, 2H, J=6.3Hz), 2.63(s, 3H), 2.20(m, 2H), 2.06(m, 2H), 1.76(m, 2H), 1.62(m, 1H), 1.34(d, 6H, J=6.6Hz), 1.20(m, 2H). | 497.3 |
| Example 180 | N-{4-[4-Benzo[1,3]dioxol-5-yl-5-(6-methyl-pyridin-2-yl)-1H-imidazol-2-yl]-cyclohexylmethyl}-C-pyridin-2-yl-methanesulfonamide | (300MHz, Methanol-$d_4$) δ 8.64(m, 1H), 8.00(m, 1H), 7.66(m, 2H), 7.54(m, 1H), 7.29(d, 1H, J=7.5Hz), 7.21(d, 1H, J=8.1Hz), 7.01(m, 3H), 6.07(s, 2H), 4.56(s, 2H), 3.08(m, 1H), 2.95(d, 2H, J=6.6Hz), 2.62(s, 3H), 2.19(m, 2H), 2.00(m, 2H), 1.73(m, 2H), 1.60(m, 1H), 1.19(m, 2H). | 546.3 |
| Example 181 | N-{4-[4-Benzo[1,3]dioxol-5-yl-5-(6-methyl-pyridin-2-yl)-1H-imidazol-2-yl]-cyclohexylmethyl}-C-pyridin-4-yl-methanesulfonamide | (300MHz, Methanol-$d_4$) δ 8.76(d, 2H, J=6.3Hz), 7.90(d, 2H, J=6.3Hz), 7.67(t, 1H, J=7.8Hz), 7.29(d, 1H, J=7.8Hz), 7.22(d, 1H, J=7.8Hz), 7.02(m, 3H), 6.07(s, 2H), 4.60(s, 2H), 3.12(m, 1H), 3.01(d, 1H, J=6.6Hz), 2.20(m, 2H), 2.04(m, 2H), 1.73(m, 2H), 1.62(m, 1H), 1.17(m, 2H). | 546.3 |
| Example 182 | (4-Methoxy-benzyl)-{4-[5-(6-methyl-pyridin-2-yl)-2-(1-phenylmethanesulfonyl-piperidin-4-yl)-1H-imidazol-4-yl]-pyridin-2-yl}-amine | (400MHz, Methanol-$d_4$), δ 8.23(d, 1H), 7.87(t, 1H), 7.47–7.31(m, 10H), 7.06(d, 1H), 7.01(s, 1H), 6.89(d, 1H), 4.38(s, 2H), 3.95(s, 3H), 3.78(m, 5H), 2.86(t, 2H), 2.66(m, 3H), 2.10(d, 2H), 1.97(m, 2H) | 609.5 |
| Example 183 | 4-[5-(6-Methyl-pyridin-2-yl)-4-[1,2,4]triazolo[1,5-a]pyridin-6-yl-1H-imidazol-2-yl]-bicyclo[2.2.2]octane-1-carboxylic acid methyl ester | (300MHz, Methanol-$d_4$) δ 9.27(s, 1H), 8.57(s, 1H), 7.93(d, 1H), 7.86(t, 1H), 7.80(dd, 1H), 7.45(dd, 1H), 7.31(d, 1H), 3.72(s, 3H), 2.22–2.15(m, 6H), 2.05–1.97(m, 6H) | 443.3 |
| Example 184 | 4-[5-(6-Methyl-pyridin-2-yl)-4-[1,2,4]triazolo[1,5-a]pyridin-6-yl-1H-imidazol-2-yl]-bicyclo[2.2.2]octane-1-carboxylic acid | (300MHz, Methanol-$d_4$) δ 9.27(s, 1H), 8.57(s, 1H), 7.93(d, 1H), 7.86(t, 1H), 7.81(dd, 1H), 7.44(d, 1H), 7.31(d, 1H), 2.22–2.15(m, 6H), 2.05–1.97(m, 6H) | 429.1 |
| Example 185 | 4-[4-(6-Cyclopropyl-pyridin-2-yl)-5-[1,2,4]triazolo[1,5-a]pyridin-6-yl-1H-imidazol-2-yl]-bicyclo[2.2.2]octane-1-carboxylic acid methyl ester | (300MHz, Methanol-$d_4$) δ 9.19(s, 1H), 8.57(s, 1H), 7.93(d, 1H), 7.79(dd, 1H), 7.76(t, 1H), 7.46(d, 1H), 7.31(d, 1H), 3.72(s, 3H), 2.22–2.03(m, 13H), 0.92–0.87(m, 2H), 0.72–0.69(m, 2H) | 469.3 |
| Example 186 | 4-[4-(6-Methyl-pyridin-2-yl)-5-[1,2,4]triazolo[1,5-a]pyridin-6-yl-1H-imidazol-2-yl]-bicyclo[2.2.2]octane-1-carboxylic acid hydroxyamide | (300MHz, Methanol-$d_4$) δ 9.26(s, 1H), 8.57(s, 1H), 7.93(d, 1H), 7.86(t, 1H), 7.80(dd, 1H), 7.44(dd, 1H), 7.31(d, 1H), 3.72(s, 3H), 2.22–2.15(m, 13H), 2.05–1.95(m, 6H) | 429.3 |
| Example 187 | 4-[4-(6-Methyl-pyridin-2-yl)-5-[1,2,4]triazolo[1,5-a]pyridin-6-yl-1H-imidazol- | (300MHz, Methanol-$d_4$) δ 9.27(s, 1H), 8.57(s, 1H), 7.93(d, 1H), 7.86(t, 1H), 7.80(dd, 1H), 7.45(dd, 1H), | 428.3 |

-continued

| Example | Chemical Name | ¹H-NMR | MS (ES+) m/z (M + 1) |
|---|---|---|---|
| | 2-yl]-bicyclo[2.2.2]octane-1-carboxylic acid amide | 7.31(d, 1H), 3.72(s, 3H), 2.22–2.15(m, 13H), 2.05–1.95(m, 6H) | |
| Example 188 | 4-[4-(6-Cyclopropyl-pyridin-2-yl)-5-[1,2,4]triazolo[1,5-a]pyridin-6-yl-1H-imidazol-2-yl]-bicyclo[2.2.2]octane-1-carboxylic acid | (300MHz, Methanol-$d_4$) δ 9.19(s, 1H), 8.57(s, 1H), 7.93(d, 1H), 7.79(dd, 1H), 7.76(t, 1H), 7.46(d, 1H), 7.31(d, 1H), 2.20–2.03(m, 13H), 0.93–0.87(m, 2H), 0.73–0.69(m, 2H) | 455.4 |
| Example 189 | N-{4-[4-Benzo[1,3]dioxol-5-yl-5-(6-methyl-pyridin-2-yl)-1H-imidazol-2-yl]-bicyclo[2.2.2]oct-1-yl}-2,2,2-trifluoro-acetamide | (300MHz, Methanol-$d_4$) δ 8.60(s, 1H), 7.76(t, 1H, J=7.8Hz), 7.36(d, 1H, J=7.8Hz), 7.25(d, 1H, J=7.8Hz), 7.02(m, 3H), 6.06(s, 2H), 2.66(s, 3H), 2.19(m, 12H). | 499.2 |
| Example 190 | 4-[4-Benzo[1,3]dioxol-5-yl-5-(6-methyl-pyridin-2-yl)-1H-imidazol-2-yl]-bicyclo[2.2.2]octan-1-ol | (300MHz, Methanol-$d_4$) δ 7.72(t, 1H, J=7.8Hz), 7.34(d, 1H, J=7.5Hz), 7.22(d, 1H, J=7.5Hz), 6.98(m, 3H), 6.06(s, 2H), 2.64(s, 3H), 2.21(m, 6H), 1.83(m, 6H). | 404.4 |
| Example 191 | 4-[4-(6-Cyclopropyl-pyridin-2-yl)-5-[1,2,4]triazolo[1,5-a]pyridin-6-yl-1H-imidazol-2-yl]-bicyclo[2.2.2]octane-1-carboxylic acid amide | (300MHz, Methanol-$d_4$) δ 9.20(s, 1H), 8.57(s, 1H), 7.93(d, 1H), 7.79(dd, 1H), 7.76(t, 1H), 7.47(d, 1H), 7.31(d, 1H), 2.23–2.00(m, 13H), 0.91–0.88(m, 2H), 0.71–0.68(m, 2H) | 454.3 |
| Example 192 | 4-[4-(6-Cyclopropyl-pyridin-2-yl)-5-[1,2,4]triazolo[1,5-a]pyridin-6-yl-1H-imidazol-2-yl]-bicyclo[2.2.2]octane-1-carboxylic acid hydroxyamide | (300MHz, Methanol-$d_4$) δ 9.19(s, 1H), 8.57(s, 1H), 7.93(d, 1H), 7.79(dd, 1H), 7.76(t, 1H), 7.46(d, 1H), 7.32(d, 1H), 2.23–1.99(m, 13H), 0.92–0.87(m, 2H), 0.73–0.69(m, 2H) | 470.2 |
| Example 193 | N-{4-[5-Benzo[1,3]dioxol-5-yl-4-(6-methyl-pyridin-2-yl)-1H-imidazol-2-yl]-bicyclo[2.2.2]oct-1-yl}-sulfamide | (300MHz, Methanol-$d_4$) δ 7.75(m, 1H), 7.34(m, 1H), 7.23(m, 1H), 6.98(m, 3H), 6.06(s, 2H), 2.65(s, 3H), 2.15(m, 12H). | 482.4 |
| Example 194 | Sulfamic acid 4-[4-benzo[1,3]dioxol-5-yl-5-(6-methyl-pyridin-2-yl)-1H-imidazol-2-yl]-bicyclo[2.2.2]oct-1-yl ester | (300MHz, Methanol-$d_4$) δ 7.74(t, 1H, J=8.1Hz), 7.36(d, 1H, J=7.5Hz), 7.25(d, 1H, J=7.8Hz), 6.98(m, 3H), 6.06(s, 2H), 2.66(s, 3H), 2.29(m, 12H). | 483.4 |
| Example 195 | {4-[4-(6-Methyl-pyridin-2-yl)-5-quinoxalin-6-yl-1H-imidazol-2-yl]-cyclohexyl}-carbamic acid benzyl ester | (300MHz, Methanol-$d_4$) δ 8.98(m, 2H), 8.38(m, 1H), 8.23(d, 1H, J=8.7Hz), 7.96(m, 1H), 7.73(m, 1H), 7.30(m, 7H), 5.09(s, 2H), 3.55(m, 1H), 3.14(m, 1H), 2.63(s, 3H), 2.07(m, 6H), 1.48(m, 2H). | 519.3 |
| Example 196 | N-{4-[4-Benzo[1,3]dioxol-5-yl-5-(6-methyl-pyridin-2-yl)-1H-imidazol-2-yl]-bicyclo[2.2.2]octane-1-carbonyl}-methanesulfonamide | (300MHz, Methanol-$d_4$) δ 7.75(t, 1H, J=7.8Hz), 7.36(d, 1H, J=7.5Hz), 7.24(d, 1H, J=7.8Hz), 6.98(m, 3H), 6.09(s, 2H), 3.25(s, 3H), 2.66(s, 3H), 2.13(m, 6H), 2.01(m, 6H). | 509.4 |
| Example 197 | N-{4-[4-Benzo[1,3]dioxol-5-yl-5-(6-methyl-pyridin-2-yl)-1H-imidazol-2-yl]-bicyclo[2.2.2]octane-1-carbonyl}-benzenesulfonamide | (300MHz, Methanol-$d_4$) δ 8.01(m, 2H), 7.72(m, 2H), 7.59(m, 2H), 7.35(d, 1H, J=7.5Hz), 7.23(d, 1H, J=7.8Hz), 6.97(m, 3H), 6.06(s, 2H), 2.65(s, 3H), 2.08(m, 6H), 1.89(m, 6H). | 571.3 |
| Example 198 | 4-[5-(3-Methyl-4-oxo-3,4-dihydro-quinazolin-6-yl)-4-(6-methyl-pyridin-2-yl)-1H-imidazol-2-yl]-bicyclo[2.2.2]octane-1-carboxylic acid methyl ester | (300MHz, Methanol-$d_4$) δ 8.50(d, 1H), 8.47(s, 1H), 7.95(d, 1H), 7.82(d, 1H), 7.80(t, 1H), 7.43(d, 1H), 7.31(d, 1H), 3.72(s, 3H), 3.65(s, 3H), 2.67(s, 3H), 2.22–2.16(m, 6H), 2.07–2.01(m, 6H) | 484.3 |
| Example 199 | 4-[5-(3-Methyl-4-oxo-3,4-dihydro-quinazolin-6-yl)-4-(6-methyl-pyridin-2-yl)-1H-imidazol-2-yl]-bicyclo[2.2.2]octane-1-carboxylic acid | (300MHz, Methanol-$d_4$) δ 8.51(d, 1H), 8.48(s, 1H), 7.96(d, 1H), 7.84–7.77(m, 2H), 7.44(d, 1H), 7.32(d, 1H), 3.65(s, 3H), 2.69(s, 3H), 2.22–2.16(m, 6H), 2.07–2.01(m, 6H) | 470.3 |

-continued

| Example | Chemical Name | ¹H-NMR | MS (ES+) m/z (M + 1) |
|---|---|---|---|
| Example 200 | N-{4-[4-(6-Methyl-pyridin-2-yl)-5-quinoxalin-6-yl-1H-imidazol-2-yl]-cyclohexyl}-acetamide | (300MHz, Methanol-$d_4$) δ 8.98(m, 2H), 8.38(d, 1H, J=2.1Hz), 8.23(d, 1H, J=8.7Hz), 7.97(m, 1H), 7.72(t, 1H, J=7.8Hz), 7.35(m, 2H), 3.81(m, 1H), 3.16(m, 1H), 2.65(s, 3H), 2.27(m, 2H), 2.14(m, 2H), 1.99(s, 3H), 1.88(m, 2H), 1.46(m, 2H). | 427.3 |
| Example 201 | 4-[4-(6-Methyl-pyridin-2-yl)-5-quinoxalin-6-yl-1H-imidazol-2-yl]-bicyclo[2.2.2]octane-1-carboxylic acid methyl ester | (300MHz, Methanol-$d_4$) δ 8.87(d, 2H, J=0.6Hz), 8.24(d, 2H, J=1.8Hz), 8.10(d, 1H, J=9.0Hz), 7.82(m, 1H), 7.67(t, 1H, J=7.8Hz), 7.31(d, 1H, J=7.8Hz), 7.21(d, 1H, J=7.8Hz), 3.59(s, 3H), 2.55(s, 3H), 2.07(m, 6H), 1.92(m, 6H). | 454.3 |
| Example 202 | 4-[4-(6-Methyl-pyridin-2-yl)-5-quinoxalin-6-yl-1H-imidazol-2-yl]-bicyclo[2.2.2]octane-1-carboxylic acid | (300MHz, Methanol-$d_4$) δ 8.98(m, 2 H), 8.34(m, 1H), 8.21(d, 1H, J=8.7Hz), 7.92(m, 1H), 7.77(t, 1H, J=7.8Hz), 7.39(d, 1H, J=7.5Hz), 7.31(d, 1H, J=7.8Hz), 2.65(s, 3H), 2.18(m, 6H), 2.04(m, 6H). | 440.3 |
| Example 203 | 4-[4-(6-Methyl-pyridin-2-yl)-5-quinoxalin-6-yl-1H-imidazol-2-yl]-bicyclo[2.2.2]octane-1-carboxylic acid hydroxyamide | (300MHz, Methanol-$d_4$) δ 8.96(m, 2H), 8.34(d, 1H, J=1.8Hz), 8.21(d, 1H, J=8.7Hz), 7.92(m, 1H), 7.78(t, 1H, J=7.8Hz), 7.42(d, 1H, J=7.8Hz), 7.32(d, 1H, J=7.8Hz), 2.18(m, 6H), 2.00(m, 6H). | 455.3 |
| Example 204 | 4-[4-(6-Methyl-pyridin-2-yl)-5-quinoxalin-6-yl-1H-imidazol-2-yl]-bicyclo[2.2.2]octane-1-carboxylic acid amide | (300MHz, Methanol-$d_4$) δ 8.97(m, 2H), 8.34(d, 1H, J=1.8Hz), 8.21(d, 1H, J=9.0Hz), 7.92(m, 1H), 7.77(t, 1H, J=7.8Hz), 7.42(d, 1H, J=7.8Hz), 7.31(d, 1H, J=7.8Hz). | 439.3 |
| Example 205 | N-{4-[4-(6-Methyl-pyridin-2-yl)-5-quinoxalin-6-yl-1H-imidazol-2-yl]-cyclohexyl}-methanesulfonamide | (300MHz, Methanol-$d_4$) δ 8.98(m, 2H), 8.37(d, 1H, J=1.8Hz), 8.24(d, 1H, J=8.7Hz), 7.96(m, 1H), 7.73(t, 1H, J=7.8Hz), 7.38(d, 1H, J=7.8Hz), 7.30(d, 1H, J=7.8Hz), 3.80(m, 1H), 3.12(m, 1H), 2.98(s, 3H), 2.65(s, 3H), 2.27(m, 2H), 1.90(m, 2H), 1.56(m, 2H). | 463.3 |
| Example 206 | 2,2,2-Trifluoro-N-{4-[4-(6-methyl-pyridin-2-yl)-5-quinoxalin-6-yl-1H-imidazol-2-yl]-cyclohexyl}-acetamide | (300MHz, Methanol-$d_4$) δ 8.98(m, 2H), 8.38(d, 1H, J=1.8Hz), 8.24(d, 1H, J=8.7Hz), 7.97(m, 1H), 7.76(t, 1H, J=7.8Hz), 7.38(d, 1H, J=7.8Hz), 7.31(d, 1H, J=7.8Hz). | 481.2 |
| Example 207 | 4-[4-(5-Fluoro-6-methyl-pyridin-2-yl)-5-[1,2,4]triazolo[1,5-a]pyridin-6-yl-1H-imidazol-2-yl]-bicyclo[2.2.2]octane-1-carboxylic acid methyl ester | (300MHz, Methanol-$d_4$) δ 9.29(s, 1H), 8.57(d, 1H), 7.93(dd, 1H), 7.81(dt, 1H), 7.56(td, 1H), 7.45(m, 1H), 3.72(d, 3H), 2.56(t, 3H), 2.23–2.18(m, 6H), 2.08–2.04(m, 6H) | 461.5 |
| Example 208 | {4-[2-[1-(Butane-1-sulfonyl)-piperidin-4-yl]-5-(6-methyl-pyridin-2-yl)-1H-imidazol-4-yl]-pyridin-2-yl}-(4-methoxy-benzyl)-amine | (400MHz, Methanol-d4), δ 7.82(d, 1H), 7.66(t, 1H), 7.30(d, 1H), 7.23–7.18(m, 3H), 6.85(m, 2H), 6.81(s, 1H), 6.78(dd, 1H), 4.36(s, 2H), 3.85(d, 2H), 3.76(s, 3H), 3.05–2.93(m, 5H), 2.53(s, 3H), 2.08(d, 2H), 1.94(ddd, 2H), 1.76(m, 2H), 1.48(m, 2H), 0.97(t, 3H) | 575.3 |
| Example 209 | 4-[2-[1-(Butane-1-sulfonyl)-piperidin-4-yl]-5-(6-methyl-pyridin-2-yl)-1H-imidazol-4-yl]-pyridin-2-ylamine | (400MHz, Methanol-d4), δ 7.81(d, 1H), 7.65(t, 1H), 7.30(d, 1H), 7.19(d, 1H), 6.76(s, 1H), 6.68(dd, 1H), 4.36(s, 2H), 3.84(d, 2H), 3.34(s, 2H), 3.04–2.92(m, 5H), 2.52(s, 3H), 2.06(d, 2H), 1.94(m, 2H), 1.76(m, 2H), 1.48(m, 2H), 0.97(t, 3H) | 455.1 |
| Example 210 | 2-[5-Benzo[1,3]dioxol-5-yl-2-(1-phenylmethanesulfonyl-piperidin-4-yl)-3H-imidazol-4-yl]-6-ethyl-pyridine | 1HNMR(400MHz, Methanol-d4), δ 7.77(t, 1H), 7.54–7.42(m, 6H), 7.37(d, 1H), 7.31(d, 1H), 7.08–7.00(m, 3H), 6.09(s, 2H), 4.42(s, 2H), 3.85(d, 2H), 3.25(m, 1H), 2.94(q, 2H), 2.87(dt, 2H), 2.15(m, 2H), 1.94(ddd, 2H), 1.37(t, 3H) | 531.5 |

-continued

| Example | Chemical Name | $^1$H-NMR | MS (ES+) m/z (M + 1) |
|---|---|---|---|
| Example 211 | 4-[5-(3-Methyl-4-oxo-3,4-dihydro-quinazolin-6-yl)-4-(6-methyl-pyridin-2-yl)-1H-imidazol-2-yl]-bicyclo[2.2.2]octane-1-carboxylic acid amide | 1HNMR(300MHz, Methanol-d4), δ 8.50(d, 1H), 8.45(s, 1H), 7.95(dd, 1H), 7.83–7.77(m, 2H), 7.43(d, 1H), 7.32(d, 1H), 3.65(s, 3H), 2.68(s, 3H), 2.23–2.18(m, 6H), 2.05–2.00(m, 6H), | 469.3 |
| Example 212 | 4-[5-(3-Methyl-4-oxo-3,4-dihydro-quinazolin-6-yl)-4-(6-methyl-pyridin-2-yl)-1H-imidazol-2-yl]-bicyclo[2.2.2]octane-1-carboxylic acid hydroxyamide | 1H NMR(400MHz, Methanol-d4): δ 8.46(d, 1H), 8.39(s, 1H), 7.91(dd, 1H), 7.77(m, 2H), 7.39(d, 1H), 7.27(d, 1H), 3.62(s, 3H), 2.66(s, 3H), 2.16(m, 6H), 1.98(m, 6H). | 485.4 |
| Example 213 | N-{4-[5-(6-Methyl-pyridin-2-yl)-4-quinoxalin-6-yl-1H-imidazol-2-yl]-bicyclo[2.2.2]oct-1-yl}-methanesulfonamide | 1H NMR(400MHz, Methanol-d4): δ 8.97(m, 2H), 8.33(m, 1H), 8.20(d, 1H), 7.92(m, 1H), 7.77(t, 1H), 7.41(d, 1H), 7.31(d, 1H), 2.65(s, 3H), 2.23(m, 6H), 2.14(m, 6H), 1.90(s, 3H). | 453.6 |
| Example 214 | N-{4-[5-(6-Methyl-pyridin-2-yl)-4-quinoxalin-6-yl-1H-imidazol-2-yl]-bicyclo[2.2.2]oct-1-yl}-acetamide | 1H NMR(400MHz, Methanol-d4): δ 8.97(m, 2H), 8.33(m, 1H), 8.21(d, 1H), 7.91(m, 1H), 7.79(t, 1H), 7.42(m, 1H), 7.32(m, 1H), 3.02(s, 3H), 2.63(s, 3H), 2.24(m, 6H), 2.13(m, 6H). | 489.5 |

The TGFβ inhibitory activity of compounds of formula (I) can be assessed by methods described in the following examples.

EXAMPLE 215

Cell-Free Assay for Evaluating Inhibition of Autophosphorylation of TGFβ Type I Receptor The serine-threonine kinase activity of TGFβ type I receptor was measured as the autophosphorylation activity of the cytoplasmic domain of the receptor containing an N-terminal poly histidine, TEV cleavage site-tag, e.g., His-TGFβRI. The His-tagged receptor cytoplasmic kinase domains were purified from infected insect cell cultures using the Gibco-BRL FastBac HTb baculovirus expression system.

To a 96-well Nickel FlashPlate (NEN Life Science, Perkin Elmer) was added 20 μl of 1.25 μCi $^{33}$P-ATP/25 μM ATP in assay buffer (50 mM Hepes, 60 mM NaCl, 1 mM MgCl$_2$, 2 mM DTT, 5 mM MnCl$_2$, 2% glycerol, and 0.015% Brij® 35). 10 μl of each test compound of formula (I) prepared in 5% DMSO solution were added to the FlashPlate. The assay was then initiated with the addition of 20 ul of assay buffer containing 12.5 pmol of His-TGFβRI to each well. Plates were incubated for 30 minutes at room temperature and the reactions were then terminated by a single rinse with TBS. Radiation from each well of the plates was read on a TopCount (Packard). Total binding (no inhibition) was defined as counts measured in the presence of DMSO solution containing no test compound and non-specific binding was defined as counts measured in the presence of EDTA or no-kinase control.

Alternatively, the reaction performed using the above reagents and incubation conditions but in a microcentrifuge tube was analyzed by separation on a 4-20% SDS-PAGE gel and the incorporation of radiolabel into the 40 kDa His-TGFβRI SDS-PAGE band was quantitated on a Storm Phosphoimager (Molecular Dynamics).

Compounds of formula (I) typically exhibited IC$_{50}$ values of less than 10 μM; some exhibited IC$_{50}$ values of less than 1 μM; and some even exhibited IC$_{50}$ values of less than 50 nM.

EXAMPLE 216

Cell-Free Assay for Evaluating Inhibition of Activin Type I Receptor Kinase Activity Inhibition of the Activin type I receptor (Alk 4) kinase autophosphorylation activity by test compounds of formula (I) can be determined in a similar manner to that described above in Example 215 except that a similarly His-tagged form of Alk 4 (His-Alk 4) is used in place of the His-TGFβRI.

EXAMPLE 217

TGFβ Type I Receptor Ligand Displacement FlashPlate Assay 50 nM of tritiated 4-(3-pyridin-2-yl-1H-pyrazol-4-yl)-quinoline (custom-ordered from PerkinElmer Life Science, Inc., Boston, Mass.) in assay buffer (50 mM Hepes, 60 mM NaCl$_2$, 1 MM MgCl$_2$, 5 mM MnCl$_2$, 2 mM 1,4-dithiothreitol (DTT), 2% Brij® 35; pH 7.5) was premixed with a test compound of formula (I) in 1% DMSO solution in a v-bottom plate. Control wells containing either DMSO without any test compound or control compound in DMSO were used. To initiate the assay, His-TGFβ Type I receptor in the same assay buffer (Hepes, NaCl$_2$, MgCl$_2$, MnCl$_2$, DTT, and 30% Brij® added fresh) was added to a nickel coated FlashPlate (PE, NEN catalog number: SMP107), while the control wells contained only buffer (i.e., no His-TGFβ Type I receptor). The premixed solution of tritiated 4-(3-pyridin-2-yl-1H-pyrazol-4-yl)-quinoline and test compound of formula (I) was then added to the wells. The wells were aspirated after an hour at room temperature and radioactivity in wells (emitted from the tritiated compound) was measured using TopCount (PerkinElmer Lifesciences, Inc., Boston Mass.).

Compounds of formula (D) typically exhibited $K_i$ values of less than 10 μM; some exhibited $K_i$ values of less than 1 μM; and some even exhibited $K_i$ values of less than 50 nM.

EXAMPLE 218

Assay for Evaluating Cellular Inhibition of TGFβ Signaling and Cytotoxicity

Biological activity of the compounds of formula (I) was determined by measuring their ability to inhibit TGFβ-induced PAI-Luciferase reporter activity in HepG2 cells.

HepG2 cells were stably transfected with the PAI-luciferase reporter grown in DMEM medium containing 10% FBS, penicillin (100 U/ml), streptomycin (100 μg/ml), L-glutamine (2 mM), sodium pyruvate (1 mM), and non-essential amino acids (1×). The transfected cells were then plated at a concentration of $2.5 \times 10^4$ cells/well in 96 well plates and starved for 3-6 hours in media with 0.5% FBS at 37° C. in a 5% $CO_2$ incubator. The cells were then stimulated with 2.5 ng/ml TGFβ ligand in the starvation media containing 1% DMSO either in the presence or absence of a test compound of formula (I) and incubated as described above for 24 hours. The media was washed out the following day and the luciferase reporter activity was detected using the LucLite Luciferase Reporter Gene Assay kit (Packard, cat. no. 6016911) as recommended. The plates were read on a Wallac Microbeta plate reader, the reading of which was used to determine the $IC_{50}$ values of compounds of formula (I) for inhibiting TGFβ-induced PAI-Luciferase reporter activity in HepG2 cells. Compounds of formula (I) typically exhibited $IC_{50}$ values of less 10 uM.

Cytotoxicity was determined using the same cell culture conditions as described above. Specifically, cell viability was determined after overnight incubation with the CytoLite cell viability kit (Packard, cat. no. 6016901). Compounds of formula (I) typically exhibited $LD_{25}$ values greater than 10 μM.

EXAMPLE 219

Assay for Evaluating Inhibition of TGFβ Type I Receptor Kinase Activity in Cells The cellular inhibition of activin signaling activity by the test compounds of formula (I) is determined in a similar manner as described above in Example 218 except that 100 ng/ml of activin is added to serum starved cells in place of the 2.5 ng/ml TGFβ.

EXAMPLE 220

Assay for TGFβ-Induced Collagen Expression

Preparation of Immortalized Collagen Promotor—Green Fluorescent Protein Cells

Fibroblasts are derived from the skin of adult transgenic mice expressing Green Fluorescent Protein (GFP) under the control of the collagen 1A1 promoter (see Krempen, K. et al., Gene Exp. 8: 151-163 (1999)). Cells are immortalized with a temperature sensitive large T antigen that is in an active stage at 33° C. Cells are expanded at 33° C. and then transferred to 37° C. at which temperature the large T antigen becomes inactive (see Xu, S. et al., Exp. Cell Res. 220: 407-414 (1995)). Over the course of about 4 days and one split, the cells cease proliferating. Cells are then frozen in aliquots sufficient for a single 96 well plate.

Assay of TGFβ-induced Collagen—GFP Expression

Cells are thawed, plated in complete DMEM (contains non-essential amino acids, 1 mM sodium pyruvate and 2 mM L-glutamine) with 10% fetal calf serum, and then incubated for overnight at 37° C., 5% $CO_2$. The cells are trypsinized in the following day and transferred into 96 well format with 30,000 cells per well in 50 μl complete DMEM containing 2% fetal calf serum, but without phenol red. The cells are incubated at 37° C. for 3 to 4 hours to allow them to adhere to the plate. Solutions containing a test compound of formula (I) are then added to wells with no TGFβ (in triplicates), as well as wells with 1 ng/ml TGFβ (in triplicates). DMSO is also added to all of the wells at a final concentration of 0.1%. GFP fluorescence emission at 530 nm following excitation at 485 nm is measured at 48 hours after the addition of solutions containing a test compound on a CytoFluor microplate reader (PerSeptive Biosystems). The data are then expressed as the ratio of TGFβ-induced to non-induced for each test sample.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the following formula:

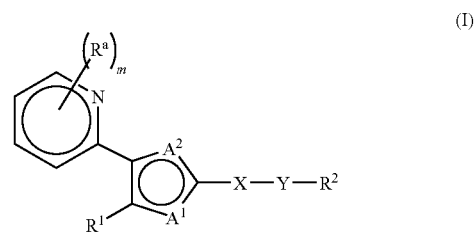

or an N-oxide or a pharmaceutically acceptable salt thereof, wherein $R^1$ is aryl, heteroaryl, aralkyl, or heteroaralkyl;

each $R^a$ is independently alkyl, alkenyl, alkynyl, alkoxy, acyl, halo, hydroxy, amino, nitro, oxo, thioxo, cyano, guanadino, amidino, carboxy, sulfo, mercapto, alkylsulfanyl, alkylsulfinyl, alkylsulfonyl, aminocarbonyl, alkylcarbonylamino, alkylsulfonylamino, alkoxycarbonyl, alkylcarbonyloxy, urea, thiourea, sulfamoyl, sulfamide, carbamoyl, cycloalkyl, cycloalkyloxy, cycloalkylsulfanyl, heterocycloalkyl, heterocycloalkyloxy, heterocycloalkylsulfanyl, aryl, aryloxy, arylsulfanyl, aroyl, heteroaryl, heteroaryloxy, heteroarylsulfanyl, or heteroaroyl;

X is piperidinyl, piperazinyl, pyrrolidinyl, tetrahydrofuran, cyclohexyl, cyclopentyl, bicyclo[2.2.1]heptane, bicyclo[2.2.2]octane, bicyclo[3.2.1]octane, 2-oxa-bicyclo[2.2.2]octane, 2-aza-bicyclo[2.2.2]octane, 3-aza-bicyclo[3.2.1]octane, or 1-aza-bicyclo[2.2.2]octane;

Y is a bond, —C(O)—, —C(O)—O—, —O—C(O)—, —S(O)$_p$—O—, —O—S(O)$_p$—, —C(O)—N(R$^b$)—, —N(R$^b$)—C(O)—, —O—C(O)—N(R$^b$)—, —N(R$^b$)—C(O)—O—, —O—S(O)$_p$—N(R$^b$)—, —N(R$^b$)—S(O)$_p$—O—, —N(R$^b$)—C(O)—N(R$^c$)—, —N(R$^b$)—S(O)$_p$—N(R$^c$)—, —C(O)—N(R$^b$)—S(O)$_p$—, —S(O)$_p$—N(R$^b$)—C(O)—, —C(O)—N(R$^b$)—S(O)$_p$—N(R$^c$)—, —C(O)—O—S(O)$_p$—N(R$^b$)—, —N(R$^b$)—S(O)$_p$—N(R$^c$)—C(O)—, —N(R$^b$)—S(O)$_p$—O—C(O)—, —S(O)$_p$—N(R$^b$)—, —N(R$^b$)—S(O)$_p$—, —N(R$^b$)—, —S(O)$_p$—, —O—, —S—, or —(C(R$^b$)(R$^c$))$_q$—, wherein each of R$^b$ and R$^c$ is independently hydrogen, hydroxy, alkyl, alkoxy, amino, aryl, aralkyl, heterocycloalkyl, heteroaryl, or heteroaralkyl; p is 1 or 2; and q is 1-4;

R$^2$ is hydrogen, alkyl, alkenyl, alkynyl, cycloalkyl, (cycloalkyl)alkyl, cycloalkenyl, (cycloalkenyl)alkyl, aryl, aralkyl, arylalkenyl, heterocycloalkyl, (heterocycloalkyl)alkyl, heterocycloalkenyl, (heterocycloalkenyl)alkyl, heteroaryl, heteroaralkyl, or (heteroaryl)alkenyl;

each of A$^1$ and A$^2$, independently, is O, S, N, or NR$^b$; provided that at least one of A$^1$ and A$^2$ is N; and m is 0, 1, 2, or 3; provided that when m≧2, two adjacent R$^a$ groups can join together to form a 4- to 8-membered optionally substituted cyclic moiety.

2. The compound of claim 1, wherein X is piperidinyl, piperazinyl, or pyrrolidinyl.

3. The compound of claim 2, wherein the piperdinyl, piperazinyl, or pyrrolidinyl is bonded to Y via its nitrogen ring atom.

4. The compound of claim 1, wherein X is cyclohexyl, cyclopentyl, or bicyclo[2.2.2]octane.

5. The compound of claim 4, wherein Y is —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, or —N(R$^b$)—C(O)—N(R$^c$)—.

6. The compound of claim 1, wherein m is 0-2; R$^1$ is aryl or heteroaryl; R$^2$ is hydrogen, C$_{1-6}$ alkyl, aryl, heteroaryl, —C$_{1-4}$ alkyl-aryl, or —C$_{1-4}$ alkyl-heteroaryl; X is piperidinyl, piperazinyl, pyrrolidinyl, tetrahydrofuran, cyclohexyl, cyclopentyl, bicyclo[2.2.1]heptane, bicyclo[2.2.2]octane, bicyclo[3.2.1]octane, 2-oxa-bicyclo[2.2.2]octane, 2-aza-bicyclo[2.2.2]octane, 3-aza-bicyclo[3.2.1]octane, or 1-aza-bicyclo[2.2.2]octane; and Y is —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, —N(R$^b$)—C(O)—N(R$^c$)—, —C(O)—N(R$^b$)—S(O)$_p$—N(R$^c$)—, or —C(O)—O—S(O)$_p$—N(R$^b$)—.

7. The compound of claim 1, wherein m is 0-2; R$^1$ is aryl or heteroaryl; R$^2$ is hydrogen, C$_{1-6}$ alkyl, aryl, heteroaryl, —C$_{1-4}$ alkyl-aryl, or —C$_{1-4}$ alkyl-heteroaryl; and —X—Y— is

[structures]

8. The compound of claim 7, wherein A$^1$ is N and A$^2$ is NH, or A$^1$ is NH and A$^2$ is N.

9. The compound of claim 8, wherein R$^1$ is substituted phenyl.

10. The compound of claim 9, wherein R$^2$ is hydrogen, C$_{1-4}$ alkyl, benzyl, or pyridylmethyl.

11. The compound of claim 10, wherein m is 1 and R$^a$ is is substituted at the 6-position.

12. The compound of claim 1, wherein m is 0-2; R$^1$ is aryl or heteroaryl; R$^2$ is hydrogen, C$_{1-6}$ alkyl, aryl, heteroaryl, aryl-C$_{1-4}$ alkyl, or heteroaryl-C$_{1-4}$ alkyl; X is cyclohexyl, cyclopentyl, or bicyclo[2.2.2]octane; and Y is —N(R$^b$)—C(O)—, —N(R$^b$)—S(O)$_2$—, —C(O)—, —C(O)—O—, —O—C(O)—, —C(O)—N(R$^b$)—, —S(O)$_p$—, —O—, —S(O)$_2$—N(R$^b$)—, —N(R$^b$)—, —N(R$^b$)—C(O)—O—, —N(R$^b$)—C(O)—N(R$^c$)—, —C(O)—N(R$^b$)—S(O)$_p$—N(R$^c$)—, or —C(O)—O—S(O)$_p$—N(R$^b$)—, wherein each of R$^b$ and R$^c$ is independently hydrogen or C$_{1-4}$ alkyl.

13. The compound of claim 12, wherein A$^1$ is N and A$^2$ is NH, or A$^1$ is NH and A$^2$ is N.

14. The compound of claim 13, wherein R$^1$ is a substituted phenyl.

15. The compound of claim 14, wherein R$^2$ is hydrogen, C$_{1-4}$ alkyl, benzyl, or pyridylmethyl.

16. The compound of claim 15, wherein m is 1 and R$^a$ is substituted at the 6-position.

17. The compound of claim 1, said compound being selected from the group consisting of:

4-[4-(4-benzo[1,3]dioxol-5-yl-5-pyridin-2-yl-1H-imidazol-2-yl)-piperidine-1-sulfonyl]-benzoic acid;

2-[5-benzo[1,3]dioxol-5-yl-2-(1-phenylmethanesulfonyl-piperidin-4-yl)-3H-imidazol-4-yl]-pyridine;

2-{5-benzo[1,3]dioxol-5-yl-2-[1-(butane-1-sulfonyl)-piperidin-4-yl]-3H-imidazol-4-yl}-pyridine;

2-{5-benzo[1,3]dioxol-5-yl-2-[1-(3,5-dichloro-phenyl-methanesulfonyl)-piperidin-4-yl]-3H-imidazol-4-yl}-pyridine;

2-{5-benzo[1,3]dioxol-5-yl-2-[1-(4-fluoro-phenyl-methanesulfonyl)-piperidin-4-yl]-3H-imidazol-4-yl}-pyridine;

2-{5-benzo[1,3]dioxol-5-yl-2-[1-(2-phenyl-ethanesulfonyl)-piperidin-4-yl]-3H-imidazol-4-yl}-pyridine;

2-{5-benzo[1,3]dioxol-5-yl-2-[1-(pyridin-2-yl-methanesulfonyl)-piperidin-4-yl]-3H-imidazol-4-yl}-pyridine;

2-[5-benzo[1,3]dioxol-5-yl-2-(1-phenylmethanesulfonyl-piperidin-4-yl)-3H-imidazol-4-yl]-6-methyl-pyridine;

2-{5-benzo[1,3]dioxol-5-yl-2-[1-(3,5-difluoro-phenyl-methanesulfonyl)-piperidin-4-yl]-3H-imidazol-4-yl}-pyridine;

2-{5-benzo[1,3]dioxol-5-yl-2-[1-(pyridin-2-ylmethanesulfonyl)-piperidin-4-yl]-3H-imidazol-4-yl}-6-methyl-pyridine;

2-[5-benzo[1,3]dioxol-5-yl-2-(1-methanesulfonyl-piperidin-4-yl)-3H-imidazol-4-yl]-6-methyl-pyridine;

2-[5-benzo[1,3]dioxol-5-yl-2-(1-ethanesulfonyl-piperidin-4-yl)-3H-imidazol-4-yl]-6-methyl-pyridine;

2-{5-benzo[1,3]dioxol-5-yl-2-[1-(propane-1-sulfonyl)-piperidin-4-yl]-3H-imidazol-4-yl}-6-methyl-pyridine;

2-{5-benzo[1,3]dioxol-5-yl-2-[1-(butane-1-sulfonyl)-piperidin-4-yl]-3H-imidazol-4-yl}-6-methyl-pyridine;

2-{5-benzo[1,3]dioxol-5-yl-2-[1-(pyridin-3-ylmethanesulfonyl)-piperidin-4-yl]-3H-imidazol-4-yl}-6-methyl-pyridine;

2-{5-benzo[1,3]dioxol-5-yl-2-[1-(pyridin-4-ylmethanesulfonyl)-piperidin-4-yl]-3H-imidazol-4-yl}-6-methylpyridine;
2-{5-benzo[1,3]dioxol-5-yl-2-[1-(3,5-difluoro-phenylmethanesulfonyl)-piperidin-4-yl]-3H-imidazol-4-yl}-6-methyl-pyridine;
2-{5-benzo[1,3]dioxol-5-yl-2-[1-(thiophene-2-sulfonyl)-piperidin-4-yl]-3H-imidazol-4-yl}-6-methyl-pyridine;
2-{5-benzo[1,3]dioxol-5-yl-2-[1-(1-methyl-1H-imidazole-4-sulfonyl)-piperidin-4-yl]-3H-imidazol-4-yl}-6-methyl-pyridine;
2-{5-benzo[1,3]dioxol-5-yl-2-[1-(5-methyl-isoxazole-4-sulfonyl)-piperidin-4-yl]-3H-imidazol-4-yl}-6-methyl-pyridine;
N-{4-[4-benzo[1,3]dioxol-5-yl-5-(6-methyl-pyridin-2-yl)-1H-imidazol-2-yl]-cyclohexyl}-C-phenyl-methanesulfonamide;
butane-1-sulfonic acid {4-[4-benzo[1,3]dioxol-5-yl-5-(6-methyl-pyridin-2-yl)-1H-imidazol-2-yl]-cyclohexyl}-amide;
N-{4-[4-benzo[1,3]dioxol-5-yl-5-(6-methyl-pyridin-2-yl)-1H-imidazol-2-yl]-cyclohexyl}-C-pyridin-2-yl-methanesulfonamide;
thiophene-2-sulfonic acid {4-[4-benzo[1,3]dioxol-5-yl-5-(6-methyl-pyridin-2-yl)-1H-imidazol-2-yl]-cyclohexyl}-amide;
1-methyl-1H-imidazole-4-sulfonic acid {4-[4-benzo[1,3]dioxol-5-yl-5-(6-methyl-pyridin-2-yl)-1H-imidazol-2-yl]-cyclohexyl}-amide;
4-[4-benzo[1,3]dioxol-5-yl-5-(6-methyl-pyridin-2-yl)-1H-imidazol-2-yl]-bicyclo[2.2.2]octane-1-carboxylic acid;
2-{5-benzo[1,3]dioxol-5-yl-2-[1-(thiophene-3-sulfonyl)-piperidin-4-yl]-3H-imidazol-4-yl}-6-methyl-pyridine;
4-[4-benzo[1,3]dioxol-5-yl-5-(6-ethyl-pyridin-2-yl)-1H-imidazol-2-yl]-piperidine-1-carboxylic acid benzyl ester;
{4-[4-benzo[1,3]dioxol-5-yl-5-(6-methyl-pyridin-2-yl)-1H-imidazol-2-yl]-bicyclo[2.2.2]oct-1-yl}-methanol;
4-[4-benzo[1,3]dioxol-5-yl-5-(6-methyl-pyridin-2-yl)-1H-imidazol-2-yl]-bicyclo[2.2.2]octane-1-carboxylic acid amide;
2-{5-benzo[1,3]dioxol-5-yl-2-[1-(propane-2-sulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carbonitrile;
2-[5-benzo[1,3]dioxol-5-yl-2-(1-phenylmethanesulfonyl-piperidin-4-yl)-3H-imidazol-4-yl]-6-ethyl-pyridine;
N-{4-[4-benzo[1,3]dioxol-5-yl-5-(6-methyl-pyridin-2-yl)-1H-imidazol-2-yl]-bicyclo[2.2.2]oct-1-yl}-methanesulfonamide;
N-{4-[4-benzo[1,3]dioxol-5-yl-5-(6-methyl-pyridin-2-yl)-1H-imidazol-2-yl]-bicyclo[2.2.2]oct-1-yl}-C-pyridin-2-yl-methanesulfonamide;
2-{5-benzo[1,3]dioxol-5-yl-2-[4-(1H-tetrazol-5-yl)-bicyclo[2.2.2]oct-1-yl]-3H-imidazol-4-yl}-6-methyl-pyridine;
N-{4-[4-benzo[1,3]dioxol-5-yl-5-(6-methyl-pyridin-2-yl)-1H-imidazol-2-yl]-bicyclo[2.2.2]oct-1-yl}-acetamide;
thiophene-2-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
1-methyl-1H-imidazole-4-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
thiophene-3-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
2-{5-benzo[1,3]dioxol-5-yl-2-[1-(2-phenyl-ethanesulfonyl)-piperidin-4-yl]-3H-imidazol-4-yl}-6-methyl-pyridine;
methanesulfonic acid 4-[4-benzo[1,3]dioxol-5-yl-5-(6-methyl-pyridin-2-yl)-1H-imidazol-2-yl]-bicyclo[2.2.2]oct-1-ylmethyl ester;
{4-[4-benzo[1,3]dioxol-5-yl-5-(6-methyl-pyridin-2-yl)-1H-imidazol-2-yl]-bicyclo[2.2.2]oct-1-yl}-acetonitrile;
{4-[4-benzo[1,3]dioxol-5-yl-5-(6-methyl-pyridin-2-yl)-1H-imidazol-2-yl]-bicyclo[2.2.2]oct-1-yl}-acetic acid;
N-{4-[4-benzo[1,3]dioxol-5-yl-5-(6-methyl-pyridin-2-yl)-1H-imidazol-2-yl]-bicyclo[2.2.2]oct-1-ylmethyl}-methanesulfonamide;
N-{4-[4-benzo[1,3]dioxol-5-yl-5-(6-methyl-pyridin-2-yl)-1H-imidazol-2-yl]-bicyclo[2.2.2]oct-1-ylmethyl}-C-pyridin-2-yl-methanesulfonamide;
2-{5-benzo[1,3]dioxol-5-yl-2-[1-(2-nitro-phenylmethanesulfonyl)-piperidin-4-yl]-3H-imidazol-4-yl}-6-methyl-pyridine;
1-{4-[4-benzo[1,3]dioxol-5-yl-5-(6-methyl-pyridin-2-yl)-1H-imidazol-2-yl]-piperidine-1-sulfonylmethyl}-7,7-dimethyl-bicyclo[2.2.1]heptan-2-one;
2-{5-benzo[1,3]dioxol-5-yl-2-[1-(4-chloro-benzenesulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid methylamide;
2-{4-[4-benzo[1,3]dioxol-5-yl-5-(6-methyl-pyridin-2-yl)-1H-imidazol-2-yl ]-piperidine-1-sulfonylmethyl}-phenylamine;
4-[4-benzo[1,3]dioxol-5-yl-5-(6-methyl-pyridin-2-yl)-1H-imidazol-2-yl]-bicyclo[2.2.2]octane-1-carboxylic acid (1-methyl-5-methylsulfanyl-1H-[1,2,4]triazol-3-yl)-amide;
4-[4-benzo[1,3]dioxol-5-yl-5-(6-methyl-pyridin-2-yl)-1H-imidazol-2-yl]-bicyclo[2.2.2]octane-1-carboxylic acid dimethylamide;
{4-[4-benzo[1,3]dioxol-5-yl-5-(6-methyl-pyridin-2-yl)-1H-imidazol-2-yl]-piperidin-1-yl}-(3-chloro-phenyl)-methanone;
4-[5-benzo[1,3]dioxol-5-yl-4-(6-cyclopropyl-pyridin-2-yl)-1H-imidazol-2-yl]-bicyclo[2.2.2]octane-1-carboxylic acid;
4-[5-benzo[1,3]dioxol-5-yl-4-(6-methyl-pyridin-2-yl)-1H-imidazol-2-yl]-bicyclo[2.2.2]octane-1-carboxylic acid methoxy-amide;
4-[5-benzo[1,3]dioxol-5-yl-4-(6-methyl-pyridin-2-yl)-1H-imidazol-2-yl]-bicyclo[2.2.2]octane-1-carboxylic acid hydroxyamide;
{4-[4-benzo[1,3]dioxol-5-yl-5-(6-methyl-pyridin-2-yl)-1H-imidazol-2-yl]-cyclohexylmethyl}-carbamic acid benzyl ester;
4-[4-benzo[1,3]dioxol-5-yl-5-(6-methyl-pyridin-2-yl)-1H-imidazol-2-yl]-bicyclo[2.2.2]octane-1-carboxylic acid hydrazide;
N-{4-[4-benzo[1,3]dioxol-5-yl-5-(6-methyl-pyridin-2-yl)-1H-imidazol-2-yl]-cyclohexylmethyl}-acetamide;
N-{4-[4-benzo[1,3]dioxol-5-yl-5-(6-methyl-pyridin-2-yl)-1H-imidazol-2-yl]-cyclohexylmethyl}-methanesulfonamide;

N-{4-[4-benzo[1,3]dioxol-5-yl-5-(6-methyl-pyridin-2-yl)-1H-imidazol-2-yl]-cyclohexylmethyl}-C-phenyl-methanesulfonamide;

butane-1-sulfonic acid {4-[4-benzo[1,3]dioxol-5-yl-5-(6-methyl-pyridin-2-yl)-1H-imidazol-2-yl]-cyclohexylmethyl}-amide;

propane-2-sulfonic acid {4-[4-benzo[1,3]dioxol-5-yl-5-(6-methyl-pyridin-2-yl)-1H-imidazol-2-yl]-cyclohexylmethyl}-amide;

N-{4-[4-benzo[1,3]dioxol-5-yl-5-(6-methyl-pyridin-2-yl)-1H-imidazol-2-yl]-cyclohexylmethyl}-C-pyridin-2-yl-methanesulfonamide;

N-{4-[4-benzo[1,3]dioxol-5-yl-5-(6-methyl-pyridin-2-yl)-1H-imidazol-2-yl]-cyclohexyl}-methanesulfonamide;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid methyl ester;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid methyl ester;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid;

4-[4-benzo[1,3]dioxol-5-yl-5-(6-methyl-pyridin-2-yl)-1H-imidazol-2-yl]-bicyclo[2.2.2]octan-1-ol;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

N-{4-[4-benzo[1,3]dioxol-5-yl-5-(6-methyl-pyridin-2-yl)-1H-imidazol-2-yl]-bicyclo[2.2.2]oct-1-yl}-sulfamide;

sulfamic acid 4-[4-benzo[1,3]dioxol-5-yl-5-(6-methyl-pyridin-2-yl)-1H-imidazol-2-yl]-bicyclo[2.2.2]oct-1-yl ester;

{4-[4-(6-methyl-pyridin-2-yl)-5-quinoxalin-6-yl-1H-imidazol-2-yl]-cyclohexyl}-carbamic acid benzyl ester;

N-{4-[4-benzo[1,3]dioxol-5-yl-5-(6-methyl-pyridin-2-yl)-1H-imidazol-2-yl]-bicyclo[2.2.2]octane-1-carbonyl}-methanesulfonamide;

N-{4-[4-benzo[1,3]dioxol-5-yl-5-(6-methyl-pyridin-2-yl)-1H-imidazol-2-yl]-bicyclo[2.2.2]octane-1-carbonyl}-benzenesulfonamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid methyl ester;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid;

N-{4-[4-(6-methyl-pyridin-2-yl)-5-quinoxalin-6-yl-1H-imidazol-2-yl]-cyclohexyl}-acetamide;

4-[4-(6-methyl-pyridin-2-yl)-5-quinoxalin-6-yl-1H-imidazol-2-yl]-bicyclo[2.2.2]octane-1-carboxylic acid methyl ester;

4-[4-(6-methyl-pyridin-2-yl)-5-quinoxalin-6-yl-1H-imidazol-2-yl]-bicyclo[2.2.2]octane-1-carboxylic acid;

4-[4-(6-methyl-pyridin-2-yl)-5-quinoxalin-6-yl-1H-imidazol-2-yl]-bicyclo[2.2.2]octane-1-carboxylic acid hydroxyamide;

4-[4-(6-methyl-pyridin-2-yl)-5-quinoxalin-6-yl-1H-imidazol-2-yl]-bicyclo[2.2.2]octane-1-carboxylic acid amide;

N-{4-[4-(6-methyl-pyridin-2-yl)-5-quinoxalin-6-yl-1H-imidazol-2-yl]-cyclohexyl}-methanesulfonamide;

2,2,2-trifluoro-N-{4-[4-(6-methyl-pyridin-2-yl)-5-quinoxalin-6-yl-1H-imidazol-2-yl]-cyclohexyl}-acetamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid amide;

N-{4-[5-(6-methyl-pyridin-2-yl)-4-quinoxalin-6-yl-1H-imidazol-2-yl]-bicyclo[2.2.2]oct-1-yl}-methanesulfonamide;

N-{4-[5-(6-methyl-pyridin-2-yl)-4-quinoxalin-6-yl-1H-imidazol-2-yl]-bicyclo[2.2.2]oct-1-yl}-acetamide;

4-[4-(5-fluoro-6-methyl-pyridin-2-yl)-5-[1,2,4]triazolo[1,5-a]pyridin-6-yl-1H-imidazol-2-yl]-bicyclo[2.2.2]octane-1-carboxylic acid methyl ester;

4-(4-benzo[1,3]dioxol-5-yl-5-pyridin-2-yl-1H-imidazol-2-yl)-piperidine-1-carboxylic acid 4-nitro-benzyl ester;

2-{5-benzo[1,3]dioxol-5-yl-2-[1-(toluene-4-sulfonyl)-piperidin-4-yl]-3H-imidazol-4-yl}-pyridine;

2-{5-benzo[1,3]dioxol-5-yl-2-[1-(4-chloro-benzenesulfonyl)-piperidin-4-yl]-3H-imidazol-4-yl}-pyridine;

2-{5-benzo[1,3]dioxol-5-yl-2-[1-(2-nitro-phenyl-methanesulfonyl)-piperidin-4-yl]-3H-imidazol-4-yl}-pyridine;

2-{5-benzo[1,3]dioxol-5-yl-2-[1-(propane-1-sulfonyl)-piperidin-4-yl]-3H-imidazol-4-yl}-pyridine;

2-{5-benzo[1,3]dioxol-5-yl-2-[l1-(4-chloro-phenyl-methanesulfonyl)-piperidin-4-yl]-3H-imidazol-4-yl}-pyridine;

2-{5-benzo[1,3]dioxol-5-yl-2-[1-(3,4-dichloro-phenyl-methanesulfonyl)-piperidin-4-yl]-3H-imidazol-4-yl}-pyridine;

3-(4-benzo[1,3]dioxol-5-yl-5-pyridin-2-yl-1H-imidazol-2-yl)-piperidine-1-carboxylic acid benzyl ester;

4-[4-benzo[1,3]dioxol-5-yl-5-(6-methyl-pyridin-2-yl)-1H-imidazol-2-yl]-piperidine-1-carboxylic acid benzyl ester;

3-[4-benzo[1,3]dioxol-5-yl-5-(6-methyl-pyridin-2-yl)-1H-imidazol-2-yl]-piperidine-1-carboxylic acid benzyl ester;

2-{5-benzo[1,3]dioxol-5-yl-2-[1-(pyridin-4-ylmethanesulfonyl)-piperidin-4-yl]-3H-imidazol-4-yl-pyridine;

2-{5-benzo[1,3]dioxol-5-yl-2-[1-(pyridin-3-ylmethanesulfonyl)-piperidin-4-yl]-3H-imidazol-4-yl-pyridine;

2-{5-benzo[1,3]dioxol-5-yl-2-[1-(3-trifluoromethyl-phenylmethanesulfonyl)-piperidin-4-yl]-3H-imidazol-4-yl}-pyridine;

3-[4-benzo[1,3]dioxol-5-yl-1-hydroxy-5-(6-methyl-pyridin-2-yl)-1H-imidazol-2-yl]-pyrrolidine-1-carboxylic acid benzyl ester;

{4-[4-benzo[1,3]dioxol-5-yl-5-(6-methyl-pyridin-2-yl)-1H-imidazol-2-yl]-cyclohexyl}-carbamic acid benzyl ester;

2-{5-benzo[1,3]dioxol-5-yl-2-[1-(3-trifluoromethyl-phenylmethanesulfonyl)-piperidin-4-yl]-3H-imidazol-4-yl}-6-methyl-pyridine;

2-{5-benzo[1,3]dioxol-5-yl-2-[1-(butane-1-sulfonyl)-piperidin-3-yl]-3H-imidazol-4-yl}-6-methyl-pyridine;

2-[5-benzo[1,3]dioxol-5-yl-2-(1-phenylmethanesulfonyl-piperidin-3-yl)-3H-imidazol-4-yl]-6-methyl-pyridine;
{4-[2-[1-(butane-1-sulfonyl)-piperidin-4-yl]-5-(6-methyl-pyridin-2-yl)-1H-imidazol-4-yl]-pyridin-2-yl}-(4-methoxy-benzyl)-amine;
4-[2-[1-(butane-1-sulfonyl)-piperidin-4-yl]-5-(6-methyl-pyridin-2-yl)-1H-imidazol-4-yl]-pyridin-2-ylamine;
4-[4-benzo[1,3]dioxol-5-yl-5-(6-methyl-pyridin-2-yl)-1H-imidazol-2-yl]-bicyclo[2.2.2]octane-1-carboxylic acid methyl ester;
2-{5-benzo[1,3]dioxol-5-yl-2-[1-(5-methyl-2-trifluoromethyl-furan-3-sulfonyl-piperidin-4-yl]-3H-imidazol-4-yl}-6-methyl-pyridine;
4-[2-(1-phenylmethanesulfonyl-piperidin-4-yl)-5-(6-methyl-pyridin-2-yl)-1H-imidazol-4-yl]-pyridin-2-ylfluoride;
(4-methoxy-benzyl)-{4-[5-(6-methyl-pyridin-2-yl)-2-(1-phenylmethanesulfonyl-piperidin-4-yl)-1H-imidazol-4-yl]-pyridin-2-yl}-amine;
{4-[4-benzo[1,3]dioxol-5-yl-5-(6-methyl-pyridin-2-yl)-1H-imidazol-2-yl]-bicyclo[2.2.2]oct-1-yl}-carbamic acid benzyl ester;
2-[5-benzo[1,3]dioxol-5-yl-2-(1-phenylmethanesulfonyl-piperidin-4-yl)-3H-imidazol-4-yl]-6-bromo-pyridine;
1-{4-[4-benzo[1,3]dioxol-5-yl-5-(6-methyl-pyridin-2-yl)-1H-imidazol-2-yl]-piperidin-1-yl}-3-phenyl-propan-1-one;
N-{4-[4-benzo[1,3]dioxol-5-yl-5-(6-methyl-pyridin-2-yl)-1H-imidazol-2-yl]-bicyclo[2.2.2]oct-1-yl}-C-phenyl-methanesulfonamide;
2-{5-benzo[1,3]dioxol-5-yl-2-[1-(2-phenyl-ethenesulfonyl)-piperidin-4-yl]-3H-imidazol-4-yl}-6-methyl-pyridine;
2-{5-benzo[1,3]dioxol-5-yl-2-[1-(3,4-dichloro-benzenesulfonyl)-piperidin-4-yl]-3H-imidazol-4-yl}-6-methyl-pyridine;
N-{4-[4-benzo[1,3]dioxol-5-yl-5-(6-methyl-pyridin-2-yl)-1H-imidazol-2-yl]-bicyclo[2.2.2]oct-1-ylmethyl}-C-phenyl-methanesulfonamide;
4-[4-benzo[1,3]dioxol-5-yl-5-(6-methyl-pyridin-2-yl)-1H-imidazol-2-yl]-bicyclo[2.2.2]octane-1-carboxylic acid (pyridin-2-ylmethyl)-amide;
4-[4-benzo[1,3]dioxol-5-yl-5-(6-methyl-pyridin-2-yl)-1H-imidazol-2-yl]-bicyclo[2.2.2]octane-1-carboxylic acid (furan-2-ylmethyl)-amide;
2-[5-benzo[1,3]dioxol-5-yl-2-(1-methanesulfonyl-pyrrolidin-3-yl)-3H-imidazol-4-yl]-6-methyl-pyridine;
2-{5-benzo[1,3]dioxol-5-yl-2-[1-(butane-1-sulfonyl)-pyrrolidin-3-yl]-3H-imidazol-4-yl}-6-methyl-pyridine;
2-{5-benzo[1,3]dioxol-5-yl-2-[1-(1-methyl-1H-imidazole-4-sulfonyl)-pyrrolidin-3-yl]-3H-imidazol-4-yl}-6-methyl-pyridine;
2-[5-benzo[1,3]dioxol-5-yl-2-(1-phenylmethanesulfonyl-pyrrolidin-3-yl)-3H-imidazol-4-yl]-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid ethylamide;
4-[4-benzo[1,3]dioxol-5-yl-5-(6-methyl-pyridin-2-yl)-1H-imidazol-2-yl]-bicyclo[2.2.2]octane-1-carboxylic acid butylamide;
4-[4-benzo[1,3]dioxol-5-yl-5-(6-methyl-pyridin-2-yl)-1H-imidazol-2-yl]-bicyclo[2.2.2]octane-1-carboxylic acid isopropylamide;
4-[4-benzo[1,3]dioxol-5-yl-5-(6-methyl-pyridin-2-yl)-1H-imidazol-2-yl]-bicyclo[2.2.2]octane-1-carboxylic acid (3-imidazol-1-yl-propyl)-amide;
{4-[4-benzo[1,3]dioxol-5-yl-5-(6-methyl-pyridin-2-yl)-1H-imidazol-2-yl]-bicyclo[2.2.2]oct-1-yl}-pyrrolidin-1-yl-methanone;
4-[4-benzo[1,3]dioxol-5-yl-5-(6-methyl-pyridin-2-yl)-1H-imidazol-2-yl]-bicyclo[2.2.2]octane-1-carboxylic acid diethylamide;
4-[4-benzo[1,3]dioxol-5-yl-5-(6-methyl-pyridin-2-yl)-1H-imidazol-2-yl]-cyclohexylamine;
{4-[4-benzo[1,3]dioxol-5-yl-5-(6-methyl-pyridin-2-yl)-1H-imidazol-2-yl]-piperidin-1-yl}-(4-fluoro-phenyl)-methanone;
N-{4-[4-benzo[1,3]dioxol-5-yl-5-(6-methyl-pyridin-2-yl)-1H-imidazol-2-yl]-cyclohexylmethyl}-C-pyridin-4-yl-methanesulfonamide;
N-{4-[4-benzo[1,3]dioxol-5-yl-5-(6-methyl-pyridin-2-yl)-1H-imidazol-2-yl]-bicyclo[2.2.2]oct-1-yl}-2,2,2-trifluoro-acetamide;
4-(4-benzo[1,3]dioxol-5-yl-5-pyridin-2-yl-1H-imidazol-2-yl)-piperidine-1-carboxylic acid benzyl ester;
2-(5-benzo[1,3]dioxol-5-yl-2-piperidin-4-yl-3H-imidazol-4-yl)-pyridine;
4-(4-benzo[1,3]dioxol-5-yl-5-pyridin-2-yl-1H-imidazol-2-yl)-piperidine-1-carboxylic acid 2-chloro-benzyl ester;
4-(4-benzo[1,3]dioxol-5-yl-5-pyridin-2-yl-1H-imidazol-2-yl)-piperidine-1-carboxylic acid 4,5-dimethoxy-2-nitro-benzyl ester;
4-(4-benzo[1,3]dioxol-5-yl-5-pyridin-2-yl-1H-imidazol-2-yl)-piperidine-1-carboxylic acid 3-fluoro-benzylamide;
4-(4-benzo[1,3]dioxol-5-yl-5-pyridin-2-yl-1H-imidazol-2-yl)-piperidine-1-carboxylic acid 4-fluoro-benzylamide;
4-(4-benzo[1,3]dioxol-5-yl-5-pyridin-2-yl-1H-imidazol-2-yl)-piperidine-1-carboxylic acid benzylamide;
4-(4-benzo[1,3]dioxol-5-yl-5-pyridin-2-yl-1H-imidazol-2-yl)-piperidine-1-carboxylic acid 4-methyl-benzylamide;
4-(4-benzo[1,3]dioxol-5-yl-5-pyridin-2-yl-1H-imidazol-2-yl)-piperidine-1-carboxylic acid 4-methoxy-benzylamide;
4-(4-benzo[1,3]dioxol-5-yl-5-pyridin-2-yl-1H-imidazol-2-yl)-piperidine-1-carboxylic acid 2,4-dichloro-benzylamide;
4-(4-benzo[1,3]dioxol-5-yl-5-pyridin-2-yl-1H-imidazol-2-yl)-piperidine-1-carboxylic acid 2-chloro-benzylamide;
4-(4-benzo[1,3]dioxol-5-yl-5-pyridin-2-yl-1H-imidazol-2-yl)-piperidine-1-carboxylic acid amide;
4-[4-(4-benzo[1,3]dioxol-5-yl-5-pyridin-2-yl-1H-imidazol-2-yl)-piperidine-1-sulfonyl]-benzonitrile;
2-{5-benzo[1,3]dioxol-5-yl-2-[1-(3,4-dichloro-benzenesulfonyl)-piperidin-4-yl]-3H-imidazol-4-yl}-pyridine;
{5-[4-(4-benzo[1,3]dioxol-5-yl-5-pyridin-2-yl-1H-imidazol-2-yl)-piperidine-1-sulfonyl]-naphthalen-1-yl}-dimethyl-amine;
2-[5-benzo[1,3]dioxol-5-yl-2-(1-methanesulfonyl-piperidin-4-yl)-3H-imidazol-4-yl]-pyridine;
2-[5-benzo[1,3]dioxol-5-yl-2-(1-pyridin-4-ylmethyl-piperidin-4-yl)-3H-imidazol-4-yl]-pyridine;
2-{5-benzo[1,3]dioxol-5-yl-2-[1-(propane-2-sulfonyl)-piperidin-4-yl]-3H-imidazol-4-yl}-pyridine;
2-{5-benzo[1,3]dioxol-5-yl-2-[1-(4-methoxy-benzenesulfonyl)-piperidin-4-yl]-3H-imidazol-4-yl}-pyridine;
1-{4-[4-(4-benzo[1,3]dioxol-5-yl-5-pyridin-2-yl-1H-imidazol-2-yl)-piperidine-1-sulfonyl]-phenyl}-ethanone;

2-[5-benzo[1,3]dioxol-5-yl-2-(1-furan-2-ylmethyl-piperidin-4-yl)-3H-imidazol-4-yl]-pyridine;
2-{5-benzo[1,3]dioxol-5-yl-2-[1-(4-methyl-benzyl)-piperidin-4-yl]-3H-imidazol-4-yl}-pyridine;
2-{5-benzo[1,3]dioxol-5-yl-2-[1-(3-fluoro-5-trifluoromethyl-benzyl)-piperidin-4-yl]-3H-imidazol-4-yl}-pyridine;
2-[5-benzo[1,3]dioxol-5-yl-2-(1-cyclohexylmethyl-piperidin-4-yl)-3H-imidazol-4-yl]-pyridine;
2-[4-(4-benzo[1,3]dioxol-5-yl-5-pyridin-2-yl-1H-imidazol-2-yl)-piperidin-1-ylmethyl]-cyclopropanecarboxylic acid ethyl ester;
2-[4-(4-benzo[1,3]dioxol-5-yl-5-pyridin-2-yl-1H-imidazol-2-yl)-piperidin-1-ylmethyl]-pyrrolidine-1-carboxylic acid tert-butyl ester;
2-{5-benzo[1,3]dioxol-5-yl-2-[1-(2,2-dimethyl-[1,3]dioxolan-4-ylmethyl)-piperidin-4-yl]-3H-imidazol-4-yl}-pyridine;
1-[4-(4-benzo[1,3]dioxol-5-yl-5-pyridin-2-yl-1H-imidazol-2-yl)-piperidin-1-yl]-2-methyl-propan-2-ol;
2-(6-amino-3-imino-3H-xanthen-9-yl)-4-[4-(4-benzo[1,3]dioxol-5-yl-5-pyridin-2-yl-1H-imidazol-2-yl)-piperidine-1-carbonyl]-benzoic acid;
1-[4-(4-benzo[1,3]dioxol-5-yl-5-pyridin-2-yl-1H-imidazol-2-yl)-piperidin-1-yl]-ethanone;
2-[5-benzo[1,3]dioxol-5-yl-2-(1-ethanesulfonyl-piperidin-4-yl)-3H-imidazol-4-yl ]-pyridine;
2-{5-benzo[1,3]dioxol-5-yl-2-[1-(2-phenyl-ethenesulfonyl)-piperidin-4-yl]-3H-imidazol-4-yl}-pyridine;
1-[4-(4-benzo[1,3]dioxol-5-yl-5-pyridin-2-yl-1H-imidazol-2-yl)-piperidine-1-sulfonylmethyl]-7,7-dimethyl-bicyclo[2.2.1]heptan-2-one;
2-[5-benzo[1,3]dioxol-5-yl-2-(1-p-tolylmethanesulfonyl-piperidin-4-yl)-3H-imidazol-4-yl]-pyridine;
3-(4-benzo[1,3]dioxol-5-yl-1-hydroxy-5-pyridin-2-yl-1H-imidazol-2-yl)-piperidine-1-carboxylic acid benzyl ester;
2-{5-benzo[1,3]dioxol-5-yl-2-[1-(4-methoxy-benzenesulfonyl)-piperidin-4-yl]-3H-imidazol-4-yl}-pyridine;
2-{5-benzo[1,3]dioxol-5-yl-2-[1-(2-naphthalen-1-yl-ethanesulfonyl)-piperidin-4-yl]-3H-imidazol-4-yl}-pyridine;
2-[5-benzo[1,3]dioxol-5-yl-2-(1-phenylmethanesulfonyl-piperidin-3-yl)-3H-imidazol-4-yl]-pyridine;
3-[4-benzo[1,3]dioxol-5-yl-1-hydroxy-5-(6-methyl-pyridin-2-yl)-1H-imidazol-2-yl]-piperidine-1-carboxylic acid benzyl ester;
3-[4-benzo[1,3]dioxol-5-yl-5-(6-methyl-pyridin-2-yl)-1H-imidazol-2-yl]-pyrrolidine-1-carboxylic acid benzyl ester;
4-(4-benzo[1,3]dioxol-5-yl-5-pyridin-2-yl-1H-imidazol-2-yl)-piperidine-1-carboxylic acid benzyl ester;
2-{5-benzo[1,3]dioxol-5-yl-2-[1-(3,5-bis-trifluoromethyl-phenylmethanesulfonyl)-piperidin-4-yl]-3H-imidazol-4-yl}-pyridine;
2-{5-benzo[1,3]dioxol-5-yl-2-[1-(biphenyl-4-sulfonyl)-piperidin-4-yl]-5H-imidazol-4-yl}-pyridine;
2-{5-benzo[1,3]dioxol-5-yl-2-[1-(4-phenoxy-benzenesulfonyl)-piperidin-4-yl]-3H-imidazol-4-yl}-pyridine;
2-{5-benzo[1,3]dioxol-5-yl-2-[1-(biphenyl-4-ylmethanesulfonyl)-piperidin-4-yl]-5H-imidazol-4-yl}-pyridine;
4-[5-benzo[1,3]dioxol-5-yl-1-methyl-4-(6-methyl-pyridin-2-yl)-1H-imidazol-2-yl]-piperidine-1-carboxylic acid benzyl ester;
4-[4-benzo[1,3]dioxol-5-yl-1-methyl-5-(6-methyl-pyridin-2-yl)-1H-imidazol-2-yl]-piperidine-1-carboxylic acid benzyl ester;
{4-[4-benzo[1,3]dioxol-5-yl-1-hydroxy-5-(6-methyl-pyridin-2-yl)-1H-imidazol-2-yl]-cyclohexyl}-carbamic acid benzyl ester;
4-[4-(2-chloro-pyridin-4-yl)-5-(6-methyl-pyridin-2-yl)-1H-imidazol-2-yl]-piperidine-1-carboxylic acid benzyl ester;
2-{5-benzo[1,3]dioxol-5-yl-2-[1-(3-phenoxy-phenylmethanesulfonyl)-piperidin-4-yl]-3H-imidazol-4-yl}-6-methyl-pyridine;
4-[4-(2-fluoro-pyridin-4-yl)-5-(6-methyl-pyridin-2-yl)-1H-imidazol-2-yl]-piperidine-1-carboxylic acid benzyl ester;
4-[5-benzo[1,3]dioxol-5-yl-1-hydroxy-4-(6-methyl-pyridin-2-yl)-1H-imidazol-2-yl]-piperidine-1-carboxylic acid benzyl ester;
4-[4-benzo[1,3]dioxol-5-yl-5-(6-bromo-pyridin-2-yl)-1H-imidazol-2-yl]-piperidine-1-carboxylic acid benzyl ester;
4-[4-benzo[1,3]dioxol-5-yl-5-(6-trifluoromethyl-pyridin-2-yl)-1H-imidazol-2-yl]-piperidine-1-carboxylic acid benzyl ester;
4-[5-benzo[1,3]dioxol-5-yl-4-(6-bromo-pyridin-2-yl)-1-hydroxy-1H-imidazol-2-yl ]-piperidine-1-carboxylic acid benzyl ester;
4-[4-benzo[1,3]dioxol-5-yl-5-(6-methyl-pyridin-2-yl)-1H-imidazol-2-yl]-bicyclo[2.2.2]oct-1-ylamine;
2-{5-benzo[1,3]dioxol-5-yl-2-[1-(biphenyl-4-sulfonyl)-piperidin-4-yl]-3H-imidazol-4-yl}-6-methyl-pyridine;
2-{5-benzo[1,3]dioxol-5-yl-2-[1-(4-phenoxy-benzenesulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid benzylamide;
4-[4-benzo[1,3]dioxol-5-yl-5-(6-methyl-pyridin-2-yl)-1H-imidazol-2-yl]-bicyclo[2.2.2]octane-1-carboxylic acid 3-chloro-4-fluoro-benzylamide;
2-{5-benzo[1,3]dioxol-5-yl-2-[1-(4-chloro-benzenesulfonyl)-pyrrolidin-3-yl]-3H-imidazol-4-yl}-6-methyl-pyridine;
2-{5-benzo[1,3]dioxol-5-yl-2-[1-(2-naphthalen-2-yl-ethanesulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid cyclohexylamide;
4-[4-benzo[1,3]dioxol-5-yl-5-(6-methyl-pyridin-2-yl)-1H-imidazol-2-yl]-bicyclo[2.2.2]octane-1-carboxylic acid dipropylamide;
4-[4-benzo[1,3]dioxol-5-yl-5-(6-methyl-pyridin-2-yl)-1H-imidazol-2-yl]-bicyclo[2.2.2]octane-1-carboxylic acid (2-hydroxy-1-methyl-2-phenyl-ethyl)-amide;
4-[4-benzo[1,3]dioxol-5-yl-5-(6-methyl-pyridin-2-yl)-1H-imidazol-2-yl]-bicyclo[2.2.2]octane-1-carboxylic acid (1H-benzoimidazol-2-yl)-amide;
4-[4-benzo[1,3]dioxol-5-yl-5-(6-methyl-pyridin-2-yl)-1H-imidazol-2-yl]-bicyclo[2.2.2]octane-1-carboxylic acid (pyridin-4-ylmethyl)-amide;
4-[4-benzo[1,3]dioxol-5-yl-5-(6-methyl-pyridin-2-yl)-1H-imidazol-2-yl]-bicyclo[2.2.2]octane-1-carboxylic acid benzothiazol-2-ylamide;
4-[4-benzo[1,3]dioxol-5-yl-5-(6-methyl-pyridin-2-yl)-1H-imidazol-2-yl]-bicyclo[2.2.2]octane-1-carboxylic acid (5,7-difluoro-benzothiazol-2-yl)-amide;
{4-[4-benzo[1,3]dioxol-5-yl-5-(6-methyl-pyridin-2-yl)-1H-imidazol-2-yl]-piperidin-1-yl}-(4-methoxy-phenyl)-methanone; and {4-[4-benzo[1,3]dioxol-5-yl-1-hydroxy-5-(6-methyl-pyridin-2-yl)-1H-imidazol-2-yl]-cyclohexylmethyl}-carbamic acid benzyl ester.

18. The compound of claim 1, said compound being selected from the group consisting of:
- 4-[4-(4-benzo[1,3]dioxol-5-yl-5-pyridin-2-yl-1H-imidazol-2-yl)-piperidine-1-sulfonyl]-benzoic acid;
- 2-[5-benzo[1,3]dioxol-5-yl-2-(1-phenylmethanesulfonyl-piperidin-4-yl)-3H-imidazol-4-yl]-pyridine;
- 2-{5-benzo[1,3]dioxol-5-yl-2-[1-(butane-1-sulfonyl)-piperidin-4-yl]-3H-imidazol-4-yl}-pyridine;
- 2-{5-benzo[1,3]dioxol-5-yl-2-[1-(3,5-dichloro-phenylmethanesulfonyl)-piperidin-4-yl]-3H-imidazol-4-yl}-pyridine;
- 2-{5-benzo[1,3]dioxol-5-yl-2-[1-(4-fluoro-phenylmethanesulfonyl)-piperidin-4-yl]-3H-imidazol-4-yl}-pyridine;
- 2-{5-benzo[1,3]dioxol-5-yl-2-[1-(2-phenyl-ethanesulfonyl)-piperidin-4-yl]-3H-imidazol-4-yl}-pyridine;
- 2-{5-benzo[1,3]dioxol-5-yl-2-[1-(pyridin-2-yl-methanesulfonyl)-piperidin-4-yl]-3H-imidazol-4-yl}-pyridine;
- 2-[5-benzo[1,3]dioxol-5-yl-2-(1-phenylmethanesulfonyl-piperidin-4-yl)-3H-imidazol-4-yl]-6-methyl-pyridine;
- 2-{5-benzo[1,3]dioxol-5-yl-2-[1-(3,5-difluoro-phenylmethanesulfonyl)-piperidin-4-yl]-3H-imidazol-4-yl}-pyridine;
- 2-{5-benzo[1,3]dioxol-5-yl-2-[1-(pyridin-2-ylmethanesulfonyl)-piperidin-4-yl]-3H-imidazol-4-yl}-6-methyl-pyridine;
- 2-[5-benzo[1,3]dioxol-5-yl-2-(1-methanesulfonyl-piperidin-4-yl)-3H-imidazol-4-yl]-6-methyl-pyridine;
- 2-[5-benzo[1,3]dioxol-5-yl-2-(1-ethanesulfonyl-piperidin-4-yl)-3H-imidazol-4-yl]-6-methyl-pyridine;
- 2-{5-benzo[1,3]dioxol-5-yl-2-[1-(propane-1-sulfonyl)-piperidin-4-yl]-3H-imidazol-4-yl}-6-methyl-pyridine;
- 2-{5-benzo[1,3]dioxol-5-yl-2-[1-(butane-1-sulfonyl)-piperidin-4-yl]-3H-imidazol-4-yl}-6-methyl-pyridine;
- 2-{5-benzo[1,3]dioxol-5-yl-2-[1-(pyridin-3-ylmethanesulfonyl)-piperidin-4-yl]-3H-imidazol-4-yl}-6-methyl-pyridine;
- 2-{5-benzo[1,3]dioxol-5-yl-2-[1-(pyridin-4-ylmethanesulfonyl)-piperidin-4-yl]-3H-imidazol-4-yl}-6-methyl-pyridine;
- 2-{5-benzo[1,3]dioxol-5-yl-2-[1-(3,5-difluoro-phenylmethanesulfonyl)-piperidin-4-yl]-3H-imidazol-4-yl}-6-methyl-pyridine;
- 2-{5-benzo[1,3]dioxol-5-yl-2-[l1-(thiophene-2-sulfonyl)-piperidin-4-yl]-3H-imidazol-4-yl}-6-methyl-pyridine;
- 2-{5-benzo[1,3]dioxol-5-yl-2-[1-(1-methyl-1H-imidazole-4-sulfonyl)-piperidin-4-yl]-3H-imidazol-4-yl}-6-methyl-pyridine;
- 2-{5-benzo[1,3]dioxol-5-yl-2-[1-(5-methyl-isoxazole-4-sulfonyl)-piperidin-4-yl]-3H-imidazol-4-yl}-6-methyl-pyridine;
- N-{4-[4-benzo[1,3]dioxol-5-yl-5-(6-methyl-pyridin-2-yl)-1H-imidazol-2-yl]-cyclohexyl}-C-phenyl-methanesulfonamide;
- butane-1-sulfonic acid {4-[4-benzo[1,3]dioxol-5-yl-5-(6-methyl-pyridin-2-yl)-1H-imidazol-2-yl]-cyclohexyl}-amide;
- N-{4-[4-benzo[1,3]dioxol-5-yl-5-(6-methyl-pyridin-2-yl)-1H-imidazol-2-yl]-cyclohexyl}-C-pyridin-2-yl-methanesulfonamide;
- thiophene-2-sulfonic acid {4-[4-benzo[1,3]dioxol-5-yl-5-(6-methyl-pyridin-2-yl)-1H-imidazol-2-yl]-cyclohexyl}-amide;
- 1-methyl-1H-imidazole-4-sulfonic acid {4-[4-benzo[1,3]dioxol-5-yl-5-(6-methyl-pyridin-2-yl)-1H-imidazol-2-yl]-cyclohexyl}-amide;
- 4-[4-benzo[1,3]dioxol-5-yl-5-(6-methyl-pyridin-2-yl)-1H-imidazol-2-yl]-bicyclo[2.2.2]octane-1-carboxylic acid;
- 2-{5-benzo[1,3]dioxol-5-yl-2-[1-(thiophene-3-sulfonyl)-piperidin-4-yl]-3H-imidazol-4-yl}-6-methyl-pyridine;
- 4-[4-benzo[1,3]dioxol-5-yl-5-(6-ethyl-pyridin-2-yl)-1H-imidazol-2-yl]-piperidine-1-carboxylic acid benzyl ester;
- {4-[4-benzo[1,3]dioxol-5-yl-5-(6-methyl-pyridin-2-yl)-1H-imidazol-2-yl]-bicyclo[2.2.2]oct-1-yl}-methanol;
- 4-[4-benzo[1,3]dioxol-5-yl-5-(6-methyl-pyridin-2-yl)-1H-imidazol-2-yl]-bicyclo[2.2.2]octane-1-carboxylic acid amide;
- 2-{5-benzo[1,3]dioxol-5-yl-2-[1-(propane-2-sulfonyl)-piperidin-4-yl]-3H-imidazol-4-yl}-6-methyl-pyridine;
- 4-[4-benzo[1,3]dioxol-5-yl-5-(6-methyl-pyridin-2-yl)-1H-imidazol-2-yl]-bicyclo[2.2.2]octane-1-carbonitrile;
- 2-[5-benzo[1,3]dioxol-5-yl-2-(1-phenylmethanesulfonyl-piperidin-4-yl)-3H-imidazol-4-yl]-6-ethyl-pyridine;
- N-{4-[4-benzo[1,3]dioxol-5-yl-5-(6-methyl-pyridin-2-yl)-1H-imidazol-2-yl]-bicyclo[2.2.2]oct-1-yl}-methanesulfonamide;
- N-{4-[4-benzo[1,3]dioxol-5-yl-5-(6-methyl-pyridin-2-yl)-1H-imidazol-2-yl]-bicyclo[2.2.2]oct-1-yl}-C-pyridin-2-yl-methanesulfonamide;
- 2-{5-benzo[1,3]dioxol-5-yl-2-[4-(1H-tetrazol-5-yl)-bicyclo[2.2.2]oct-1-yl]-3H-imidazol-4-yl}-6-methyl-pyridine;
- N-{4-[4-benzo[1,3]dioxol-5-yl-5-(6-methyl-pyridin-2-yl)-1H-imidazol-2-yl]-bicyclo[2.2.2]oct-1-yl}-acetamide;
- thiophene-2-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
- 1-methyl-1H-imidazole-4-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
- thiophene-3-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
- 2-{5-benzo[1,3]dioxol-5-yl-2-[1-(2-phenyl-ethanesulfonyl)-piperidin-4-yl]-3H-imidazol-4-yl}-6-methyl-pyridine;
- methanesulfonic acid 4-[4-benzo[1,3]dioxol-5-yl-5-(6-methyl-pyridin-2-yl)-1H-imidazol-2-yl]-bicyclo[2.2.2]oct-1-ylmethyl ester;
- {4-[4-benzo[1,3]dioxol-5-yl-5-(6-methyl-pyridin-2-yl)-1H-imidazol-2-yl]-bicyclo[2.2.2]oct-1-yl}-acetonitrile;
- {4-[4-benzo[1,3]dioxol-5-yl-5-(6-methyl-pyridin-2-yl)-1H-imidazol-2-yl]-bicyclo[2.2.2]oct-1-yl}-acetic acid;
- N-{4-[4-benzo[1,3]dioxol-5-yl-5-(6-methyl-pyridin-2-yl)-1H-imidazol-2-yl]-bicyclo[2.2.2]oct-1-ylmethyl}-methanesulfonamide;
- N-{4-[4-benzo[1,3]dioxol-5-yl-5-(6-methyl-pyridin-2-yl)-1H-imidazol-2-yl]-bicyclo[2.2.2]oct-1-ylmethyl}-C-pyridin-2-yl-methanesulfonamide;
- 2-{5-benzo[1,3]dioxol-5-yl-2-[1-(2-nitro-phenylmethanesulfonyl)-piperidin-4-yl ]-3H-imidazol-4-yl}-6-methyl-pyridine;
- 1-{4-[4-benzo[1,3]dioxol-5-yl-5-(6-methyl-pyridin-2-yl)-1H-imidazol-2-yl ]-piperidine-1-sulfonylmethyl}-7,7-dimethyl-bicyclo[2.2.1]heptan-2-one;

2-{5-benzo[1,3]dioxol-5-yl-2-[1-(4-chloro-benzenesulfonyl)-piperidin-4-yl]-3H-imidazol-4-yl}-6-methyl-pyridine;

4-[4-benzo[1,3]dioxol-5-yl-5-(6-methyl-pyridin-2-yl)-1H-imidazol-2-yl]-bicyclo[2.2.2]octane-1-carboxylic acid methylamide;

2-{4-[4-benzo[1,3]dioxol-5-yl-5-(6-methyl-pyridin-2-yl)-1H-imidazol-2-yl ]-piperidine-1-sulfonylmethyl}-phenylamine;

4-[4-benzo[1,3]dioxol-5-yl-5-(6-methyl-pyridin-2-yl)-1H-imidazol-2-yl]-bicyclo[2.2.2]octane-1-carboxylic acid (1-methyl-5-methylsulfanyl-1H-[1,2,4]triazol-3-yl)-amide;

4-[4-benzo[1,3]dioxol-5-yl-5-(6-methyl-pyridin-2-yl)-1H-imidazol-2-yl]-bicyclo[2.2.2]octane-1-carboxylic acid dimethylamide;

{4-[4-benzo[1,3]dioxol-5-yl-5-(6-methyl-pyridin-2-yl)-1H-imidazol-2-yl]-piperidin-1-yl}-(3-chloro-phenyl)-methanone;

4-[5-benzo[1,3]dioxol-5-yl-4-(6-cyclopropyl-pyridin-2-yl)-1H-imidazol-2-yl]-bicyclo[2.2.2]octane-1-carboxylic acid;

4-[5-benzo[1,3]dioxol-5-yl-4-(6-methyl-pyridin-2-yl)-1H-imidazol-2-yl]-bicyclo[2.2.2]octane-1-carboxylic acid methoxy-amide;

4-[5-benzo[1,3]dioxol-5-yl-4-(6-methyl-pyridin-2-yl)-1H-imidazol-2-yl]-bicyclo[2.2.2]octane-1-carboxylic acid hydroxyamide;

{4-[4-benzo[1,3]dioxol-5-yl-5-(6-methyl-pyridin-2-yl)-1H-imidazol-2-yl]-cyclohexylmethyl}-carbamic acid benzyl ester;

4-[4-benzo[1,3]dioxol-5-yl-5-(6-methyl-pyridin-2-yl)-1H-imidazol-2-yl]-bicyclo[2.2.2]octane-1-carboxylic acid hydrazide;

N-{4-[4-benzo[1,3]dioxol-5-yl-5-(6-methyl-pyridin-2-yl)-1H-imidazol-2-yl]-cyclohexylmethyl}-acetamide;

N-{4-[4-benzo[1,3]dioxol-5-yl-5-(6-methyl-pyridin-2-yl)-1H-imidazol-2-yl]-cyclohexylmethyl}-methanesulfonamide;

N-{4-[4-benzo[1,3]dioxol-5-yl-5-(6-methyl-pyridin-2-yl)-1H-imidazol-2-yl]-cyclohexylmethyl}-C-phenyl-methanesulfonamide;

butane-1-sulfonic acid {4-[4-benzo[1,3]dioxol-5-yl-5-(6-methyl-pyridin-2-yl)-1H-imidazol-2-yl]-cyclohexylmethyl}-amide;

propane-2-sulfonic acid {4-[4-benzo[1,3]dioxol-5-yl-5-(6-methyl-pyridin-2-yl)-1H-imidazol-2-yl]-cyclohexylmethyl}-amide;

N-{4-[4-benzo[1,3]dioxol-5-yl-5-(6-methyl-pyridin-2-yl)-1H-imidazol-2-yl]-cyclohexylmethyl}-C-pyridin-2-yl-methanesulfonamide;

N-{4-[4-benzo[1,3]dioxol-5-yl-5-(6-methyl-pyridin-2-yl)-1H-imidazol-2-yl]-cyclohexyl}-methanesulfonamide;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid methyl ester;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid methyl ester;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid;

4-[4-benzo[1,3]dioxol-5-yl-5-(6-methyl-pyridin-2-yl)-1H-imidazol-2-yl]-bicyclo[2.2.2]octan-1-ol;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

N-{4-[4-benzo[1,3]dioxol-5-yl-5-(6-methyl-pyridin-2-yl)-1H-imidazol-2-yl]-bicyclo[2.2.2]oct-1-yl}-sulfamide;

sulfamic acid 4-[4-benzo[1,3]dioxol-5-yl-5-(6-methyl-pyridin-2-yl)-1H-imidazol-2-yl]-bicyclo[2.2.2]oct-1-yl ester;

{4-[4-(6-methyl-pyridin-2-yl)-5-quinoxalin-6-yl-1H-imidazol-2-yl]-cyclohexyl}-carbamic acid benzyl ester;

N-{4-[4-benzo[1,3]dioxol-5-yl-5-(6-methyl-pyridin-2-yl)-1H-imidazol-2-yl]-bicyclo[2.2.2]octane-1-carbonyl}-methanesulfonamide;

N-{4-[4-benzo[1,3]dioxol-5-yl-5-(6-methyl-pyridin-2-yl)-1H-imidazol-2-yl]-bicyclo[2.2.2]octane-1-carbonyl}-benzenesulfonamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid methyl ester;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid;

N-{4-[4-(6-methyl-pyridin-2-yl)-5-quinoxalin-6-yl-1H-imidazol-2-yl]-cyclohexyl}-acetamide;

4-[4-(6-methyl-pyridin-2-yl)-5-quinoxalin-6-yl-1H-imidazol-2-yl]-bicyclo[2.2.2]octane-1-carboxylic acid methyl ester;

4-[4-(6-methyl-pyridin-2-yl)-5-quinoxalin-6-yl-1H-imidazol-2-yl]-bicyclo[2.2.2]octane-1-carboxylic acid;

4-[4-(6-methyl-pyridin-2-yl)-5-quinoxalin-6-yl-1H-imidazol-2-yl]-bicyclo[2.2.2]octane-1-carboxylic acid hydroxyamide;

4-[4-(6-methyl-pyridin-2-yl)-5-quinoxalin-6-yl-1H-imidazol-2-yl]-bicyclo[2.2.2]octane-1-carboxylic acid amide;

N-{4-[4-(6-methyl-pyridin-2-yl)-5-quinoxalin-6-yl-1H-imidazol-2-yl]-cyclohexyl}-methanesulfonamide;

2,2,2-trifluoro-N-{4-[4-(6-methyl-pyridin-2-yl)-5-quinoxalin-6-yl-1H-imidazol-2-yl]-cyclohexyl}-acetamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid amide;

N-{4-[5-(6-methyl-pyridin-2-yl)-4-quinoxalin-6-yl-1H-imidazol-2-yl]-bicyclo[2.2.2]oct-1-yl}-methanesulfonamide;

N-{4-[5-(6-methyl-pyridin-2-yl)-4-quinoxalin-6-yl-1H-imidazol-2-yl]-bicyclo[2.2.2]oct-1-yl}-acetamide;

4-[4-(5-fluoro-6-methyl-pyridin-2-yl)-5-[1,2,4]triazolo[1,5-a]pyridin-6-yl-1H-imidazol-2-yl]-bicyclo[2.2.2]octane-1-carboxylic acid methyl ester;

4-(4-benzo[1,3]dioxol-5-yl-5-pyridin-2-yl-1H-imidazol-2-yl)-piperidine-1-carboxylic acid 4-nitro-benzyl ester;

2-{5-benzo[1,3]dioxol-5-yl-2-[1-(toluene-4-sulfonyl)-piperidin-4-yl]-3H-imidazol-4-yl}-pyridine;

2-{5-benzo[1,3]dioxol-5-yl-2-[1-(4-chloro-benzenesulfonyl)-piperidin-4-yl]-3H-imidazol-4-yl}-pyridine;
2-{5-benzo[1,3]dioxol-5-yl-2-[1-(2-nitro-phenylmethanesulfonyl)-piperidin-4-yl]-3H-imidazol-4-yl}-pyridine;
2-{5-benzo[1,3]dioxol-5-yl-2-[1-(propane-1-sulfonyl)-piperidin-4-yl]-3H-imidazol-4-yl}-pyridine;
2-{5-benzo[1,3]dioxol-5-yl-2-[1-(4-chloro-phenylmethanesulfonyl)-piperidin-4-yl]-3H-imidazol-4-yl}-pyridine;
2-{5-benzo[1,3]dioxol-5-yl-2-[1-(3,4-dichloro-phenylmethanesulfonyl)-piperidin-4-yl]-3H-imidazol-4-yl}-pyridine;
3-(4-benzo[1,3]dioxol-5-yl-5-pyridin-2-yl-1H-imidazol-2-yl)-piperidine-1-carboxylic acid benzyl ester;
4-[4-benzo[1,3]dioxol-5-yl-5-(6-methyl-pyridin-2-yl)-1H-imidazol-2-yl]-piperidine-1-carboxylic acid benzyl ester;
3-[4-benzo[1,3]dioxol-5-yl-5-(6-methyl-pyridin-2-yl)-1H-imidazol-2-yl]-piperidine-1-carboxylic acid benzyl ester;
2-{5-benzo[1,3]dioxol-5-yl-2-[1-(pyridin-4-ylmethanesulfonyl)-piperidin-4-yl]-3H-imidazol-4-yl-pyridine;
2-{5-benzo[1,3]dioxol-5-yl-2-[1-(pyridin-3-ylmethanesulfonyl)-piperidin-4-yl]-3H-imidazol-4-yl-pyridine;
2-{5-benzo[1,3]dioxol-5-yl-2-[1-(3-trifluoromethyl-phenylmethanesulfonyl)-piperidin-4-yl]-3H-imidazol-4-yl}-pyridine;
3-[4-benzo[1,3]dioxol-5-yl-1-hydroxy-5-(6-methyl-pyridin-2-yl)-1H-imidazol-2-yl]-pyrrolidine-1-carboxylic acid benzyl ester;
{4-[4-benzo[1,3]dioxol-5-yl-5-(6-methyl-pyridin-2-yl)-1H-imidazol-2-yl]-cyclohexyl}-carbamic acid benzyl ester;
2-{5-benzo[1,3]dioxol-5-yl-2-[1-(3-trifluoromethyl-phenylmethanesulfonyl)-piperidin-4-yl]-3H-imidazol-4-yl}-6-methyl-pyridine;
2-{5-benzo[1,3]dioxol-5-yl-2-[1-(butane-1-sulfonyl)-piperidin-3-yl]-3H-imidazol-4-yl}-6-methyl-pyridine;
2-[5-benzo[1,3]dioxol-5-yl-2-(1-phenylmethanesulfonyl-piperidin-3-yl)-3H-imidazol-4-yl]-6-methyl-pyridine;
{4-[2-[1-(butane-1-sulfonyl)-piperidin-4-yl]-5-(6-methyl-pyridin-2-yl)-1H-imidazol-4-yl]-pyridin-2-yl}-(4-methoxy-benzyl)-amine;
4-[2-[1-(butane-1-sulfonyl)-piperidin-4-yl]-5-(6-methyl-pyridin-2-yl)-1H-imidazol-4-yl]-pyridin-2-ylamine;
4-[4-benzo[1,3]dioxol-5-yl-5-(6-methyl-pyridin-2-yl)-1H-imidazol-2-yl]-bicyclo[2.2.2]octane-1-carboxylic acid methyl ester;
2-{5-benzo[1,3]dioxol-5-yl-2-[1-(5-methyl-2-trifluoromethyl-furan-3-sulfonyl)-piperidin-4-yl]-3H-imidazol-4-yl}-6-methyl-pyridine;
4-[2-(1-phenylmethanesulfonyl-piperidin-4-yl)-5-(6-methyl-pyridin-2-yl)-1H-imidazol-4-yl]-pyridin-2-ylfluoride;
(4-methoxy-benzyl)-{4-[5-(6-methyl-pyridin-2-yl)-2-(1-phenylmethanesulfonyl-piperidin-4-yl)-1H-imidazol-4-yl]-pyridin-2-yl}-amine;
{4-[4-benzo[1,3]dioxol-5-yl-5-(6-methyl-pyridin-2-yl)-1H-imidazol-2-yl]-bicyclo[2.2.2]oct-1-yl}-carbamic acid benzyl ester;
2-[5-benzo[1,3]dioxol-5-yl-2-(1-phenylmethanesulfonyl-piperidin-4-yl)-3H-imidazol-4-yl]-6-bromo-pyridine;
1-{4-[4-benzo[1,3]dioxol-5-yl-5-(6-methyl-pyridin-2-yl)-1H-imidazol-2-yl]-piperidin-1-yl}-3-phenyl-propan-1-one;
N-{4-[4-benzo[1,3]dioxol-5-yl-5-(6-methyl-pyridin-2-yl)-1H-imidazol-2-yl]-bicyclo[2.2.2]oct-1-yl}-C-phenyl-methanesulfonamide;
2-{5-benzo[1,3]dioxol-5-yl-2-[1-(2-phenyl-ethenesulfonyl)-piperidin-4-yl]-3H-imidazol-4-yl}-6-methyl-pyridine;
2-{5-benzo[1,3]dioxol-5-yl-2-[1-(3,4-dichloro-benzenesulfonyl)-piperidin-4-yl]-3H-imidazol-4-yl}-6-methyl-pyridine;
N-{4-[4-benzo[1,3]dioxol-5-yl-5-(6-methyl-pyridin-2-yl)-1H-imidazol-2-yl]-bicyclo[2.2.2]oct-1 -ylmethyl}-C-phenyl-methanesulfonamide;
4-[4-benzo[1,3]dioxol-5-yl-5-(6-methyl-pyridin-2-yl)-1H-imidazol-2-yl]-bicyclo[2.2.2]octane-1-carboxylic acid (pyridin-2-ylmethyl)-amide;
4-[4-benzo[1,3]dioxol-5-yl-5-(6-methyl-pyridin-2-yl)-1H-imidazol-2-yl]-bicyclo[2.2.2]octane-1-carboxylic acid (furan-2-ylmethyl)-amide;
2-[5-benzo[1,3]dioxol-5-yl-2-(1-methanesulfonyl-pyrrolidin-3-yl)-3H-imidazol-4-yl]-6-methyl-pyridine;
2-{5-benzo[1,3]dioxol-5-yl-2-[1-(butane-1-sulfonyl)-pyrrolidin-3-yl]-3H-imidazol-4-yl}-6-methyl-pyridine;
2-{5-benzo[1,3]dioxol-5-yl-2-[1-(1-methyl-1H-imidazole-4-sulfonyl)-pyrrolidin-3-yl]-3H-imidazol-4-yl}-6-methyl-pyridine;
2-[5-benzo[1,3]dioxol-5-yl-2-(1-phenylmethanesulfonyl-pyrrolidin-3-yl)-3H-imidazol-4-yl]-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid ethylamide;
4-[4-benzo[1,3]dioxol-5-yl-5-(6-methyl-pyridin-2-yl)-1H-imidazol-2-yl]-bicyclo[2.2.2]octane-1-carboxylic acid butylamide;
4-[4-benzo[1,3]dioxol-5-yl-5-(6-methyl-pyridin-2-yl)-1H-imidazol-2-yl]-bicyclo[2.2.2]octane-1-carboxylic acid isopropylamide;
4-[4-benzo[1,3]dioxol-5-yl-5-(6-methyl-pyridin-2-yl)-1H-imidazol-2-yl]-bicyclo[2.2.2]octane-1-carboxylic acid (3-imidazol-1-yl-propyl)-amide;
{4-[4-benzo[1,3]dioxol-5-yl-5-(6-methyl-pyridin-2-yl)-1H-imidazol-2-yl]-bicyclo[2.2.2]oct-1-yl}-pyrrolidin-1-yl-methanone;
4-[4-benzo[1,3]dioxol-5-yl-5-(6-methyl-pyridin-2-yl)-1H-imidazol-2-yl]-bicyclo[2.2.2]octane-1-carboxylic acid diethylamide;
4-[4-benzo[1,3]dioxol-5-yl-5-(6-methyl-pyridin-2-yl)-1H-imidazol-2-yl]-cyclohexylamine;
{4-[4-benzo[1,3]dioxol-5-yl-5-(6-methyl-pyridin-2-yl)-1H-imidazol-2-yl]-piperidin-1-yl}-(4-fluoro-phenyl)-methanone;
N-{4-[4-benzo[1,3]dioxol-5-yl-5-(6-methyl-pyridin-2-yl)-1H-imidazol-2-yl]-cyclohexylmethyl}-C-pyridin-4-yl-methanesulfonamide; and
N-{4-[4-benzo[1,3]dioxol-5-yl-5-(6-methyl-pyridin-2-yl)-1H-imidazol-2-yl]-bicyclo[2.2.2]oct-1-yl}-2,2,2-trifluoro-acetamide.

19. The compound of claim 1, said compound being selected from the group consisting of:
4-[4-(4-benzo[1,3]dioxol-5-yl-5-pyridin-2-yl-1H-imidazol-2-yl)-piperidine-1-sulfonyl]-benzoic acid;
2-[5-benzo[1,3]dioxol-5-yl-2-(1-phenylmethanesulfonyl-piperidin-4-yl)-3H-imidazol-4-yl]-pyridine;
2-{5-benzo[1,3]dioxol-5-yl-2-[1-(butane-1-sulfonyl)-piperidin-4-yl]-3H-imidazol-4-yl}-pyridine;
2-{5-benzo[1,3]dioxol-5-yl-2-[1-(3,5-dichloro-phenylmethanesulfonyl)-piperidin-4-yl]-3H-imidazol-4-yl}-pyridine;

2-{5-benzo[1,3]dioxol-5-yl-2-[1-(4-fluoro-phenyl-methanesulfonyl)-piperidin-4-yl]-3H-imidazol-4-yl}-pyridine;
2-{5-benzo[1,3]dioxol-5-yl-2-[1-(2-phenyl-ethanesulfonyl)-piperidin-4-yl]-3H-imidazol-4-yl}-pyridine;
2-{5-benzo[1,3]dioxol-5-yl-2-[1-(pyridin-2-yl-methanesulfonyl)-piperidin-4-yl]-3H-imidazol-4-yl}-pyridine;
2-[5-benzo[1,3]dioxol-5-yl-2-(1-phenylmethanesulfonyl-piperidin-4-yl)-3H-imidazol-4-yl]-6-methyl-pyridine;
2-{5-benzo[1,3]dioxol-5-yl-2-[1-(3,5-difluoro-phenyl-methanesulfonyl)-piperidin-4-yl]-3H-imidazol-4-yl}-pyridine;
2-{5-benzo[1,3]dioxol-5-yl-2-[1-(pyridin-2-ylmethanesulfonyl)-piperidin-4-yl]-3H-imidazol-4-yl}-6-methyl-pyridine;
2-[5-benzo[1,3]dioxol-5-yl-2-(1-methanesulfonyl-piperidin-4-yl)-3H-imidazol-4-yl]-6-methyl-pyridine;
2-[5-benzo[1,3]dioxol-5-yl-2-(1-ethanesulfonyl-piperidin-4-yl)-3H-imidazol-4-yl]-6-methyl-pyridine;
2-{5-benzo[1,3]dioxol-5-yl-2-[1-(propane-1-sulfonyl)-piperidin-4-yl]-3H-imidazol-4-yl}-6-methyl-pyridine;
2-{5-benzo[1,3]dioxol-5-yl-2-[1-(butane-1-sulfonyl)-piperidin-4-yl]-3H-imidazol-4-yl}-6-methyl-pyridine;
2-{5-benzo[1,3]dioxol-5-yl-2-[1-(pyridin-3-ylmethanesulfonyl)-piperidin-4-yl]-3H-imidazol-4-yl}-6-methyl-pyridine;
2-{5-benzo[1,3]dioxol-5-yl-2-[1-(pyridin-4-ylmethanesulfonyl)-piperidin-4-yl]-3-imidazol-4-yl}-6-methyl-pyridine;
2-{5-benzo[1,3]dioxol-5-yl-2-[1-(3,5-difluoro-phenyl-methanesulfonyl)-piperidin-4-yl]-3H-imidazol-4-yl}-6-methyl-pyridine;
2-{5-benzo[1,3]dioxol-5-yl-2-[1-(thiophene-2-sulfonyl)-piperidin-4-yl]-3H-imidazol-4-yl}-6-methyl-pyridine;
2-{5-benzo[1,3]dioxol-5-yl-2-[1-(1-methyl-1H-imidazole-4-sulfonyl)-piperidin-4-yl]-3H-imidazol-4-yl}-6-methyl-pyridine;
2-{5-benzo[1,3]dioxol-5-yl-2-[1-(5-methyl-isoxazole-4-sulfonyl)-piperidin-4-yl]-3H-imidazol-4-yl}-6-methyl-pyridine;
N-{4-[4-benzo[1,3]dioxol-5-yl-5-(6-methyl-pyridin-2-yl)-1H-imidazol-2-yl]-cyclohexyl}-C-phenyl-methanesulfonamide;
butane-1-sulfonic acid {4-[4-benzo[1,3]dioxol-5-yl-5-(6-methyl-pyridin-2-yl)-1H-imidazol-2-yl]-cyclohexyl}-amide;
N-{4-[4-benzo[1,3]dioxol-5-yl-5-(6-methyl-pyridin-2-yl)-1H-imidazol-2-yl]-cyclohexyl}-C-pyridin-2-yl-methanesulfonamide;
thiophene-2-sulfonic acid {4-[4-benzo[1,3]dioxol-5-yl-5-(6-methyl-pyridin-2-yl)-1H-imidazol-2-yl]-cyclohexyl}-amide;
1-methyl-1H-imidazole-4-sulfonic acid {4-[4-benzo[1,3]dioxol-5-yl-5-(6-methyl-pyridin-2-yl)-1H-imidazol-2-yl]-cyclohexyl}-amide;
4-[4-benzo[1,3]dioxol-5-yl-5-(6-methyl-pyridin-2-yl)-1H-imidazol-2-yl]-bicyclo[2.2.2]octane-1-carboxylic acid;
2-{5-benzo[1,3]dioxol-5-yl-2-[1-(thiophene-3-sulfonyl)-piperidin-4-yl]-3H-imidazol-4-yl}-6-methyl-pyridine;
4-[4-benzo[1,3]dioxol-5-yl-5-(6-ethyl-pyridin-2-yl)-1H-imidazol-2-yl]-piperidine-1-carboxylic acid benzyl ester;
{4-[4-benzo[1,3]dioxol-5-yl-5-(6-methyl-pyridin-2-yl)-1H-imidazol-2-yl]-bicyclo[2.2.2]oct-1-yl}-methanol;
4-[4-benzo[1,3]dioxol-5-yl-5-(6-methyl-pyridin-2-yl)-1H-imidazol-2-yl]-bicyclo[2.2.2]octane-1-carboxylic acid amide;
2-{5-benzo[1,3]dioxol-5-yl-2-[1-(propane-2-sulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carbonitrile;
2-[5-benzo[1,3]dioxol-5-yl-2-(1-phenylmethanesulfonyl-piperidin-4-yl)-3H-imidazol-4-yl]-6-ethyl-pyridine;
N-{4-[4-benzo[1,3]dioxol-5-yl-5-(6-methyl-pyridin-2-yl)-1H-imidazol-2-yl]-bicyclo[2.2.2]oct-1-yl}-methanesulfonamide;
N-{4-[4-benzo[1,3]dioxol-5-yl-5-(6-methyl-pyridin-2-yl)-1H-imidazol-2-yl]-bicyclo[2.2.2]oct-1-yl}-C-pyridin-2-yl-methanesulfonamide;
2-{5-benzo[1,3]dioxol-5-yl-2-[4-(1H-tetrazol-5-yl)-bicyclo[2.2.2]oct-1-yl ]-3H-imidazol-4-yl}-6-methyl-pyridine;
N-{4-[4-benzo[1,3]dioxol-5-yl-5-(6-methyl-pyridin-2-yl)-1H-imidazol-2-yl]-bicyclo[2.2.2]oct-1-yl}-acetamide;
thiophene-2-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
1-methyl-1H-imidazole-4-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
thiophene-3-sulfonic acid {4-[4-benzo[1,3]dioxol-5-yl-5-(6-methyl-pyridin-2-yl)-1H-imidazol-2-yl]-bicyclo[2.2.2]oct-1-yl}-amide;
2-{5-benzo[1,3]dioxol-5-yl-2-[1-(2-phenyl-ethanesulfonyl)-piperidin-4-yl]-3H-imidazol-4-yl}-6-methyl-pyridine;
methanesulfonic acid 4-[4-benzo[1,3]dioxol-5-yl-5-(6-methyl-pyridin-2-yl)-1H-imidazol-2-yl]-bicyclo[2.2.2]oct-1-ylmethyl ester;
{4-[4-benzo[1,3]dioxol-5-yl-5-(6-methyl-pyridin-2-yl)-1H-imidazol-2-yl]-bicyclo[2.2.2]oct-1-yl}-acetonitrile;
{4-[4-benzo[1,3]dioxol-5-yl-5-(6-methyl-pyridin-2-yl)-1H-imidazol-2-yl]-bicyclo[2.2.2]oct-1-yl}-acetic acid;
N-{4-[4-benzo[1,3]dioxol-5-yl-5-(6-methyl-pyridin-2-yl)-1H-imidazol-2-yl]-bicyclo[2.2.2]oct-1-ylmethyl}-methanesulfonamide;
N-{4-[4-benzo[1,3]dioxol-5-yl-5-(6-methyl-pyridin-2-yl)-1H-imidazol-2-yl]-bicyclo[2.2.2]oct-1-ylmethyl}-C-pyridin-2-yl-methanesulfonamide;
2-{5-benzo[1,3]dioxol-5-yl-2-[1-(2-nitro-phenyl-methanesulfonyl)-piperidin-4-yl]-3H-imidazol-4-yl}-6-methyl-pyridine;
1-{4-[4-benzo[1,3]dioxol-5-yl-5-(6-methyl-pyridin-2-yl)-1H-imidazol-2-yl]-piperidine-1-sulfonylmethyl}-7,7-dimethyl-bicyclo[2.2.1]heptan-2-one;
2-{5-benzo[1,3]dioxol-5-yl-2-[1-(4-chloro-benzenesulfonyl)-piperidin-4-yl]-3H-imidazol-4-yl}-6-methyl-pyridine;
4-[4-benzo[1,3]dioxol-5-yl-5-(6-methyl-pyridin-2-yl)-1H-imidazol-2-yl]-bicyclo[2.2.2]octane-1-carboxylic acid methylamide;
2-{4-[4-benzo[1,3]dioxol-5-yl-5-(6-methyl-pyridin-2-yl)-1H-imidazol-2-yl]-piperidine-1-sulfonylmethyl}-phenylamine;
4-[4-benzo[1,3]dioxol-5-yl-5-(6-methyl-pyridin-2-yl)-1H-imidazol-2-yl]-bicyclo[2.2.2]octane-1-carboxylic acid (1-methyl-5-methylsulfanyl-1H-[1,2,4]triazol-3-yl)-amide;

4-[4-benzo[1,3]dioxol-5-yl-5-(6-methyl-pyridin-2-yl)-1H-imidazol-2-yl]-bicyclo[2.2.2]octane-1-carboxylic acid dimethylamide;

{4-[4-benzo[1,3]dioxol-5-yl-5-(6-methyl-pyridin-2-yl)-1H-imidazol-2-yl]-piperidin-1-yl}-(3-chloro-phenyl)-methanone;

4-[5-benzo[1,3]dioxol-5-yl-4-(6-cyclopropyl-pyridin-2-yl)-1H-imidazol-2-yl]-bicyclo[2.2.2]octane-1-carboxylic acid;

4-[5-benzo[1,3]dioxol-5-yl-4-(6-methyl-pyridin-2-yl)-1H-imidazol-2-yl]-bicyclo[2.2.2]octane-1-carboxylic acid methoxy-amide;

4-[5-benzo[1,3]dioxol-5-yl-4-(6-methyl-pyridin-2-yl)-1H-imidazol-2-yl]-bicyclo[2.2.2]octane-1-carboxylic acid hydroxyamide;

{4-[4-benzo[1,3]dioxol-5-yl-5-(6-methyl-pyridin-2-yl)-1H-imidazol-2-yl]-cyclohexylmethyl}-carbamic acid benzyl ester;

4-[4-benzo[1,3]dioxol-5-yl-5-(6-methyl-pyridin-2-yl)-1H-imidazol-2-yl]-bicyclo[2.2.2]octane-1-carboxylic acid hydrazide;

N-{4-[4-benzo[1,3]dioxol-5-yl-5-(6-methyl-pyridin-2-yl)-1H-imidazol-2-yl]-cyclohexylmethyl}-acetamide;

N-{4-[4-benzo[1,3]dioxol-5-yl-5-(6-methyl-pyridin-2-yl)-1H-imidazol-2-yl]-cyclohexylmethyl}-methanesulfonamide;

N-{4-[4-benzo[1,3]dioxol-5-yl-5-(6-methyl-pyridin-2-yl)-1H-imidazol-2-yl]-cyclohexylmethyl}-C-phenyl-methanesulfonamide;

butane-1-sulfonic acid {4-[4-benzo[1,3]dioxol-5-yl-5-(6-methyl-pyridin-2-yl)-1H-imidazol-2-yl]-cyclohexylmethyl}-amide;

propane-2-sulfonic acid {4-[4-benzo[1,3]dioxol-5-yl-5-(6-methyl-pyridin-2-yl)-1H-imidazol-2-yl]-cyclohexylmethyl}-amide;

N-{4-[4-benzo[1,3]dioxol-5-yl-5-(6-methyl-pyridin-2-yl)-1H-imidazol-2-yl]-cyclohexylmethyl}-C-pyridin-2-yl-methanesulfonamide;

N-{4-[4-benzo[1,3]dioxol-5-yl-5-(6-methyl-pyridin-2-yl)-1H-imidazol-2-yl]-cyclohexyl}-methanesulfonamide;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid methyl ester;

4-[5-(6-methyl-pyridin-2-yl)-4-[1,2,4]triazolo[1,5-a]pyridin-6-yl-1H-imidazol-2-yl]-bicyclo[2.2.2]octane-1-carboxylic acid;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid methyl ester;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

4-[4-(6-methyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid;

4-[4-benzo[1,3]dioxol-5-yl-5-(6-methyl-pyridin-2-yl)-1H-imidazol-2-yl]-bicyclo[2.2.2]octan-1-ol;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid amide;

4-[4-(6-cyclopropyl-pyridin-2-yl)-5-[1,2,4]triazolo[1,5-a]pyridin-6-yl-1H-imidazol-2-yl]-bicyclo[2.2.2]octane-1-carboxylic acid hydroxyamide;

N-{4-[4-benzo[1,3]dioxol-5-yl-5-(6-methyl-pyridin-2-yl)-1H-imidazol-2-yl]-bicyclo[2.2.2]oct-1-yl}-sulfamide;

sulfamic acid 4-[4-benzo[1,3]dioxol-5-yl-5-(6-methyl-pyridin-2-yl)-1H-imidazol-2-yl]-bicyclo[2.2.2]oct-1-yl ester;

{4-[4-(6-methyl-pyridin-2-yl)-5-quinoxalin-6-yl-1H-imidazol-2-yl]-cyclohexyl}-carbamic acid benzyl ester;

N-{4-[4-benzo[1,3]dioxol-5-yl-5-(6-methyl-pyridin-2-yl)-1H-imidazol-2-yl]-bicyclo[2.2.2]octane-1-carbonyl}-methanesulfonamide;

N-{4-[4-benzo[1,3]dioxol-5-yl-5-(6-methyl-pyridin-2-yl)-1H-imidazol-2-yl]-bicyclo[2.2.2]octane-1-carbonyl}-benzenesulfonamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid methyl ester;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid;

N-{4-[4-(6-methyl-pyridin-2-yl)-5-quinoxalin-6-yl-1H-imidazol-2-yl]-cyclohexyl}-acetamide;

4-[4-(6-methyl-pyridin-2-yl)-5-quinoxalin-6-yl-1H-imidazol-2-yl]-bicyclo[2.2.2]octane-1-carboxylic acid methyl ester;

4-[4-(6-methyl-pyridin-2-yl)-5-quinoxalin-6-yl-1H-imidazol-2-yl]-bicyclo[2.2.2]octane-1-carboxylic acid;

4-[4-(6-methyl-pyridin-2-yl)-5-quinoxalin-6-yl-1H-imidazol-2-yl]-bicyclo[2.2.2]octane-1-carboxylic acid hydroxyamide;

4-[4-(6-methyl-pyridin-2-yl)-5-quinoxalin-6-yl-1H-imidazol-2-yl]-bicyclo[2.2.2]octane-1-carboxylic acid amide;

N-{4-[4-(6-methyl-pyridin-2-yl)-5-quinoxalin-6-yl-1H-imidazol-2-yl]-cyclohexyl}-methanesulfonamide;

2,2,2-trifluoro-N-{4-[4-(6-methyl-pyridin-2-yl)-5-quinoxalin-6-yl-1H-imidazol-2-yl]-cyclohexyl}-acetamide;

4-[5-(3-methyl-4-oxo-3,4-dihydro-quinazolin-6-yl)-4-(6-methyl-pyridin-2-yl)-1H-imidazol-2-yl]-bicyclo[2.2.2]octane-1-carboxylic acid amide;

N-{4-[5-(6-methyl-pyridin-2-yl)-4-quinoxalin-6-yl-1H-imidazol-2-yl]-bicyclo[2.2.2]oct-1-yl}-methanesulfonamide;

N-{4-[5-(6-methyl-pyridin-2-yl)-4-quinoxalin-6-yl-1H-imidazol-2-yl]-bicyclo[2.2.2]oct-1-yl}-acetamide; and 4-[4-(5-fluoro-6-methyl-pyridin-2-yl)-5-[1,2,4]triazolo[1,5-a]pyridin-6-yl-1H-imidazol-2-yl]-bicyclo[2.2.2]octane-1-carboxylic acid methyl ester.

20. A pharmaceutical composition comprising a compound of claim 1, and a pharmaceutically acceptable carrier.

21. A pharmaceutical composition comprising a compound of claim 17 and a pharmaceutically acceptable carrier.

* * * * *

UNITED STATES PATENT AND TRADEMARK OFFICE
CERTIFICATE OF CORRECTION

PATENT NO. : 7,612,094 B2 Page 1 of 1
APPLICATION NO. : 10/510459
DATED : November 3, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1011 days.

Signed and Sealed this

Nineteenth Day of October, 2010

David J. Kappos
*Director of the United States Patent and Trademark Office*